United States Patent
Barcia et al.

(10) Patent No.: US 12,208,805 B2
(45) Date of Patent: Jan. 28, 2025

(54) METHOD PROVIDED IN A CAR THAT CAN AUTOMATICALLY TAKE ACTIONS IN THE EVENT OF HEALTH RISK

(71) Applicant: Volvo Car Corporation, Gothenburg (SE)

(72) Inventors: Peter Barcia, Gothenburg (SE);
Anthony Raimondi, Gothenburg (SE);
Ronald J Roselli, Gothenburg (SE);
Kyle Caroncino, Gothenburg (SE);
Derek Boesch, Gothenburg (SE);
Giovanni Spiritoso, Gothenburg (SE)

(73) Assignee: Volvo Car Corporation, Gothenburg (SE)

( * ) Notice: Subject to any disclaimer, the term of this patent is extended or adjusted under 35 U.S.C. 154(b) by 53 days.

(21) Appl. No.: 17/982,137

(22) Filed: Nov. 7, 2022

(65) Prior Publication Data
US 2024/0149884 A1    May 9, 2024

(51) Int. Cl.
*G08B 21/02* (2006.01)
*B60K 35/00* (2006.01)
(Continued)

(52) U.S. Cl.
CPC ............ *B60W 40/08* (2013.01); *B60K 35/00* (2013.01); *B60W 50/14* (2013.01); *G16H 10/60* (2018.01); *B60K 35/28* (2024.01); *B60K 35/85* (2024.01); *B60K 2360/178* (2024.01); *B60K 2360/33* (2024.01); *B60K 2360/589* (2024.01);
(Continued)

(58) Field of Classification Search
USPC ...... 340/573.1, 426.11, 426.13, 426.19, 438, 340/439, 539.11, 539.12, 576
See application file for complete search history.

(56) References Cited

U.S. PATENT DOCUMENTS 7,877,275 B2    1/2011   Ball
9,208,289 B2 *  12/2015  Strumolo ........... B60H 1/00849
(Continued)

FOREIGN PATENT DOCUMENTS

EP    3734485 A1    11/2020
WO    2022057728 A1    3/2022

OTHER PUBLICATIONS

Search Report issued for EP Application No. 23207635.6 mailed on Apr. 12, 2024,, 8pages.

*Primary Examiner* — Daniel Previl
(74) *Attorney, Agent, or Firm* — Davé Law Group, LLC; Raj S. Davé

(57) ABSTRACT

An embodiment relates to a system, comprising: a sensor; a communication module; and a processor; wherein the processor is configured to detect that a passenger of a vehicle is experiencing a medical emergency; generate of an alert signal on an infotainment system of the vehicle; turn on automatically an emergency indication light; generate of a path from the current location of the vehicle to a target location; maneuver the vehicle along the path to the target location; identify a medical facility based upon a location of the vehicle; contact an emergency service and provide the location of the vehicle and a health condition of the passenger of the vehicle; and transmit a medical record of the passenger of the vehicle to the medical facility. According to an embodiment, the system is configured to be a component of the vehicle.

20 Claims, 28 Drawing Sheets

(51) Int. Cl.
*B60W 40/08* (2012.01)
*B60W 50/14* (2020.01)
*G16H 10/60* (2018.01)
B60K 35/28 (2024.01)
B60K 35/85 (2024.01)

(52) U.S. Cl.
CPC ... *B60W 2540/22* (2013.01); *B60W 2540/221* (2020.02); *B60W 2556/45* (2020.02)

(56) References Cited

U.S. PATENT DOCUMENTS

| | | |
|---|---|---|
| 10,007,263 B1 | 6/2018 | Fields et al. |
| 2013/0021476 A1* | 1/2013 | Trummer .................. B60R 1/00 348/148 |
| 2014/0015971 A1 | 1/2014 | Dejuliis |
| 2014/0081652 A1* | 3/2014 | Klindworth ........ G06Q 10/0635 705/2 |
| 2016/0071418 A1* | 3/2016 | Oshida ................ B60W 30/165 701/23 |
| 2016/0272114 A1* | 9/2016 | Medina .................... E05F 15/71 |
| 2017/0105104 A1* | 4/2017 | Ulmansky ............... H04W 4/42 |
| 2017/0197617 A1 | 7/2017 | Penilla et al. |
| 2018/0056784 A1* | 3/2018 | Virgilio ................ B60K 28/066 |
| 2018/0120837 A1 | 5/2018 | Regmi et al. |
| 2019/0359220 A1 | 11/2019 | Wilson et al. |
| 2021/0016781 A1 | 1/2021 | Karunai-Ramanujam et al. |
| 2021/0041868 A1* | 2/2021 | Fields ........................ G06F 8/65 |
| 2021/0271258 A1* | 9/2021 | Tran ........................ B60R 11/04 |
| 2022/0153302 A1 | 5/2022 | Arechiga-Gonzalez et al. |
| 2022/0157449 A1 | 5/2022 | Salter et al. |
| 2022/0227259 A1* | 7/2022 | Sajovic .............. G08B 21/0255 |

* cited by examiner

EXAMPLE MESSAGE TO NEARBY VEHICLE

| MESSAGE HEADER | CONTENT/INFORMATION |
|---|---|
| EVENT TYPE/ EMERGENCY TYPE | HEALTH EMERGENCY \| CHOKING |
| VEHICLE LOCATION | X : Y |
| PULL OVER TARGET LOCATION | X' : Y' |
| REQUEST SPEED | 45MPH |
| REQUEST LANE CHANGE | MOVE TO LEFT LANE |

FIG. 5A

EXAMPLE MESSAGE TO HOSPITALS/ EMERGENCY CARE

| MESSAGE HEADER | CONTENT/INFORMATION |
|---|---|
| EVENT TYPE/ EMERGENCY TYPE | HEALTH EMERGENCY \| CHOKING |
| OCCUPANT INFORMATION | JOHN^DOE \| AGE \| WEIGHT \| GENDER \| HEIGHT \|ADDRESS |
| HEALTH PARAMETERS | HEART RATE \| BP \| TEMP\| |
| VEHICLE DETAILS | VEHICLE ID\| VEHICLE LOCATION |
| OCCUPANT SEATING DETAILS | RIGHT SIDE PASSENGER SEAT IN A CHILD CAR SEAT |
| OCCUPANT PRE-HEALTH CONDITION DETAILS | DIABETES |
| OCCUPANT ALLERGY DETAILS | NIL |
| EMERGENCY CONTACT DETAILS | \|ROE^MARIE\|SPO\|(216) 555-0123\|EC\| |
| OTHER OCCUPANTS OF THE VEHICLE | JAMES^DOE |

FIG. 5B

METHOD PROVIDED IN A CAR THAT CAN AUTOMATICALLY TAKE ACTIONS IN THE EVENT OF HEALTH RISK

FIELD OF THE INVENTION

The present disclosure relates generally to the vehicle safety field. More specifically, the present disclosure relates to systems and methods for monitoring and detection of a health emergency of passengers in a vehicle and providing suggestions to assist the vehicle, a driver, or a passenger of the vehicle to handle the situation when such an emergency is detected.

BACKGROUND

The connected vehicle infrastructure provides a platform for collecting and utilizing much vehicle data that can be used advantageously in a wide variety of applications. Such applications are not limited to vehicle control and infotainment, but may also involve vehicle safety. One such safety issue is the availability of situational awareness.

The problem in today's vehicles is that there is no way to know if a child, rear facing, or a passenger seated in a vehicle is having a medical issue, such as choking, high fever, and low vital signs.

Therefore, there is a need for a system and method that can monitor and detect a health issue in real-time and provide suggestions when an emergency, for example a health emergency, is detected.

SUMMARY

The following presents a summary to provide a basic understanding of one or more embodiments described herein. This summary is not intended to identify key or critical elements or delineate any scope of the different embodiments and/or any scope of the claims. The sole purpose of the summary is to present some concepts in a simplified form as a prelude to the more detailed description presented herein.

According to an embodiment it is a system, comprising: a sensor; a communication module; and a processor; wherein the processor performs, under power, following functions, wherein the functions comprise: automatic detection, by the processor using a signal from the sensor, that a passenger of a vehicle is experiencing a medical emergency; automatic generation of an alert signal on an infotainment system of the vehicle; automatic turn on, by the processor, an emergency indication light, wherein the emergency indication light is visible to a nearby vehicle; automatic generation of a path from the current location of the vehicle to a target location; maneuver, the vehicle along the path to the target location; automatic identification, by the processor, of a medical facility based upon a location of the vehicle; automatic contact, by the processor via a communication module, to an emergency service and providing the location of the vehicle and a health condition of the passenger of the vehicle; and automatic transmission, by the processor via a communication module, of a medical record of the passenger of the vehicle to the medical facility. According to an embodiment, the system is configured to be a component of a vehicle.

An embodiment related to a vehicle, comprising: a sensor; a communication module; and a processor; wherein the processor performs, under power, following functions, wherein the functions comprise: automatic detection, by the processor using a signal from the sensor, that a passenger of a vehicle is experiencing a medical emergency; automatic generation of an alert signal on an infotainment system of the vehicle; automatic turning on, by the processor, an emergency indication light, wherein the emergency indication light is visible to a nearby vehicle; automatic generation of a path from the current location of the vehicle to a target location; maneuver, the vehicle along the path to the target location; automatic identification, by the processor, of a medical facility based upon a location of the vehicle; automatic contact, by the processor via a communication module, to an emergency service and providing the location of the vehicle and a health condition of the passenger of the vehicle; and automatic transmission, by the processor via a communication module, of a medical record of the passenger of the vehicle to the medical facility.

An embodiment related to a method, comprising: automatically detecting, by the processor using a signal from the sensor, that a passenger of a vehicle is experiencing a medical emergency; automatically generating of an alert signal on an infotainment system of the vehicle; automatically turning on, by the processor, an emergency indication light, wherein the emergency indication light is visible to a nearby vehicle; automatically generating a path from the current location of the vehicle to a target location; maneuver, the vehicle along the path to the target location; automatically identifying, by the processor, a medical facility based upon a location of the vehicle; automatically contacting, by the processor via a communication module, an emergency service and providing the location of the vehicle and a health condition of the passenger of the vehicle; and automatically transmitting, by the processor via a communication module, a medical record of the passenger of the vehicle to the medical facility.

An embodiment relates to a system configured to receive a software application installation package over a computer network; and install the software application onto the computing hardware associated with a vehicle; wherein the software application comprises: set of instructions executable by a computing hardware and stored in a non-transitory storage medium that, when executed, cause the computing hardware to implement operations comprising, detecting, by the processor using a signal from the sensor, that a passenger of a vehicle is experiencing a medical emergency; automatically generating of an alert signal on an infotainment system of the vehicle; automatically turning on, by the processor, an emergency indication light, wherein the emergency indication light is visible to a nearby vehicle; automatically generating a path from the current location of the vehicle to a target location; maneuver, the vehicle along the path to the target location; automatically identifying, by the processor, to a medical facility based upon a location of the vehicle; automatically contacting, by the processor via a communication module, an emergency service and providing the location of the vehicle and a health condition of the passenger of the vehicle; and automatically transmitting, by the processor via a communication module, a medical record of the passenger of the vehicle to the medical facility.

An embodiment related to a non-transitory computer-readable medium having stored thereon instructions executable by a computer system to perform operations comprising: automatically detecting, by the processor using a signal from the sensor, that a passenger of a vehicle is experiencing a medical emergency; automatically generating of an alert signal on an infotainment system of the vehicle; automatically turning on, by the processor, an emergency indication light, wherein the emergency indication light is visible to a nearby vehicle; automatically generating a path from the current location of the vehicle to a target location; maneuvering, the vehicle along the path to the target location; automatically identifying, by the processor, a medical facility based upon a location of the vehicle; automatically contacting, by the processor via a communication module, an emergency service and providing the location of the vehicle and a health condition of the passenger of the vehicle; and automatically providing, by the processor via a communication module, a medical record of the passenger of the vehicle to the medical facility.

An embodiment relates to a method, comprising: automatically detecting, by the processor using a signal from the sensor, that a passenger of a vehicle is experiencing a medical emergency; automatically turning on, by the processor, an emergency indication light; automatically generating, an alert signal on an infotainment system indicating a need for a pull over of the vehicle; automatically generating, a path for the pull over for the vehicle to a pull over location; maneuvering, the vehicle along the path to the pull over location; automatically identifying, by the processor, a medical facility based upon a location of the vehicle; automatically contacting, by the processor via a communication module, an emergency service and providing the location of the vehicle and a health condition of the passenger of the vehicle; and automatically transmitting, by the processor via a communication module, a medical record of the passenger of the vehicle to the medical facility.

An embodiment relates to a method, comprising: automatically detecting, by the processor using a signal from the sensor, that a passenger of a vehicle is experiencing a medical emergency; automatically turning on, by the processor, an emergency indication light; automatically generating, an alert signal on an infotainment system indicating a need for a pull over of the vehicle; automatically generating, a path for the pull over for the vehicle to a pull over location; maneuvering, the vehicle along the path to the pull over location; automatically identifying, by the processor, a medical facility based upon a location of the vehicle; waiting a predefined time, by the processor, before automatically placing a call to at least one of a medical facility, an emergency service, and a first responder; automatically contacting, after the predefined time by the processor via a communication module, an emergency service and providing the location of the vehicle and a health condition of the passenger of the vehicle; and automatically transmitting, by the processor via a communication module, a medical record of the passenger of the vehicle to the medical facility.

An embodiment relates to a vehicle, comprising: a sensor; a communication module; and a processor; wherein the processor performs, under power, the following functions, wherein the functions comprise: automatic detection, by the processor using a signal from the sensor, that a passenger of the vehicle is experiencing a medical emergency; automatic turning on, by the processor, an emergency indication light; automatic generation, an alert signal indicating a need for a pull over of the vehicle; automatic generation, a path for the pull over for the vehicle to a pull over location; maneuver, the vehicle along the path to the pull over location; automatic identification, by the processor, of a medical facility based upon a location of the vehicle; waiting a predefined time, by the processor, before automatically placing a call to at least one of a medical facility, an emergency service, and a first responder; automatic contacting, after the predefined time by the processor via a communication module, an emergency service and providing the location of the vehicle and a health condition of the passenger of the vehicle; and automatic transmission, by the processor via a communication module, of a medical record of the passenger of the vehicle to the medical facility.

An embodiment related to a method, comprising: automatically detecting, by the processor using a signal from the sensor, that a passenger of a vehicle is experiencing a medical emergency; automatically turning on, by the processor, an emergency indication light; automatically generating, an alert signal indicating a need for a pull over of the vehicle; automatically generating, a path for the pull over for the vehicle to a pull over location; maneuvering, the vehicle along the path to the pull over location; automatically identifying, by the processor, a medical facility based upon a location of the vehicle; waiting a predefined time, by the processor, before automatically placing a call to at least one of a medical facility, an emergency service, and a first responder; automatically contacting, after the predefined time by the processor via a communication module, an emergency service and providing the location of the vehicle and a health condition of the passenger of the vehicle; and automatically transmitting, by the processor via a communication module, a medical record of the passenger of the vehicle to the medical facility; and automatically transmitting, by the processor via a communication module, at least one of an image, and a video of the passenger of the vehicle to the medical facility.

An embodiment related to a method, comprising: automatically detecting, by the processor using a signal from the sensor, that a passenger of a vehicle is experiencing a medical emergency; automatically turning on, by the processor, an emergency indication light; automatically generating, an alert signal indicating a need for a pull over of the vehicle; automatically generating, a path for the pull over for the vehicle to a pull over location; maneuvering, the vehicle along the path to the pull over location; automatically identifying, by the processor, a medical facility based upon a location of the vehicle; waiting a predefined time, by the processor, before automatically placing a call to at least one of a medical facility, an emergency service, and a first responder; automatically contacting, after the predefined time by the processor via a communication module, an emergency service and providing the location of the vehicle and a health condition of the passenger of the vehicle; and automatically transmitting, by the processor via a communication module, at least one of a medical record, an image, and a video of the passenger of the vehicle to the medical facility; and receiving an instruction from the medical facility.

According to an embodiment, it is a computer system of a car, wherein the computer system is configured to, monitor a child in a rear facing car seat for a medical issue, automatically turn on hazard signal, based on traffic conditions reduce speed to allow a driver of the car to pull over to a safe location, based on health alert due to the medical issue suggest nearest urgent care of medical facility for assistance, based on health alert automatically contact 911 and provide location and health condition of the child, access medical records and provide medical records to medical professional.

BRIEF DESCRIPTION OF THE FIGURES

These and other aspects of the present invention will now be described in more detail, with reference to the appended drawings showing exemplary embodiments of the present invention, in which:

FIG. 5A shows an example emergency message and content of the message that may be used for broadcasting or communicating with nearby vehicles according to an embodiment.

FIG. 5B shows an example emergency message and content of the message that may be used for broadcasting or communicating with a first responder, an emergency care, or emergency services according to an embodiment.

DETAILED DESCRIPTION

Figure 1:
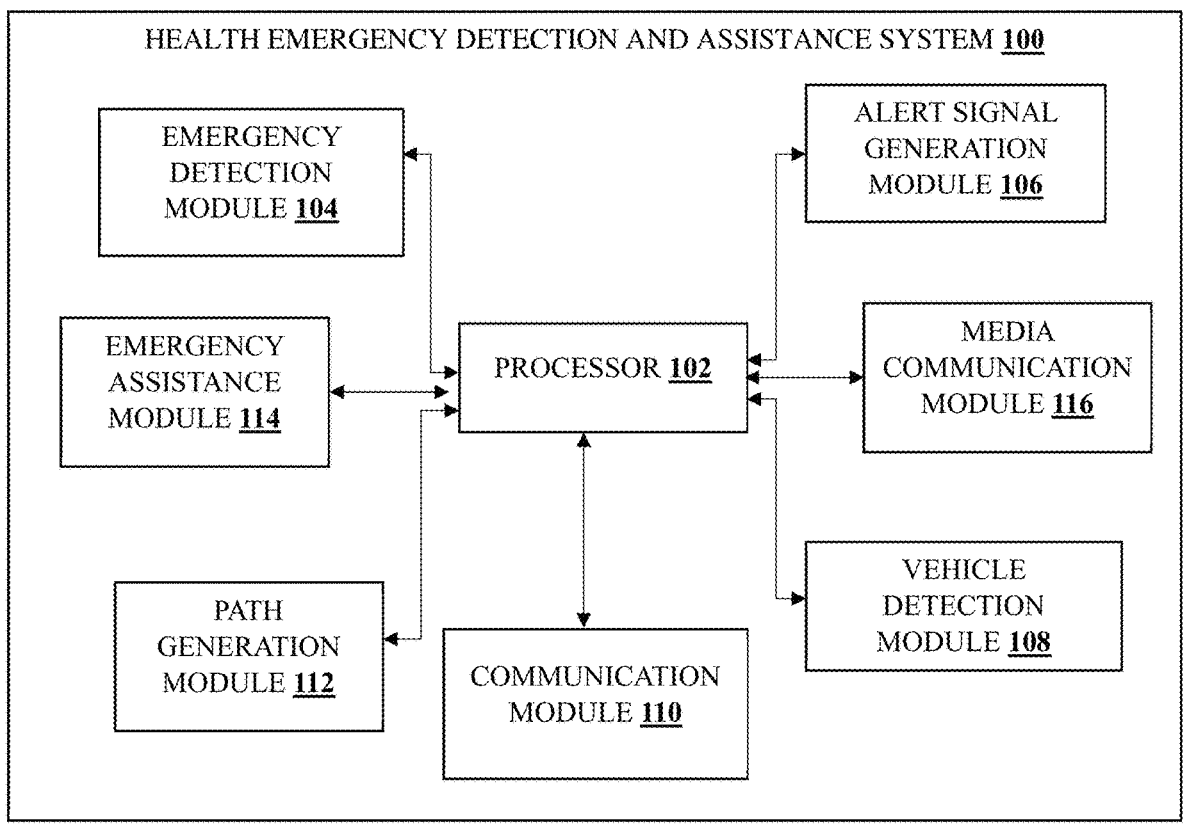
FIG. 1 shows a block diagram of various components of a system for monitoring a health emergency of a passenger of a vehicle and assisting in pull over according to an embodiment.

For simplicity and clarity of illustration, the figures illustrate the general manner of construction. The description and figures may omit the descriptions and details of well-known features and techniques to avoid unnecessarily obscuring the present disclosure. The figures exaggerate the dimensions of some of the elements relative to other elements to help improve understanding of embodiments of the present disclosure. The same reference numeral in different figures denotes the same element.

Although the herein detailed description contains many specifics for the purpose of illustration, a person of ordinary skill in the art will appreciate that many variations and alterations to the details are considered to be included herein.

Accordingly, the embodiments herein are without any loss of generality to, and without imposing limitations upon, any claims set forth. The terminology used herein is for the purpose of describing particular embodiments only and is not limiting. Unless defined otherwise, all technical and scientific terms used herein have the same meaning as commonly understood by one with ordinary skill in the art to which this disclosure belongs.

As used herein, the articles "a" and "an" used herein refer to one or to more than one (i.e., to at least one) of the grammatical object of the article. By way of example, "an element" means one element or more than one element.

Moreover, usage of articles "a" and "an" in the subject specification and annexed drawings construe to mean "one or more" unless specified otherwise or clear from context to mean a singular form.

As used herein, the terms "example" and/or "exemplary" mean serving as an example, instance, or illustration. For the avoidance of doubt, such examples do not limit the herein described subject matter. In addition, any aspect or design described herein as an "example" and/or "exemplary" is not necessarily preferred or advantageous over other aspects or designs, nor does it preclude equivalent exemplary structures and techniques known to those of ordinary skill in the art.

As used herein, the terms "first," "second," "third," and the like in the description and in the claims, if any, distinguish between similar elements and do not necessarily describe a particular sequence or chronological order. The terms are interchangeable under appropriate circumstances such that the embodiments herein are, for example, capable of operation in sequences other than those illustrated or otherwise described herein. Furthermore, the terms "include," "have," and any variations thereof, cover a non-exclusive inclusion such that a process, method, system, article, device, or apparatus that comprises a list of elements is not necessarily limiting to those elements, but may include other elements not expressly listed or inherent to such process, method, system, article, device, or apparatus.

As used herein, the terms "left," "right," "front," "back," "top," "bottom," "over," "under" and the like in the description and in the claims, if any, are for descriptive purposes and not necessarily for describing permanent relative positions. The terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein is critical or essential unless explicitly described as such. Furthermore, the term "set" includes items (e.g., related items, unrelated items, a combination of related items and unrelated items, etc.) and may be interchangeable with "one or more". Where only one item is intended, the term "one" or similar language is used. Also, the terms "has," "have," "having," or the like are open-ended terms. Further, the phrase "based on" means "based, at least in part, on" unless explicitly stated otherwise.

As used herein, the terms "system," "device," "unit," and/or "module" refer to a different component, component portion, or component of the various levels of the order. However, other expressions that achieve the same purpose may replace the terms.

As used herein, the terms "couple," "coupled," "couples," "coupling," and the like refer to connecting two or more elements mechanically, electrically, and/or otherwise. Two or more electrical elements may be electrically coupled together, but not mechanically or otherwise coupled together. Coupling may be for any length of time, e.g., permanent, or semi-permanent or only for an instant. "Electrical coupling" includes electrical coupling of all types. The absence of the word "removably," "removable," and the like, near the word "coupled" and the like does not mean that the coupling, etc. in question is or is not removable.

As used herein, the term "or" means an inclusive "or" rather than an exclusive "or." That is, unless specified otherwise, or clear from context, "X employs A or B" means any of the natural inclusive permutations. That is, if X employs A; X employs B; or X employs both A and B, then "X employs A or B" is satisfied under any of the foregoing instances.

As used herein, two or more elements or modules are "integral" or "integrated" if they operate functionally together. Two or more elements are "non-integral" if each element can operate functionally independently.

As used herein, the term "real-time" refers to operations conducted as soon as practically possible upon occurrence of a triggering event. A triggering event can include receipt of data necessary to execute a task or to otherwise process information. Because of delays inherent in transmission and/or in computing speeds, the term "real-time" encompasses operations that occur in "near" real-time or somewhat delayed from a triggering event. In a number of embodiments, "real-time" can mean real-time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

As used herein, the term "approximately" can mean within a specified or unspecified range of the specified or unspecified stated value. In some embodiments, "approximately" can mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value. Other specific forms may embody the present invention without departing from its spirit or characteristics. The described embodiments are in all respects illustrative and not restrictive. Therefore, the appended claims rather than the description herein indicate the scope of the invention. All variations which come within the meaning and range of equivalency of the claims are within their scope.

As used herein, the term "component" broadly construes hardware, firmware, and/or a combination of hardware, firmware, and software.

Digital electronic circuitry, or in computer software, firmware, or hardware, including the structures disclosed in this specification and their structural equivalents, or in combinations of one or more of them may realize the implementations and all of the functional operations described in this specification. Implementations may be as one or more computer program products i.e., one or more modules of computer program instructions encoded on a computer-readable medium for execution by, or to control the operation of, data processing apparatus. The computer-readable medium may be a machine-readable storage device, a machine-readable storage substrate, a memory device, a composition of matter affecting a machine-readable propagated signal, or a combination of one or more of them. The term "computing system" encompasses all apparatus, devices, and machines for processing data, including by way of example, a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal (e.g., a machine-generated electrical, optical, or electromagnetic signal) that encodes information for transmission to a suitable receiver apparatus.

The actual specialized control hardware or software code used to implement these systems and/or methods is not limiting to the implementations. Thus, any software and any hardware can implement the systems and/or methods based on the description herein without reference to specific software code.

A computer program (also known as a program, software, software application, script, or code) is written in any appropriate form of programming language, including compiled or interpreted languages. Any appropriate form, including a standalone program or a module, component, subroutine, or other unit suitable for use in a computing environment may deploy it. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may execute on one computer or on multiple computers that are located at one site or distributed across multiple sites and interconnected by a communication network.

One or more programmable processors, executing one or more computer programs to perform functions by operating on input data and generating output, perform the processes and logic flows described in this specification. The processes and logic flows may also be performed by, and apparatus may also be implemented as, special purpose logic circuitry, for example, without limitation, a Field Programmable Gate Array (FPGA), an Application Specific Integrated Circuit (ASIC), Application Specific Standard Products (ASSPs), System-On-a-Chip (SOC) systems, Complex Programmable Logic Devices (CPLDs), etc.

Processors suitable for the execution of a computer program include, by way of example, both general and special purpose microprocessors, and any one or more processors of any appropriate kind of a digital computer. A processor will receive instructions and data from a read-only memory or a random-access memory or both. Elements of a computer can include a processor for performing instructions and one or more memory devices for storing instructions and data. A computer will also include, or is operatively coupled to receive data, transfer data or both, to/from one or more mass storage devices for storing data e.g., magnetic disks, magneto optical disks, optical disks, or solid-state disks. However, a computer need not have such devices. Moreover, another device, e.g., a mobile telephone, a personal digital assistant (PDA), a mobile audio player, a Global Positioning System (GPS) receiver, etc. may embed a computer. Computer-readable media suitable for storing computer program instructions and data include all forms of non-volatile memory, media and memory devices, including, by way of example, semiconductor memory devices (e.g., Erasable Programmable Read-Only Memory (EPROM), Electronically Erasable Programmable Read-Only Memory (EEPROM), and flash memory devices), magnetic disks (e.g., internal hard disks or removable disks), magneto optical disks (e.g. Compact Disc Read-Only Memory (CD ROM) disks, Digital Versatile Disk-Read-Only Memory (DVD-ROM) disks) and solid-state disks. Special purpose logic circuitry may supplement or incorporate the processor and the memory.

To provide for interaction with a user, a computer may have a display device, e.g., a Cathode Ray Tube (CRT) or Liquid Crystal Display (LCD) monitor, for displaying information to the user, and a keyboard and a pointing device, e.g., a mouse or a trackball, by which the user may provide input to the computer. Other kinds of devices provide for interaction with a user as well. For example, feedback to the user may be any appropriate form of sensory feedback, e.g., visual feedback, auditory feedback, or tactile feedback; and a computer may receive input from the user in any appropriate form, including acoustic, speech, or tactile input.

A computing system that includes a back-end component, e.g., a data server, or that includes a middleware component, e.g., an application server, or that includes a front-end component, e.g., a client computer having a graphical user interface or a Web browser through which a user may interact with an implementation, or any appropriate combination of one or more such back-end, middleware, or front-end components, may realize implementations described herein. Any appropriate form or medium of digital data communication, e.g., a communication network may interconnect the components of the system. Examples of communication networks include a Local Area Network (LAN) and a Wide Area Network (WAN), e.g., Intranet and Internet.

The computing system may include clients and servers. A client and server are remote from each other and typically interact through a communication network. The relationship of the client and server arises by virtue of computer programs running on the respective computers and having a client-server relationship to each other.

Embodiments of the present invention may comprise or utilize a special purpose or general purpose computer including computer hardware. Embodiments within the scope of the present invention may also include physical and other computer-readable media for carrying or storing computer-executable instructions and/or data structures. Such computer-readable media can be any media accessible by a general purpose or special purpose computer system. Computer-readable media that store computer-executable instructions are physical storage media. Computer-readable media that carry computer-executable instructions are transmission media. Thus, by way of example and not limitation, embodiments of the invention can comprise at least two distinct kinds of computer-readable media: physical computer-readable storage media and transmission computer-readable media.

Although the present embodiments described herein are with reference to specific example embodiments it will be evident that various modifications and changes may be made to these embodiments without departing from the broader spirit and scope of the various embodiments. For example, hardware circuitry (e.g., Complementary Metal Oxide Semiconductor (CMOS) based logic circuitry), firmware, software (e.g., embodied in a non-transitory machine-readable medium), or any combination of hardware, firmware, and software may enable and operate the various devices, units, and modules described herein. For example, transistors, logic gates, and electrical circuits (e.g., Application Specific Integrated Circuit (ASIC) and/or Digital Signal Processor (DSP) circuit) may embody the various electrical structures and methods.

In addition, a non-transitory machine-readable medium and/or a system may embody the various operations, processes, and methods disclosed herein. Accordingly, the specification and drawings are illustrative rather than restrictive.

Physical computer-readable storage media includes RAM, ROM, EEPROM, CD-ROM or other optical disk storage (such as CDs, DVDs, etc.), magnetic disk storage or other magnetic storage devices, solid-state disks or any other medium. They store desired program code in the form of computer-executable instructions or data structures which can be accessed by a general purpose or special purpose computer.

As used herein, the term "network" refers to one or more data links that enable the transport of electronic data between computer systems and/or modules and/or other electronic devices. When a network or another communications connection (either hardwired, wireless, or a combination of hardwired or wireless) transfers or provides information to a computer, the computer properly views the connection as a transmission medium. A general purpose or special purpose computer access transmission media that can include a network and/or data links which carry desired program code in the form of computer-executable instructions or data structures. The scope of computer-readable media includes combinations of the above, that enable the transport of electronic data between computer systems and/ or modules and/or other electronic devices.

Further, upon reaching various computer system components, program code in the form of computer-executable instructions or data structures can be transferred automatically from transmission computer-readable media to physical computer-readable storage media (or vice versa). For example, computer-executable instructions or data structures received over a network or data link can be buffered in RAM within a Network Interface Module (NIC), and then eventually transferred to computer system RAM and/or to less volatile computer-readable physical storage media at a computer system. Thus, computer system components that also (or even primarily) utilize transmission media may include computer-readable physical storage media.

Computer-executable instructions comprise, for example, instructions and data which cause a general purpose computer, special purpose computer, or special purpose processing device to perform a certain function or group of functions. The computer-executable instructions may be, for example, binary, intermediate format instructions such as assembly language, or even source code. Although the subject matter herein described is in a language specific to structural features and/or methodological acts, the described features or acts described do not limit the subject matter defined in the claims. Rather, the herein described features and acts are example forms of implementing the claims.

While this specification contains many specifics, these do not construe as limitations on the scope of the disclosure or of the claims, but as descriptions of features specific to particular implementations. A single implementation may implement certain features described in this specification in the context of separate implementations. Conversely, multiple implementations separately or in any suitable subcombination may implement various features described herein in the context of a single implementation. Moreover, although features described herein as acting in certain combinations and even initially claimed as such, one or more features from a claimed combination may in some cases be excised from the combination, and the claimed combination may be directed to a sub-combination or variation of a sub-combination.

Similarly, while operations depicted herein in the drawings in a particular order to achieve desired results, this should not be understood as requiring that such operations be performed in the particular order shown or in sequential order or that all illustrated operations be performed, to achieve desirable results. In certain circumstances, multitasking and parallel processing may be advantageous. Moreover, the separation of various system components in the implementations should not be understood as requiring such separation in all implementations, and it should be understood that the described program components and systems may be integrated together in a single software product or packaged into multiple software products.

Even though particular combinations of features are recited in the claims and/or disclosed in the specification, these combinations are not intended to limit the disclosure of possible implementations. Other implementations are within the scope of the claims. For example, the actions recited in the claims may be performed in a different order and still achieve desirable results. In fact, many of these features may be combined in ways not specifically recited in the claims and/or disclosed in the specification. Although each dependent claim may directly depend on only one claim, the disclosure of possible implementations includes each dependent claim in combination with every other claim in the claim set.

Further, a computer system including one or more processors and computer-readable media such as computer memory may practice the methods. In particular, one or more processors execute computer-executable instructions, stored in the computer memory, to perform various functions such as the acts recited in the embodiments.

Those skilled in the art will appreciate that the invention may be practiced in network computing environments with many types of computer system configurations including personal computers, desktop computers, laptop computers, message processors, hand-held devices, multiprocessor systems, microprocessor-based or programmable consumer electronics, network PCs, minicomputers, mainframe computers, mobile telephones, PDAs, pagers, routers, switches, etc. Distributed system environments where local and remote computer systems, which are linked (either by hardwired data links, wireless data links, or by a combination of hardwired and wireless data links) through a network, both perform tasks may also practice the invention. In a distributed system environment, program modules may be located in both local and remote memory storage devices.

The following terms and phrases, unless otherwise indicated, shall be understood to have the following meanings.

As used herein, the term "Cryptographic protocol" is also known as security protocol or encryption protocol. It is an abstract or concrete protocol that performs a security-related function and applies cryptographic methods often as sequences of cryptographic primitives. A protocol describes usage of the algorithms A sufficiently detailed protocol includes details about data structures and representations, to implement multiple, interoperable versions of a program.

Secure application-level data transport widely use cryptographic protocols. A cryptographic protocol usually incorporates at least some of these aspects: key agreement or establishment, entity authentication, symmetric encryption, and message authentication material construction, secured application-level data transport, non-repudiation methods, secret sharing methods, and secure multi-party computation.

Networking switches use cryptographic protocols, like Secure Socket Layer (SSL) and Transport Layer Security (TLS), the successor to SSL, to secure data communications over a wireless network.

As used herein, the term "Unauthorized access" is when someone gains access to a website, program, server, service, or other system using someone else's account or other methods. For example, if someone kept guessing a password or username for an account that was not theirs until they gained access, it is considered unauthorized access.

As used herein, the term "IoT" stands for Internet of Things which describes the network of physical objects "things" or objects embedded with sensors, software, and other technologies for the purpose of connecting and exchanging data with other devices and systems over the internet.

As used herein "Machine learning" refers to algorithms that give a computer the ability to learn without explicit programming, including algorithms that learn from and make predictions about data. Machine learning algorithms include, but are not limited to, decision tree learning, artificial neural networks (ANN) (also referred to herein as a "neural net"), deep learning neural network, support vector machines, rules-based machine learning, random forest, etc. For the purposes of clarity, part of a machine learning process can use algorithms such as linear regression or logistic regression. However, using linear regression or another algorithm as part of a machine learning process is distinct from performing a statistical analysis such as regression with a spreadsheet program. The machine learning process can continually learn and adjust the classifier as new data becomes available and does not rely on explicit or rules-based programming. The ANN may be featured with a feedback loop to adjust the system output dynamically as it learns from the new data as it becomes available. In machine learning, backpropagation and feedback loops are used to train the AI/ML model improving the model's accuracy and performance over time.

Statistical modeling relies on finding relationships between variables (e.g., mathematical equations) to predict an outcome.

As used herein, the term "Data mining" is a process used to turn raw data into useful information.

As used herein, the term "Data acquisition" is the process of sampling signals that measure real world physical conditions and converting the resulting samples into digital numeric values that a computer manipulates. Data acquisition systems typically convert analog waveforms into digital values for processing. The components of data acquisition systems include sensors to convert physical parameters to electrical signals, signal conditioning circuitry to convert sensor signals into a form that can be converted to digital values, and analog-to-digital converters to convert conditioned sensor signals to digital values. Stand-alone data acquisition systems are often called data loggers.

As used herein, the term "Dashboard" is a type of interface that visualizes particular Key Performance Indicators (KPIs) for a specific goal or process. It is based on data visualization and infographics.

As used herein, a "Database" is a collection of organized information so that it can be easily accessed, managed, and updated. Computer databases typically contain aggregations of data records or files.

As used herein, the term "Data set" (or "Dataset") is a collection of data. In the case of tabular data, a data set corresponds to one or more database tables, where every column of a table represents a particular variable, and each row corresponds to a given record of the data set in question. The data set lists values for each of the variables, such as height and weight of an object, for each member of the data set. Each value is known as a datum. Data sets can also consist of a collection of documents or files.

As used herein, a "Sensor" is a device that measures physical input from its environment and converts it into data that is interpretable by either a human or a machine. Most sensors are electronic, which presents electronic data, but some are simpler, such as a glass thermometer, which presents visual data.

The term "vehicle" as used herein refers to a thing used for transporting people or goods. Automobiles, cars, trucks, buses etc. are examples of vehicles. The term "electronic control unit" (ECU), also known as an "electronic control module" (ECM), is a system that controls one or more subsystems. An ECU may be installed in a car or other motor vehicle. It may refer to many ECUs, and can include but not limited to, Engine Control Module (ECM), Powertrain Control Module (PCM), Transmission Control Module (TCM), Brake Control Module (BCM) or Electronic Brake Control Module (EBCM), Central Control Module (CCM), Central Timing Module (CTM), General Electronic Module (GEM), Body Control Module (BCM), and Suspension Control Module (SCM). ECUs together are sometimes referred to collectively as the vehicles' computer or vehicles' central computer and may include separate computers. In an example, the electronic control unit can be embedded system in automotive electronics. In another example, the electronic control unit is wirelessly coupled with the automotive electronics.

The term "infotainment system" or "in-vehicle infotainment system" (IVI) as used herein refers to a combination of vehicle systems which are used to deliver entertainment and information. In an example, the information may be delivered to the driver and the passengers of a vehicle/occupants through audio/video interfaces, control elements like touch screen displays, button panel, voice commands, and more. Some of the main components of an in-vehicle infotainment systems are integrated head-unit, heads-up display, high-end Digital Signal Processors (DSPs), and Graphics Processing Units (GPUs) to support multiple displays, operating systems, Controller Area Network (CAN), Low-Voltage Differential Signaling (LVDS), and other network protocol support (as per the requirement), connectivity modules, automotive sensors integration, digital instrument cluster, etc. The term "environment" or "surrounding" as used herein refers to surroundings and the space in which a vehicle is navigating. It refers to dynamic surroundings in which a vehicle is navigating which includes other vehicles, obstacles, pedestrians, lane boundaries, traffic signs and signals, speed limits, potholes, snow, water logging etc.

The term "autonomous mode" as used herein refers to an operating mode which is independent and unsupervised.

The term "autonomous communication" as used herein comprises communication over a period with minimal supervision under different scenarios and is not solely or completely based on pre-coded scenarios or pre-coded rules or a predefined protocol. Autonomous communication, in general, happens in an independent and an unsupervised manner.

The term "autonomous vehicle" also referred to as self-driving vehicle, driverless vehicle, robotic vehicle as used herein refers to a vehicle incorporating vehicular automation, that is, a ground vehicle that can sense its environment and move safely with little or no human input. Self-driving vehicles combine a variety of sensors to perceive their surroundings, such as thermographic cameras, Radio Detection and Ranging (radar), Light Detection and Ranging (lidar), Sound Navigation and Ranging (sonar), Global Positioning System (GPS), odometry and inertial measurement unit. Control systems, designed for the purpose, interpret sensor information to identify appropriate navigation paths, as well as obstacles and relevant signage.

The term "communication system" or "communication module" as used herein refers to a system which enables the information exchange between two points. The process of transmission and reception of information is called communication. The major elements of communication include but are not limited to a transmitter of information, channel or medium of communication and a receiver of information.

The term "connection" as used herein refers to a communication link. It refers to a communication channel that connects two or more devices for the purpose of data transmission. It may refer to a physical transmission medium such as a wire, or to a logical connection over a multiplexed medium such as a radio channel in telecommunications and computer networking. A channel is used for information transfer of, for example a digital bit stream, from one or several senders to one or several receivers. A channel has a certain capacity for transmitting information, often measured by its bandwidth in Hertz (Hz) or its data rate in bits per second. For example, a Vehicle-to-Vehicle (V2V) communication may wirelessly exchange information about the speed, location and heading of surrounding vehicles.

The term "communication" as used herein refers to the transmission of information and/or data from one point to another. Communication may be by means of electromagnetic waves. It is also a flow of information from one point, known as the source, to another, the receiver. Communication comprises one of the following: transmitting data, instructions, and information or a combination of data, instructions, and information. Communication happens between any two communication systems or communicating units. The term "in communication with" may refer to any coupling, connection, or interaction using electrical signals to exchange information or data, using any system, hardware, software, protocol, or format, regardless of whether the exchange occurs wirelessly or over a wired connection. The term communication includes systems that combine other more specific types of communication, such as V2I (Vehicle-to-Infrastructure), V2I (Vehicle-to-Infrastructure), V2N (Vehicle-to-Network), V2V (Vehicle-to-Vehicle), V2P (Vehicle-to-Pedestrian), V2D (Vehicle-to-Device) and V2G (Vehicle-to-Grid) and Vehicle-to-Everything (V2X) communication. V2X communication is the transmission of information from a vehicle to any entity that may affect the vehicle, and vice versa. The main motivations for developing V2X are occupant safety, road safety, traffic efficiency and energy efficiency. Depending on the underlying technology employed, there are two types of V2X communication technologies: cellular networks and other technologies that support direct device-to-device communication (such as Dedicated Short-Range Communication (DSRC), Port Community System (PCS), Bluetooth®, Wi-Fi®, etc.). Further, the emergency communication apparatus is configured on a computer with the communication function and is connected for bidirectional communication with the on-vehicle emergency report apparatus by a communication line through a radio station and a communication network such as a public telephone network or by satellite communication through a communication satellite. The emergency communication apparatus is adapted to communicate, through the communication network, with communication terminals including a road management office, a police station, a fire department, and a hospital. The emergency communication apparatus can be also connected online with the communication terminals of the persons concerned, associated with the occupant (the driver receiving the service) of the emergency-reporting vehicle. The term "vehicle to vehicle (V2V) communication" refers to the technology that allows vehicles to broadcast and receive messages. The messages may be omni-directional messages, creating a 360-degree "awareness" of other vehicles in proximity Vehicles may be equipped with appropriate software (or safety applications) that can use the messages from surrounding vehicles to determine potential crash threats as they develop.

The term "protocol" as used herein refers to a procedure required to initiate and maintain communication; a formal set of conventions governing the format and relative timing of message exchange between two communications terminals; a set of conventions that govern the interaction of processes, devices, and other components within a system; a set of signaling rules used to convey information or commands between boards connected to the bus; a set of signaling rules used to convey information between agents; a set of semantic and syntactic rules that determine the behavior of entities that interact; a set of rules and formats (semantic and syntactic) that determines the communication behavior of simulation applications; a set of conventions or rules that govern the interactions of processes or applications within a computer system or network; a formal set of conventions governing the format and relative timing of message exchange in a computer system; a set of semantic and syntactic rules that determine the behavior of functional units in achieving meaningful communication; a set of semantic and syntactic rules for exchanging information.

The term "communication protocol" as used herein refers to standardized communication between any two systems. An example communication protocol is of Health Level Seven (HL7). HL7 is a set of international standards used to provide guidance with transferring and sharing data between various healthcare providers. HL7 is a comprehensive framework and related standards for the exchange, integration, sharing, and retrieval of electronic health information.

The term "bidirectional communication" as used herein refers to an exchange of data between two components. In an example, the first component can be a vehicle and the second component can be an infrastructure that is enabled by a system of hardware, software, and firmware. This communication is typically wireless.

The term "pull over" as used herein refers to steering a vehicle over to the side of the road. This enables the vehicle to be stopped or parked at the side of the road. The term "path" as used herein refers to a way or track for movement. For example, a pull over path may be a path that the vehicle traverses for a pull over. It may refer to a path selected from a plurality of feasible paths that were computed or possible for a pull over.

The term "alert" or "alert signal" refers to a communication to attract attention. An alert may include visual, tactile, audible alert, and a combination of these alerts to warn drivers or occupants. These alerts allow, drivers or occupants, the ability to act and respond quickly to avoid or navigate through the emergency situation.

The term, "biophysical measurement" as used herein refers to measurement of physical changes that take place over a period of time related to a specific indicator that can be measured using an accepted measurement procedure. This provides statistically reliable data that can form the basis for measuring impact and change. Biophysical sensors monitor metabolites, pH, electrolytes, heart rate, arterial oxygenation, sweat rate, and skin temperature, etc., from biophysical signals. It may refer to any signal in living beings that can be continually measured and monitored. The term may also be referred to as bio-signal and is often used to refer to bioelectrical signals, but it may refer to both electrical and non-electrical signals. It may refer to time-varying signals, although spatial parameter variations are sometimes subsumed as well.

The term "rule-based system" as used herein comprises a set of facts of a scenario and a set of rules for how to deal with the set of facts comprising if and then statements, wherein the scenario is predefined in a system.

The term, "physiological characteristic" as used herein refers to a characteristic relating to physiology that is indicative of a healthy or normal functioning human. Example physiological characteristics include, but are not limited to, heart rate, blood pressure, respiration, body temperature, etc.

The term, "bio signal" is any signal in human beings that can be continually measured or monitored. Example bio signals include electrocardiogram (ECG), electroencephalogram (EEG), electromyogram (EMG), electrooculogram (EOG), galvanic skin response, magneto encephalography (MEG), etc.

As used herein, a "bio-sensor" or "biosensor" is an analytical device, used for the detection of a chemical substance, that combines a biological component with a physicochemical detector. The sensitive biological element, e.g., tissue, microorganisms, organelles, cell receptors, enzymes, antibodies, nucleic acids, etc., is a biologically derived material or biomimetic component that interacts with, binds with, or recognizes the analyte under study. The biosensor may include pulse oximeter, heart rate sensor, ECG sensor, skin sensors, temperature sensor, blood pressure sensor, impedance sensor etc. In an embodiment, the biosensor includes a biometric device. The biometric device uses automated methods of verifying or recognizing the identity of a living person based on a physiological or behavioral characteristic. These characteristics include fingerprints, facial images, iris, and voice recognition. Information generated or received by the sensors and biosensor may be communicated to the on-board computer or the mobile device for use in autonomous vehicle operation.

The term "occupant" as used herein, refers to a passenger in the vehicle and it includes the driver. Passenger and occupant are used interchangeably and refer to a person in the vehicle during a ride.

The term "nearby vehicle" as used herein refers to surrounding vehicles of the user's vehicle and is within reach of at least a communication range of the user's vehicle wherein the communication range is defined as the maximum distance where communication can exist between two antennas, one of which is user's vehicle antenna in a wireless network.

The term "maneuver" as used herein refers to carefully move, steer, or drive a vehicle, in order to move from one point to another point.

The term "first responder" as used herein refers to a person with specialized training who is among the first to arrive and provide assistance at the scene of an emergency, such as an accident. First responders typically include law enforcement officers, paramedics, Emergency Medical Technicians (EMT's) and firefighters. In some areas, emergency department personnel, such as nurses and doctors, are also required to respond to disasters and critical situations, designating them first responders. It may sometimes refer to a person who may be a doctor or nurse, may or may not be certified by law as first responder, but responds first to a message of the user's vehicle and can offer medical help due to their qualification.

The term "electronic health record system" or "(EHR) system" refers to electronic record of health-related information on an individual that can be created, gathered, managed, and consulted by authorized clinicians and staff within one health care organization. Health records from the EHR system are usually procured using third-party software suites.

The term "feature" as used herein in relation to machine learning and pattern recognition, represents or refers to an individual measurable property or characteristic of a phenomenon. Features are usually numeric, but structural features such as strings and graphs are used in syntactic pattern recognition. The concept of "feature" is related to that of explanatory variables used in statistical techniques such as linear regression.

The term "syntactic pattern recognition" or "structural pattern recognition" refers to a form of pattern recognition, in which each object can be represented by a variable-cardinality set of symbolic, nominal features. This allows for representing pattern structures, considering more complex interrelationships between attributes than is possible in the case of flat, numerical feature vectors of fixed dimensionality, which are used in statistical classification. Syntactic pattern recognition can be used instead of statistical pattern recognition if there is clear structure in the patterns. One way to present such a structure is by means of strings of symbols from a formal language. In this case the differences in the structures of the classes are encoded as different grammars. An example of this would be diagnosis of the heart with ECG measurements. ECG waveforms can be approximated with diagonal and vertical line segments. If normal and unhealthy waveforms can be described as formal grammars, measured ECG signal can be classified as healthy or unhealthy by first describing it in terms of the basic line segments and then trying to parse the descriptions according to the grammars.

The term "application server" refers to a server that hosts applications or software that delivers a business application through a communication protocol. An application server framework is a service layer model. It includes software components available to a software developer through an application programming interface. It is system software that resides between the operating system (OS) on one side, the external resources such as a database management system (DBMS), communications and Internet services on another side, and the users' applications on the third side.

The term "cyber security" as used herein refers to application of technologies, processes, and controls to protect systems, networks, programs, devices, and data from cyber-attacks.

The term "cyber security module" as used herein refers to a module comprising application of technologies, processes, and controls to protect systems, networks, programs, devices and data from cyber-attacks and threats. It aims to reduce the risk of cyber-attacks and protect against the unauthorized exploitation of systems, networks, and technologies. It includes, but is not limited to, critical infrastructure security, application security, network security, cloud security, Internet of Things (IoT) security.

The term "encrypt" used herein refers to securing digital data using one or more mathematical techniques, along with a password or "key" used to decrypt the information. It refers to converting information or data into a code, especially to prevent unauthorized access. It may also refer to concealing information or data by converting it into a code. It may also be referred to as cipher, code, encipher, encode. A simple example is representing alphabets with numbers— say, 'A' is '01', 'B' is '02', and so on. For example, a message like "HELLO" will be encrypted as "0805121215," and this value will be transmitted over the network to the recipient(s).

The term "decrypt" used herein refers to the process of converting an encrypted message back to its original format. It is generally a reverse process of encryption. It decodes the encrypted information so that only an authorized user can decrypt the data because decryption requires a secret key or password. This term could be used to describe a method of unencrypting the data manually or unencrypting the data using the proper codes or keys.

The term "cyber security threat" used herein refers to any possible malicious attack that seeks to unlawfully access data, disrupt digital operations, or damage information. A malicious act includes but is not limited to damaging data, stealing data, or disrupting digital life in general. Cyber threats include, but are not limited to, malware, spyware, phishing attacks, ransomware, zero-day exploits, trojans, advanced persistent threats, wiper attacks, data manipulation, data destruction, rogue software, malvertising, unpatched software, computer viruses, man-in-the-middle attacks, data breaches, Denial of Service (DoS) attacks, and other attack vectors.

The term "hash value" used herein can be thought of as fingerprints for files. The contents of a file are processed through a cryptographic algorithm, and a unique numerical value, the hash value, is produced that identifies the contents of the file. If the contents are modified in any way, the value of the hash will also change significantly. Example algorithms used to produce hash values: the Message Digest-5 (MD5) algorithm and Secure Hash Algorithm-1 (SHA1).

The term "integrity check" as used herein refers to the checking for accuracy and consistency of system related files, data, etc. It may be performed using checking tools that can detect whether any critical system files have been changed, thus enabling the system administrator to look for unauthorized alteration of the system. For example, data integrity corresponds to the quality of data in the databases and to the level by which users examine data quality, integrity, and reliability. Data integrity checks verify that the data in the database is accurate, and functions as expected within a given application.

The term "alarm" as used herein refers to a trigger when a component in a system or the system fails or does not perform as expected. The system may enter an alarm state when a certain event occurs. An alarm indication signal is a visual signal to indicate the alarm state. For example, when a cyber security threat is detected, a system administrator may be alerted via sound alarm, a message, a glowing LED, a pop-up window, etc. Alarm indication signal may be reported downstream from a detecting device, to prevent adverse situations or cascading effects.

The term "in communication with" as used herein, refers to any coupling, connection, or interaction using electrical signals to exchange information or data, using any system, hardware, software, protocol, or format, regardless of whether the exchange occurs wirelessly or over a wired connection.

As used herein, the term "network" may include the Internet, a local area network, a wide area network, or combinations thereof. The network may include one or more networks or communication systems, such as the Internet, the telephone system, satellite networks, cable television networks, and various other private and public networks. In addition, the connections may include wired connections (such as wires, cables, fiber optic lines, etc.), wireless connections, or combinations thereof. Furthermore, although not shown, other computers, systems, devices, and networks may also be connected to the network. Network refers to any set of devices or subsystems connected by links joining (directly or indirectly) a set of terminal nodes sharing resources located on or provided by network nodes. The computers use common communication protocols over digital interconnections to communicate with each other. For example, subsystems may comprise the cloud. Cloud refers to servers that are accessed over the Internet, and the software and databases that run on those servers.

The embodiments described herein can be directed to one or more of a system, a method, an apparatus, and/or a computer program product at any possible technical detail level of integration. The computer program product can include a computer readable storage medium (or media) having computer readable program instructions thereon for causing a processor to carry out aspects of the one or more embodiments described herein. The computer readable storage medium can be a tangible device that can retain and store instructions for use by an instruction execution device. For example, the computer readable storage medium can be, but is not limited to, an electronic storage device, a magnetic storage device, an optical storage device, an electromagnetic storage device, a superconducting storage device, and/or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon and/or any suitable combination of the foregoing. A computer readable storage medium, as used herein, does not construe transitory signals per se, such as radio waves and/or other freely propagating electromagnetic waves, electromagnetic waves propagating through a waveguide and/or other transmission media (e.g., light pulses passing through a fiber-optic cable), and/or electrical signals transmitted through a wire.

Computer readable program instructions described herein are downloadable to respective computing/processing devices from a computer readable storage medium and/or to an external computer or external storage device via a network, for example, the Internet, a local area network, a wide area network and/or a wireless network. The network can comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the one or more embodiments described herein can be assembler instructions, instruction-set-architecture (ISA) instructions, machine instructions, machine dependent instructions, microcode, firmware instructions, state-setting data, configuration data for integrated circuitry, and/or source code and/or object code written in any combination of one or more programming languages, including an object oriented programming language such as Smalltalk, C++ or the like, and/or procedural programming languages, such as the "C" programming language and/or similar programming languages. The computer readable program instructions can execute entirely on a computer, partly on a computer, as a stand-alone software package, partly on a computer and/or partly on a remote computer or entirely on the remote computer and/or server. In the latter scenario, the remote computer can be connected to a computer through any type of network, including a local area network (LAN) and/or a wide area network (WAN), and/or the connection can be made to an external computer (for example, through the Internet using an Internet Service Provider). In one or more embodiments, electronic circuitry including, for example, programmable logic circuitry, field-programmable gate arrays (FPGA), and/or programmable logic arrays (PLA) can execute the computer readable program instructions by utilizing state information of the computer readable program instructions to personalize the electronic circuitry, in order to perform aspects of the one or more embodiments described herein.

Aspects of the one or more embodiments described herein are described with reference to flowchart illustrations and/or block diagrams of methods, apparatus (systems), and computer program products according to one or more embodiments described herein. Each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer and/or other programmable data processing apparatus to produce a machine, such that the instructions, which execute via the processor of the computer or other programmable data processing apparatus, can create means for implementing the functions/acts specified in the flowchart and/or block diagram block or blocks. These computer readable program instructions can also be stored in a computer readable storage medium that can direct a computer, a programmable data processing apparatus and/or other devices to function in a particular manner, such that the computer readable storage medium having instructions stored therein can comprise an article of manufacture including instructions which can implement aspects of the function/act specified in the flowchart and/or block diagram block or blocks. The computer readable program instructions can also be loaded onto a computer, other programmable data processing apparatus and/or other device to cause a series of operational acts to be performed on the computer, other programmable apparatus and/or other device to produce a computer implemented process, such that the instructions which execute on the computer, other programmable apparatus and/or other device implement the functions/acts specified in the flowchart and/or block diagram block or blocks.

The flowcharts and block diagrams in the figures illustrate the architecture, functionality and/or operation of possible implementations of systems, computer-implementable methods and/or computer program products according to one or more embodiments described herein. In this regard, each block in the flowchart or block diagrams can represent a module, segment and/or portion of instructions, which comprises one or more executable instructions for implementing the specified logical function(s). In one or more alternative implementations, the functions noted in the blocks can occur out of the order noted in the Figures. For example, two blocks shown in succession can be executed substantially concurrently, and/or the blocks can sometimes be executed in the reverse order, depending upon the functionality involved. It will also be noted that each block of the block diagrams and/or flowchart illustration, and/or combinations of blocks in the block diagrams and/or flowchart illustration, can be implemented by special purpose hardware-based systems that can perform the specified functions and/or acts and/or carry out one or more combinations of special purpose hardware and/or computer instructions.

While the subject matter described herein is in the general context of computer-executable instructions of a computer program product that runs on a computer and/or computers, those skilled in the art will recognize that the one or more embodiments herein also can be implemented in combination with one or more other program modules. Program modules include routines, programs, components, data structures, and/or the like that perform particular tasks and/or implement particular abstract data types. Moreover, other computer system configurations, including single-processor and/or multiprocessor computer systems, mini-computing devices, mainframe computers, as well as computers, hand-held computing devices (e.g., PDA, phone), microprocessor-based or programmable consumer and/or industrial electronics and/or the like can practice the herein described computer-implemented methods. Distributed computing environments, in which remote processing devices linked through a communications network perform tasks, can also practice the illustrated aspects. However, stand-alone computers can practice one or more, if not all aspects of the one or more embodiments described herein. In a distributed computing environment, program modules can be located in both local and remote memory storage devices.

As used in this application, the terms "component," "system," "platform," "interface," and/or the like, can refer to and/or can include a computer-related entity or an entity related to an operational machine with one or more specific functionalities. The entities described herein can be either hardware, a combination of hardware and software, software, or software in execution. For example, a component can be, but is not limited to being, a process running on a processor, a processor, an object, an executable, a thread of execution, a program and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system and/or across a network such as the Internet with other systems via the signal). As another example, a component can be an apparatus with specific functionality provided by mechanical parts operated by electric or electronic circuitry, which is operated by a software and/or firmware application executed by a processor. In such a case, the processor can be internal and/or external to the apparatus and can execute at least a part of the software and/or firmware application. As yet another example, a component can be an apparatus that provides specific functionality through electronic components without mechanical parts, where the electronic components can include a processor and/or other means to execute software and/or firmware that confers at least in part the functionality of the electronic components. In an aspect, a component can emulate an electronic component via a virtual machine, e.g., within a cloud computing system.

As it is employed in the subject specification, the term "processor" can refer to any computing processing unit and/or device comprising, but not limited to, single-core processors; single-processors with software multithread execution capability; multi-core processors; multi-core processors with software multithread execution capability; multi-core processors with hardware multithread technology; parallel platforms; and/or parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, and/or any combination thereof designed to perform the functions described herein. Further, processors can exploit nano-scale architectures such as, but not limited to, molecular based transistors, switches and/or gates, in order to optimize space usage and/or to enhance performance of related equipment. A combination of computing processing units can implement a processor.

Herein, terms such as "store," "storage," "data store," data storage," "database," and any other information storage component relevant to operation and functionality of a component refer to "memory components," entities embodied in a "memory," or components comprising a memory. Memory and/or memory components described herein can be either volatile memory or nonvolatile memory or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, and/or nonvolatile random access memory (RAM) (e.g., ferroelectric RAM (FeRAM). Volatile memory can include RAM, which can function as external cache memory, for example. By way of illustration and not limitation, RAM can be available in many forms such as synchronous RAM (SRAM), dynamic RAM (DRAM), synchronous DRAM (SDRAM), double data rate SDRAM (DDR SDRAM), enhanced SDRAM (ESDRAM), Synch link DRAM (SLDRAM), direct Rambus RAM (DRRAM), direct Rambus dynamic RAM (DRDRAM) and/or Rambus dynamic RAM (RDRAM). Additionally, the described memory components of systems and/or computer-implemented methods herein include, without being limited to including, these and/or any other suitable types of memory.

The embodiments described herein include mere examples of systems and computer-implemented methods. It is, of course, not possible to describe every conceivable combination of components and/or computer-implemented methods for purposes of describing the one or more embodiments, but one of ordinary skill in the art can recognize that many further combinations and/or permutations of the one or more embodiments are possible. Furthermore, to the extent that the terms "includes," "has," "possesses," and the like are used in the detailed description, claims, appendices and/or drawings such terms are intended to be inclusive in a manner similar to the term "comprising" as "comprising" is interpreted when employed as a transitional word in a claim.

The descriptions of the one or more embodiments are for purposes of illustration but are not exhaustive or limiting to the embodiments described herein. Many modifications and variations will be apparent to those of ordinary skill in the art without departing from the scope and spirit of the described embodiments. The terminology used herein best explains the principles of the embodiments, the practical application and/or technical improvement over technologies found in the marketplace, and/or to enable others of ordinary skill in the art to understand the embodiments described herein.

The problem in today's vehicles is that there is no way to know if your child, rear facing, or a passenger is having a medical issue, such as choking, high fever, low vital signs. There needs to be a system that can monitor and provide suggestions when a health issue is detected.

In the future when vehicles can be connected, the system will alert all vehicles nearby of an emergency and request vehicles to provide a clear pathway for the user's vehicle to pull over. Once the vehicle determines an emergency has occurred, for example, a health issue has occurred, it will connect with all vehicles surrounding the user's vehicle. Once the connection has been established, the system can calculate the required speed of the vehicles based on the location to provide a clear path to pull over. In one aspect, the system can request, depending on the country's traffic rules, for example, that all vehicles on the right side in the United States of America (USA) to slow down so that the user's vehicle can pull over.

In the future, many vehicles will be connected via various communication modes. If a vehicle is traveling in traffic, and an emergency happens, that may require the vehicle to get off the road. However, there are vehicles everywhere, surrounding the user's vehicle. Surrounding vehicles, or the nearby vehicles do not know what is happening to the vehicle where an emergency is detected. In one embodiment, the system detects that there is an issue, for example a health emergency is happening in the vehicle or vehicle. Then, the system would try to clear a path on either side of the road or to one side of the road. It is similar to having a vehicle's own siren, for example, like having a vehicle tuned into an ambulance which can clear the path for itself.

FIG. 1 shows a block diagram of various components of a system for monitoring a health emergency of a passenger of a vehicle and assisting in pull over according to an embodiment. The system 100 may comprise a processor 102. In an embodiment, the processor can include a plurality of processors. The system 100 may comprise different modules or subsystems, as shown in FIG. 1, which are communicatively coupled, such as emergency detection module 104, alert signal generation module 106, vehicle detection module 108, communication module 110, path generation module 112, emergency assistance module 114, and media communication module 116. In an embodiment, all the modules may be configured into a single module or may comprise separate modules.

The Emergency detection module 104 may comprise a health monitoring system. The passenger's state of health may be determined through image or video processing of the passenger's face and body. For example, the heartbeat of a human can be measured with video processing of the green channel for a red, green, blue (RGB) image sensor. In other examples, the passenger monitoring system may detect choking, coughing, sneezing, and sweating through similar video processing methodologies. Using combinations of these information streams, a sophisticated software algorithm may make predictions and suggest an emergency, a severity, and a possible suggestion to address the emergency situation. Using machine learning and video processing, a passenger's weight trends and organ failure (e.g., kidney failure) may be determined through changes in the skin color, blotchiness, droopiness, and darkness. The facial expression feature is measured by picking up an image of the face of the passenger by the charge coupled device (CCD) camera, or the like, installed in the vehicle, pointed directly at the face of the passenger, and measuring the facial expression features of the passenger from the image data using the image processing technique. The camera may be installed on the interior side of the roof of the vehicle, which can have more than one degree of freedom to monitor the passenger from different angles. In an embodiment, there may be a plurality of cameras monitoring the passenger from different angles.

In an embodiment, it is a system for detecting if a vehicle passenger is experiencing a problematic health situation, which may be an emergency situation, and responding to those situations. In the system, sensors in a vehicle monitor, record, and/or detect physiological characteristics of a passenger of the vehicle. Additionally, environmental sensors monitor, record, and/or detect environmental characteristics of the vehicle itself. By detecting the physiological characteristics of the vehicle passenger, receiving physiological characteristic measurements, and using machine learning, the system can determine a baseline for each physiological characteristic corresponding to a specific vehicle passenger (e.g., a driver of the vehicle). The system can then compare newly received physiological characteristic measurements with the baseline for that particular physiological characteristic to determine whether the newly received physiological characteristic measurement is not within the limits of the baseline.

In some embodiments, passenger wellness data may include biophysical data of the passenger. In some embodiments, biophysical data of the passenger may be collected or otherwise monitored through one or more biophysical sensors, such as sensors implementable in a vehicle. Sensors may be located at various locations in or on the vehicle, in the vehicle seats, in the child vehicle seats, in the belts, on the steering wheel, mirrors, etc. In some embodiments, sensors may be in contact with, or worn by, the passenger to monitor or collect biophysical data. For example, a sensor may be a heart rate sensor embedded in a seatbelt of the vehicle and configured to provide a heart rate reading of the heart rate of the passenger as biophysical data when the seatbelt is engaged with or worn by the driver. As another example, a sensor may be a blood pressure sensor arranged or placed on an armrest of a vehicle seat of the vehicle and configured to provide a blood pressure reading of the blood pressure of the passenger when the passenger places his or her arm on the armrest. Likewise, sensors may include a thermometer, a respiratory rate monitor, a blood glucose monitor, or the like, to provide biophysical data of the passenger, such as a body temperature reading, a respiration reading, a blood glucose reading, or the like. In some embodiments, sensors may include a video camera or an infrared image sensor to capture video(s) and/or image(s) of the passenger and provide imagery data indicative of a body movement, an eye movement, or a facial distortion of the passenger as biophysical data. Using facial detection or other image processing techniques, a processor may analyze the video(s) or image(s) and accordingly determine the emergency situation and its severity. For example, sensors may include a video camera, and processors may analyze a video received from the video camera and find that the passenger may have passed out in the vehicle seat when the passenger movement is not detected. The processor may determine this condition to be very likely an emergency related to the health of the passenger, of which the emergency severity may be given a scale of 1-10, with 10 being very severe or life threatening.

In some embodiments, passenger wellness data may also include a medical history of the passenger, and/or a set of emergency-triggering thresholds of the passenger. Medical history may include information on one or more pre-existing medical condition(s) of the passenger, such as hypertension, asthma, or diabetes for example. Medical history of the driver may be transmitted from a remote location, such as a cloud server of a medical service provider and received as other data 1006 through a communication device thereof. Alternatively, medical history of the passenger may be readily stored in memory of the emergency detection system. The processor may analyze the medical history of the passenger while determining emergency severity. For example, the processor may analyze medical history and find that the passenger is a diabetic, and thus may monitor a blood glucose reading of biophysical data received from a blood glucose sensor among sensors. In some embodiments, passenger wellness data of the passenger may include a set of emergency-triggering thresholds associated with the specific passenger, which may be provided by a medical doctor or medical service provider. For example, in the case of the diabetic passenger, the set of emergency-triggering thresholds may include a "life-threatening" lower bound blood glucose threshold of 80 mg/dl (milligram per deciliter), and a "non-life-threatening" lower bound blood glucose threshold of 100 mg/dl, as dictated by a medical service provider. In this example, the processor may determine that there is no potential emergency incident should the blood glucose sensor report a reading higher than 100 mg/dl. Moreover, the processor may determine that there is a potential emergency incident of "life-threatening" severity should the blood glucose sensor report a reading lower than 80 mg/dl. Furthermore, the processor may determine that there is a potential emergency incident of "less-than-life-threatening" severity should the blood glucose sensor report a reading between 80 mg/dl and 100 mg/dl.

Additionally, or alternatively, in some embodiments, the processors may determine emergency severity based on a correlation among passenger wellness data, vehicle motion data, driver wellness data and/or driver distraction or distress data. The vehicle motion data may include various motion parameters of the vehicle, such as a speed of the vehicle, a moving direction of the vehicle, and/or a distance between the vehicle and a nearby object. Motion data of the vehicle may be collected or otherwise monitored through one or more motion detectors positioned in or on the vehicle. The motion detectors may include one or more of a speedometer, a global positioning device, a video camera, and a proximity sensor.

The alert signal generation module 106 may generate an alert when an emergency is detected. It may further control information displayed on an infotainment system, a rear display, and a front display. A display may be designed to display information to different intended users, depending on the positioning of the user's vehicle and the other vehicles. In an embodiment, the display data may include stored display patterns, sequences, colors, text, animation, or other data to be displayed on the front and/or rear display. The display data may also include algorithms for generating content and controlling how it is displayed. The generated content, for example, may be personalized based on information received from the system, any third-party system, the vehicle, and the computing devices. In an embodiment, there may be indicators outside the vehicle to inform that an emergency is happening, for example a light around the registration plate, a light around the windows of the vehicle. Each color of a light or display may indicate a type of emergency. For example, a red or blue light may be configured to indicate an emergency in the health of the vehicle.

In an embodiment, icons on a graphical user interface (GUI) or display of the infotainment system of a computer system are re-arranged based on a priority score of the content of the message. The processor tracks the messages that need to be displayed at a given time and generates a priority score, wherein the priority score is determined based on the action that needs to be taken by the user, the time available before the user input is needed, content of the message to be displayed, criticality of the user's input/action that needs to be taken, the sequence of the message or messages that need to be displayed and executed, and the safety of the overall scenario. For example, in case of a health emergency, the messages in queue for displaying could be an emergency signal, type of emergency, intimation that an alert is provided to the nearby vehicles, instructing a path for the driver to pull over, calling the emergency services, etc. In all these messages that need a driver's attention, a priority score is provided based on the actions that need to be taken by the user, the time available for the user to receive the displayed message and react with an action, the content of the message, criticality of the user's input/action, sequence of the messages that need to be executed, and safety of the overall scenario. Considering the above example, the message that intimates the user/driver that an alert has been provided to nearby vehicles may be of lower priority as compared to instructing the path for the driver to pull over. Therefore, the pull over directions for the path message takes priority and takes such a place on the display (example, center of the display) which can grab the users' attention immediately. The priority of the messages are evaluated dynamically as the situation is evolving and thus the display icons, positions, and sizes of the text or icon on the display are changed in real time and dynamically. In an embodiment, more than one message is displayed and highlighted as per the situation and the user's actions. Further, while pulling over, if an unsafe scenario is found for example, a car is changing lanes which may obstruct the user's vehicle, the message dynamically changes and warns the driver about the developing scenario.

The vehicle detection module 108 may include vision-based vehicle detection. Vision sensors may be coupled with methods such as deep learning methods with Region-based Convolutional Neural Networks (R-CNNs) or Fast R-CNNs. In an embodiment, a radar system is used for object-detection which uses radio waves to determine the range, direction, or speed of objects. It may be configured to detect motor vehicles. The radar antenna transmits pulses of radio waves which bounce off any object in their path. The object returns a small part of the wave's energy to the receiver antenna which is usually located at the same site as the transmitter. In an embodiment, the sensor that detects the nearby vehicles comprises at least one of an infrared sensor, an ultrasonic sensor, a radar sensor, a passive acoustic detector array, a piezoelectric sensor, a photoelectric sensor and a camera.

The communication module 110 enables in-vehicle communication, communication with other vehicles, infrastructure communication, grid communication, etc., using Vehicle to network (V2N), Vehicle to infrastructure (V2I), Vehicle to vehicle (V2V), Vehicle to cloud (V2C), Vehicle to pedestrian (V2P), Vehicle to device (V2D), Vehicle to grid (V2G) communication systems. For example, if a child stopped breathing, for some reason, during a trip in a vehicle or car, first, the system detects that a health emergency has happened. Then, the system notifies nearby or surrounding vehicles or vehicles using the vehicle's communication module. The vehicle or vehicle uses, for example, a message protocol, a message that goes to the other vehicles via a broadcast. In an embodiment, the broadcast message comprises the information of the emergency. In an embodiment, the broadcast message comprises the information of the emergency and the location of the vehicle. In another embodiment, the broadcast message comprises the information of the emergency, the location of the vehicle relative to the vehicle receiving the broadcast message and a pull over target location. In an embodiment, a graphic can be created from the message received on the receiver's vehicle. In an embodiment, the broadcast message is sent by the vehicle communication module as soon as the emergency is detected. In another embodiment, the system waits a certain period of time and then broadcasts the message. In another embodiment, the system provides an option to the user if it can broadcast an emergency message. For example, a vehicle which is next to the vehicle experiencing an emergency situation, receives an alert which specifies that the vehicle next to it is in an emergency and is trying to pull over. The vehicle experiencing an emergency may actually provide its location. Based on the broadcast message, the receiver of the broadcast message may actually slow down. In an embodiment, the system will automatically access the control of the nearby vehicle and slow or speed-up the nearby car/vehicle as needed. In case of an autonomous driving vehicle, the nearby vehicle may automatically slow down if it receives the broadcast emergency message. In an embodiment, the vehicle experiencing the emergency may automatically override the control of the autonomous vehicle to reduce the speed, change a lane, increase the speed, or a combination thereof. In an embodiment, the system may alert nearby vehicles that there is an emergency in a vehicle and provide a relative location of the vehicle experiencing the emergency to the nearby vehicles. The nearby vehicle user may voluntarily slow the car/vehicle as the vehicle experiencing an emergency is going to slow down and could actually come to a complete stop. The vehicle experiencing an emergency may send a broadcast message to all the surrounding vehicles to let the vehicles know that the vehicle is in trouble. In an embodiment, the message comprises the type of emergency. Such a broadcast message will help nearby vehicles to assist the vehicle experiencing an emergency. In an embodiment, the message protocol comprises the type of emergency and a location of the vehicle experiencing the emergency. If there is a doctor in a nearby vehicle, they may realize the situation, and may try to pull over and assist the driver immediately so that the situation is handled as quickly as possible.

In an embodiment, a connection is established between the user vehicle and a nearby vehicle which is a surrounding car. A nearby vehicle is detected by the vehicle control system. The nearby vehicle is detected by exchanging handshaking signals. The handshaking is the automated process for negotiation of setting up a communication channel between entities. The processor sends a start signal through the communication channel in order to detect a nearby vehicle. If there is a nearby vehicle, the processor may receive an acknowledgement signal from the nearby vehicle. Upon receiving the acknowledgement signal, the processor establishes a secured connection with the nearby vehicle. The processor may receive a signal at the communication module from the nearby vehicle. The processor may further automatically determine the origin of the signal. The processor communicatively connects the communication module to the nearby vehicle. Then the processor is configured to send and/or receive a message from the nearby vehicle. The signals received by the communication module may be analyzed to identify the origin of the signal to determine a location of the nearby vehicle.

In an embodiment, the vehicle experiencing the emergency could control the speed of a nearby vehicle. In an embodiment, the broadcast message is enabled in order to seek assistance from the other vehicles or to control the other vehicles automatically, without user intervention, so that the vehicle undergoing emergency can get the assistance as soon as possible. In an embodiment, if the nearby vehicle is in autonomous driving mode, the vehicle experiencing an emergency can broadcast a message to let the user in the autonomous vehicle know the emergency and request the control of, or automatically control, the nearby autonomous vehicle.

In an embodiment, the system is enabled for bidirectional communication. The system is sending a signal and then receiving a communication. In an embodiment, it could be a permission for an access to control the other vehicle. In another embodiment, it could be an incremental control. For example, an initial control of the speed up to 10 miles per hour, then further additional 10 miles per hour, and so on. In an embodiment, the vehicle experiencing the emergency may request or control for a complete stop. In another embodiment, the vehicle experiencing the emergency may request or control for a pull over of the nearby vehicle.

As a first step of the method according to the disclosure, a data link between the vehicle and nearby vehicle, an emergency care, an emergency services, or any other external device is set up in order to permit data to be exchanged between the vehicle and the nearby vehicle, emergency care, emergency services, or any other external device in the form of a bidirectional communication. This can take place, for example, via a radio link or a data cable. It is therefore possible for the nearby vehicle, emergency care, emergency services, or any other external device to receive data from the vehicle, or else for the vehicle to request data from the nearby vehicle, an emergency care, an emergency services, or any other external device.

In an embodiment, bidirectional communication comprises the means for data acquisition and are designed to exchange data bidirectionally with one another. In addition, at least the vehicle comprises the logical means for gathering the data and arranging it to a certain protocol based on the receiving entity's protocol.

Initially, a data link for bidirectional communication is set up. The vehicle and the nearby vehicle, emergency care, emergency services, or any other external device can communicate with one another via this data link and therefore request or exchange data, wherein the data link can be implemented, for example, as a cable link or radio link.

Bidirectional communication has various advantages as described herein. In various embodiments, data is communicated and transferred at a suitable interval, including, for example, 200 millisecond (ms) intervals, 100 ms intervals, 50 ms intervals, 20 ms intervals, 10 ms intervals, or even more frequently and/or in real-time or near real-time, in order to allow system to respond to or otherwise react to data. Bidirectional IR communication may be used to facilitate the data exchange.

The apparatus for the vehicle according to the embodiment that performs bidirectional communication may be by means of a personal area network (PAN) modem. Therefore, a user can have access to an external device using the vehicle information terminal, and can then store, move, and delete the user's desired data.

In one embodiment, the broadcast message comprises the location of the vehicle. In another embodiment, the broadcast message comprises a type of alert, for example, a health alert from the alert signal generation module. In an embodiment, may comprise a request to return a message if the situational awareness has changed, for example, if there is medical personnel in a nearby vehicle. Then, the system receives the information from the medical personnel in the nearby vehicle about the details of the medical personnel vehicle, its location, and the medical personnel name from the responder. In an embodiment, the communication is established between the medical personnel (first responder) and the vehicle undergoing the emergency, and further information on the identity of the first responder, specialization, hospital affiliation is sought. In an embodiment, the details are received and verified by the vehicle system or a third party.

In an embodiment, the health alert system or system provides the images of the person who is undergoing a medical emergency. In an embodiment, the information is provided after receiving consent from the user of the vehicle.

In an embodiment, the vehicle undergoing an emergency can request the nearby vehicle to slow down. The vehicle undergoing an emergency, using its broadcast, the vehicle communication may monitor, and identify that the nearby vehicle, after slowing down, is still too close. The user's vehicle may send another request to the nearby vehicle to slow down even more. The system can actually continue doing that when a request is sent to a nearby vehicle to slow down and to what degree of control is sought from the nearby vehicle. The vehicle undergoing an emergency can request a nearby vehicle to slow down and the nearby vehicle will start slowing down. The system will gradually approximate, by using back and forth signaling that says slow down five miles per hour, and then request for a receival of the current speed of the nearby vehicle. The system continues bidirectional communication to approximate or estimate how far the nearby vehicle is from the vehicle undergoing the emergency and how much further the nearby vehicle needs to slow down. In an embodiment, the system forms a zone of influence based on a distance of the nearby vehicle. Depending on where the vehicles are, the system decides based on different zones of influence, different instructions. In an embodiment, the system detects or recognizes different classes of actors to send a signal to. In an embodiment, the system has different rules for communicating with different classes of actors. For example, if there is an ambulance as a nearby vehicle or if there is a doctor in a nearby vehicle, they would fall into one category of actors. The nearby vehicles and their drivers and passengers would be the general category, unless they respond that they have a doctor onboard, or they are an ambulance. In an embodiment, the alert signal and the message protocol is different for each zone and each actor. In an embodiment, the information of the actors can be provided by a third party service.

As an example, considering distances in a heavy traffic situation, if there is a doctor that responded and is about four vehicles behind the vehicle experiencing emergency, then establishing a vehicle-to-vehicle communication with the nearby vehicle having the doctor, he/she can let the vehicle experiencing the emergency know that he/she is located about four vehicles behind. The doctor, in an embodiment, is referred to as a first responder. First responders comprise a person, such as a police officer or an emergency medical technician (EMT) who is among those responsible for going immediately to the scene of an accident or emergency to provide assistance. There is a second class, which comprises doctors and healthcare professionals who are near the area. Then there is a third class, which are just normal or standard drivers and passengers that are unable to assist medically but can assist by getting out of the way. In an embodiment, the first and second responders, when they receive a broadcast message of an emergency, can actually send information back to that vehicle, letting the vehicle know that they are nearby by providing their location and asking the vehicle experiencing the emergency to pull over for assistance. In an embodiment, credentials are transmitted to ensure a person is trustworthy and is not a random person.

In an embodiment, a broadcast message is sent out. In another embodiment, the message is transmitted, and a response is received. In an embodiment, a health risk is identified. A first message is broadcast comprising a health alert and a first responder request. A message may be received from a first responder. In another embodiment, the message may request either a first or a second responder. In an embodiment, a communication is established with an identified first responder, or the healthcare professionals within that area. Once the communication link is established and the credentials are verified or accepted, then the health data of the passenger undergoing an emergency comprising vital signs is sent to the first responder. In an embodiment, the vehicle may receive information about the responder, for example, type of actor (doctor, health technician, etc.), type of vehicle (ambulance, private vehicle, etc.), location of the vehicle (within a 1 mile radius, or street ahead of you, etc.). In an embodiment, the responder may send a message confirming that there is no need to make a 911 (emergency services) call and that they can assist. In an embodiment, the communication between the vehicle experiencing an emergency and the nearby vehicle have specific protocols for communication. In an embodiment, the vehicle experiencing an emergency will delay making the 911 call for a predefined time when it receives a message from the first responder who can provide help within that predefined time. For example, if there is an ambulance that is 20 seconds away from the vehicle, then the system will wait before it makes the 911 call. In an embodiment, the system will start sending messages for clearing the path for assisting further. In another embodiment, when a first responder, any healthcare professional responds to an emergency message, the system would wait a predefined time before making a call to emergency services, a police officer, or any further action.

In an embodiment, the health issue can come from a vehicle that the system has identified and verified that there is a health issue. The system is triggered if it receives information from the vehicle seat or the external device that is inside the vehicle that identifies or detects an emergency inside the vehicle. In an embodiment, the system that enables the health emergency or the emergency alert signal will prevent the abuse of the system when a manual intervention is present.

In an embodiment, the system comprises a cyber security module and is configured to secure the health data and personal data of the passenger. In an embodiment of the system, wherein the action comprises a display of the alert signal on an external vehicle display textual and graphical content indicating the detected in-vehicle emergency.

In an embodiment, the system further comprises a cyber security module wherein the cyber security module comprises an information security management module providing isolation between the communication module and servers.

In an embodiment, the information security management module is operable to, receive data from the communication module, exchange a security key at a start of the communication between the communication module and the server, receive the security key from the server, authenticate an identity of the server by verifying the security key, analyze the security key for a potential cyber security threat, negotiate an encryption key between the communication module and the server, encrypt the data; and transmit the encrypted data to the server when no cyber security threat is detected.

In an embodiment, the information security management module is operable to exchange a security key at a start of the communication between the communication module and the server, receive the security key from the server, authenticate an identity of the server by verifying the security key, analyze the security key for a potential cyber security threat, negotiate an encryption key between the system and the server, receive encrypted data from the server, decrypt the encrypted data, perform an integrity check of the decrypted data and transmit the decrypted data to the communication module when no cyber security threat is detected.

In an embodiment, the system is enabled for the Good Samaritan Law. Many states in a country have different versions of the Good Samaritan Law. If a person tried to help somebody, in cases of an accident or distress, and it caused more harm than good for the accident victim, the helping person is not held liable as the intention for helping is a good intention. Where such a Good Samaritan law is not available, the vehicle passenger may waive his/her rights to sue the helper. In this way more people will have the desire, without fear, to help or come forward to help. In an embodiment, the Good Samaritan Law indicator was added against future liability as part of the communication. For example, the communication message may be appended with the indicator which conveys that the "Good Samaritan Law is present" or simply a code for the same, such as "GSL-P." In case of the absence of the Good Samaritan Law, the system may seek the passenger's consent for the waiver of rights to sue the helper. If the vehicle passenger waives it, the message could be appended with an indicator "not held liable for helping." If the first responder can assist the person who was requesting help, even in those states that do not have the Good Samaritan Law or protection against it, it may be established via messaging that that person needs help and that the person helping cannot be held liable for any consequences. In an embodiment, the Good Samaritan Law based on location is stored in a database. The system connects to the database and extracts the information on the law applicability. In an embodiment, the system finds the real-time location of the vehicle and the location is used to extract the applicability of law. In an embodiment, the user, when purchasing the vehicle or vehicle, may be asked for the waiver of rights to sue against the helper/first responder in case of an accident. The consent may be taken through an app, or a built-in system within the vehicle. In an embodiment, it is a one-time consent provided and valid for the lifetime of the vehicle. In another embodiment, the system can ask for the waiver of rights to sue against the helper every time the seat belt is buckled. The option, for one time or every time, to ask for a waiver can be changed using settings in the system. The system can encode the collected information from the user into the communication message, in case of an accident. In an embodiment, the system for consent on waiver can manually be activated by the user. In an embodiment, the user acknowledges the waiver not during the emergency, but prior to the emergency. In an embodiment, a manual activation that will alert, at a press of a button, and will start broadcasting. In an embodiment, a message is only transmitted if it is determined that there is no such identifiable Good Samaritan Law that protects the helper to reduce the bandwidth of the message. In an embodiment, the message is sent when the law is applicable for the state based on the vehicle location. The system determines, based on the vehicle's real-time location, that there is no need to transmit the waiver as the Good Samaritan Law is applicable. In the event that it does not have the data, or the location does not have the law, then that waiver is actually transmitted. In an embodiment the waiver is added into the transmission in a broadcast message that goes out to all nearby vehicles. In an embodiment, setup options comprising emergency situations or preferences may be used for collecting the waiver consent from the user. As soon as the vehicle seat is connected, an acceptance of the waiver pops up, and when the user accepts or rejects, the reply is recorded. In an emergency situation, the system would provide a waiver message based on the user's response. In an embodiment, the data can be transmitted to a central database.

In an embodiment, the vehicle where the emergency is happening will transmit a message. It can be using any or combination of vehicle to vehicle (V2V), vehicle to everything (V2X) or vehicle to infrastructure (V2I) type of communication. In an embodiment, it uses Vehicle-to-vehicle (V2V) communication that enables vehicles to wirelessly exchange information about their speed, location, and heading.

Path generation module 112 comprises hardware such as sensors, circuits and processors and software such as methods, programs, and algorithms, which would enable the computation and generation of a path from a current location to a second location while considering the surrounding dynamic environment. In an embodiment, the path generation module computes a path based on certain speed and location of the nearby vehicles, and the communication module communicates a request speed and/or course to the nearby vehicles so that the nearby vehicles can adjust their current speed to the requested speed and/or current course to the requested course to enable the vehicle experiencing an emergency situation to navigate through the traffic to a destination point.

The emergency assistance module 114 enables the system to automatically turn on hazard signals. Based on traffic conditions, reduce speed to allow the driver to pull over to a safe location. Based on a health alert, suggest nearest urgent care of a medical facility that can assist. Based on the health alert, automatically contact emergency services (911), and provide the location and health condition of the child or the passenger. Access medical records and provide them to medical professionals in the emergency care that was contacted. In an embodiment, the user would have to provide authorization before sharing the medical records.

In an embodiment, the system automatically switches on the hazard signal as soon as it detects an emergency. Once the hazard signal is switched on, based on traffic conditions, the car would help manage the traffic speeds and let the user's car reduce the speed, allowing the driver to pull over safely. In an embodiment, if a health emergency is happening, the system would automatically slow down the car and may enter into an autonomous mode. Further, based on the type of health alert and severity, the system can notify the nearest urgent care or medical facility that can assist. The nearest health facility may be the closest in terms of distance, time, or a medical center that has the required care facilities.

In an embodiment, the system would allow the driver to focus on getting the car off the road, or to the urgent care and at the same time, continue monitoring, and then decide whether a call for emergency services (911) is necessary. In an embodiment, the system monitors the driver's distress via health sensors in the driver's seat, steering wheel, and personal health wearables. Further the driver is monitored with camera and video. The features extracted from the health data, image data and video data are used to find whether the driver is in distress or having anxiety and are correlated with the passenger's health status and are used by the emergency assistance module 114 for deciding whether to pull over or continue to medical center, call emergency services or not.

Media communication module 116 comprises hardware such as an audio or video recorder and software such as methods, programs and algorithms that would enable recording the condition of the passenger. In an embodiment, the media communication module interacts with the first responder by sending and receiving the instruction from the first responder. In an embodiment, interaction with the first responder could be via wireless communication. The media communication module 116 may communicate with the various devices as provided herein. Optionally, the media communication module 116 can provide content, information, data, and/or media associated with the passenger of the vehicle to one or more devices such as mobile phones, a device that is located or associated with the vehicle, a wearable device that can include heart rate monitors, blood pressure monitors, glucose monitors, pedometers, movement sensors, wearable computers, and the like. Examples of wearable computers may be worn by the passenger and configured to measure passenger activity, determine energy spent based on the measured activity, track user sleep habits, determine user oxygen levels, monitor heart rate, provide alarm functions, and more. It is anticipated that the wearable devices can communicate with the processor via wireless communications channels or direct connection (e.g., where the device docks, or connects, with a USB port or similar interface of the vehicle).

Figure 2A:
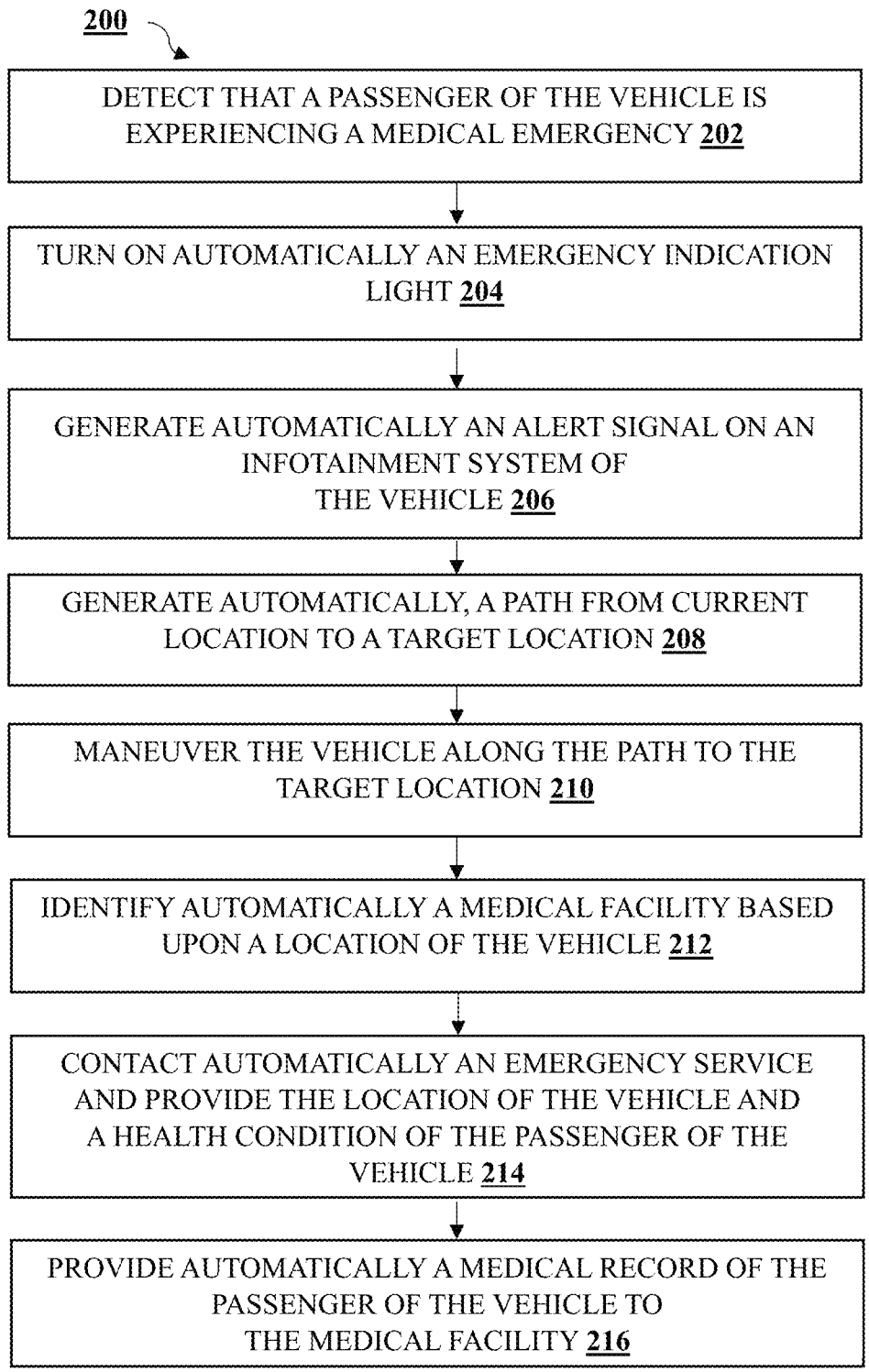
FIG. 2A shows a flowchart for a method for monitoring and detecting the health emergency of the passenger of the vehicle and assisting in the emergency situation according to an embodiment.

FIG. 2A shows a flowchart for a method for monitoring and detecting the health emergency of the passenger of the vehicle and assisting in the emergency situation according to an embodiment. According to FIG. 2A, method 200, comprises, automatically detects, that a passenger of a vehicle is experiencing a medical emergency at 202. Detection of emergency could be based on sensor data, biophysical sensors, cameras, and video processing. Then the method automatically generates an alert signal on an infotainment system of the vehicle alerting the driver about the emergency at 204. In an embodiment of the system, the alert signal comprises at least one of a text message, a display, a sound, a light, and a combination thereof. The method then automatically turns on, by the processor, an emergency indication light, wherein the emergency indication light is visible to a nearby vehicle at 206. The method then automatically generates a path from the current location of the vehicle to a target location at 208. The method then aids the driver to maneuver the vehicle along the path to the target location at 210. While the driver is maneuvering, the method automatically identifies, by the processor, a medical facility based upon a location of the vehicle at 212. The method automatically contacts an emergency service and provides the location of the vehicle and a health condition of the passenger of the vehicle at 214; and the method automatically transmits a medical record of the passenger of the vehicle to the medical facility at 216. An embodiment relates to a method comprising: automatically detecting, by the processor using a signal from the sensor, that a passenger of a vehicle is experiencing a medical emergency; automatically generating of an alert signal on an infotainment system of the vehicle; automatically turning on, by the processor, an emergency indication light, wherein the emergency indication light is visible to a nearby vehicle; automatically generating a path from the current location of the vehicle to a target location; maneuvering, the vehicle along the path to the target location; automatically identifying, by the processor, a medical facility based upon a location of the vehicle; automatically contacting, by the processor via a communication module, an emergency service and providing the location of the vehicle and a health condition of the passenger of the vehicle; and automatically providing, by the processor via a communication module, a medical record of the passenger of the vehicle to the medical facility.

Figure 2B:
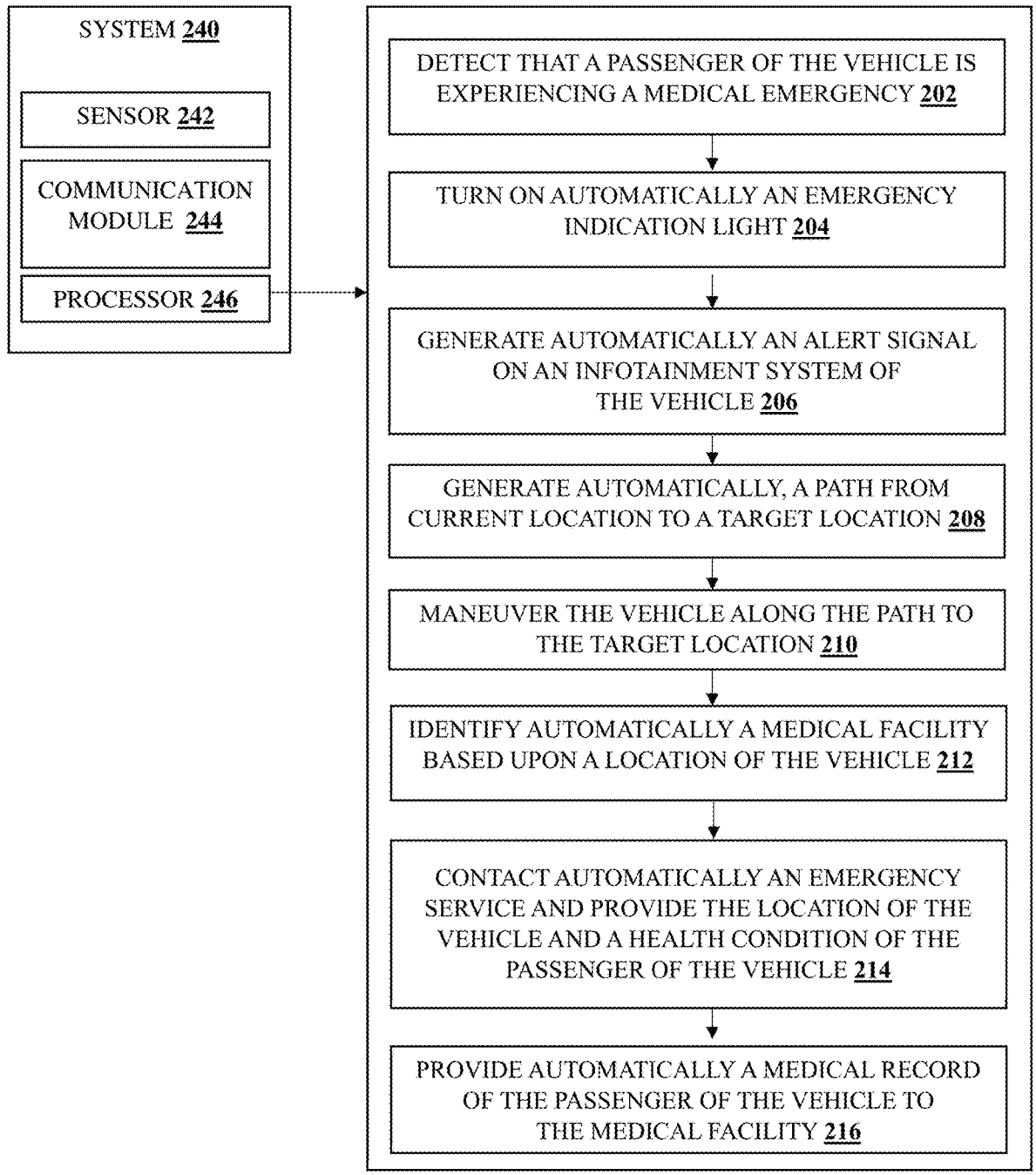
FIG. 2B shows steps executed by a system of a vehicle for monitoring and detecting the health emergency of the passenger of the vehicle and assisting in the emergency situation according to an embodiment.

FIG. 2B shows steps executed by a system of a vehicle for monitoring and detecting the health emergency of the passenger of the vehicle and assisting in the emergency situation according to an embodiment. An embodiment relates to a system 240, comprising: a sensor 242; a communication module 244; and a processor 246; wherein the processor 246 performs, under power, following functions, wherein the functions comprise: automatic detection, by the processor using a signal from the sensor that a passenger of a vehicle is experiencing a medical emergency as shown at 202; automatic generation of an alert signal on an infotainment system of the vehicle as shown at 204; automatic turn on, by the processor, an emergency indication light, wherein the emergency indication light is visible to a nearby vehicle as shown at 206; automatic generation of a path from the current location of the vehicle to a target location as shown at 208; maneuver, the vehicle along the path to the target location as shown at 210; automatic identification, by the processor, of a medical facility based upon a location of the vehicle as shown at 212; automatic contact, by the processor via a communication module, to an emergency service and providing the location of the vehicle and a health condition of the passenger of the vehicle as shown at 214; and automatic transmission, by the processor via a communication module, of a medical record of the passenger of the vehicle to the medical facility as shown at 216. According to an embodiment, the system is configured to be a component of a vehicle.

In an embodiment of the system, the processor further comprises an artificial intelligence algorithm. In an embodiment of the system, the sensor comprises at least one of a temperature sensor, a heart rate sensor, a respiration sensor, a blood pressure sensor, and a perspiration sensor. In an embodiment of the system, the health condition of the passenger is due to at least one of a choking, a fever, a change in vital signs indicating a problem in physiological function of the passenger.

In an embodiment of the system, the target location is a pull over location. In an embodiment of the system, the target location is a location of the medical facility. In an embodiment of the system, the maneuver of the vehicle to the pull over location is by a driver of the vehicle. In an embodiment of the system, the maneuver of the vehicle to the pull over location is by instructing a driver of the vehicle with at least one of a voice instruction or by displaying the instruction on a display of the vehicle. In an embodiment of the system, the maneuver of the vehicle to the pull over location is in an autonomous mode of the vehicle. In an embodiment of the system, the processor is at least one of an in-vehicle processor and an application server on a cloud. In an embodiment of the system, data from the sensor is stored to a database. In an embodiment of the system, the database is a cloud database.

Figure 2C:
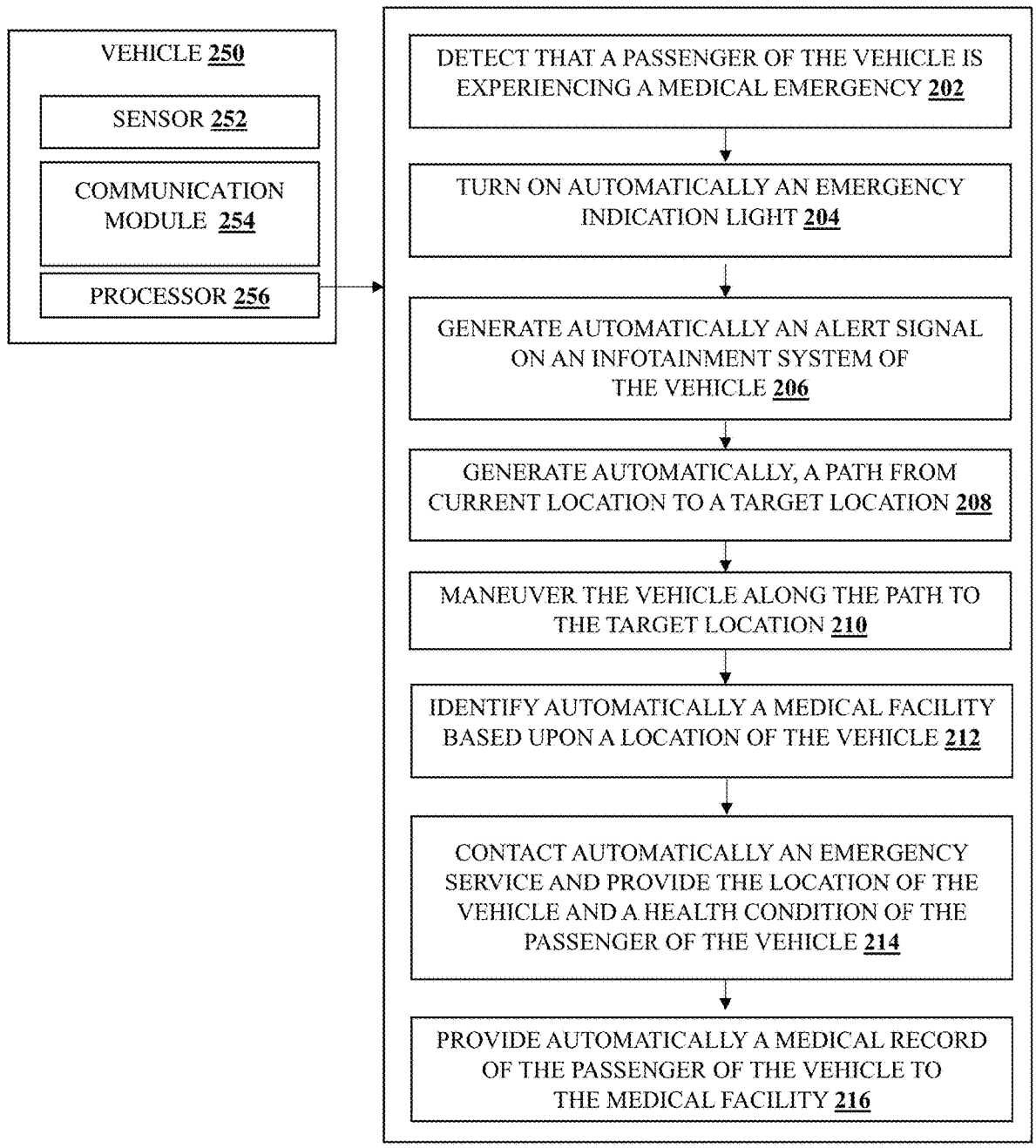
FIG. 2C shows steps executed by a system of a vehicle for monitoring and detecting the health emergency of the passenger of the vehicle and assisting in the emergency situation according to an embodiment.

FIG. 2C shows steps executed by a vehicle of a vehicle for monitoring and detecting the health emergency of the passenger of the vehicle and assisting in the emergency situation according to an embodiment. Another embodiment relates to a vehicle 250, comprising: a sensor 252; a communication module 254; and a processor 256; wherein the processor 256 performs, under power, the following functions, wherein the functions comprise: automatic detection, by the processor using a signal from the sensor, that a passenger of a vehicle is experiencing a medical emergency as shown at 202; automatic generation of an alert signal on an infotainment system of the vehicle as shown at 204; automatic turning on, by the processor, an emergency indication light, wherein the emergency indication light is visible to a nearby vehicle as shown at 206; automatic generation of a path from the current location of the vehicle to a target location as shown at 208;

maneuver, the vehicle along the path to the target location as shown at 210; automatic identification, by the processor, of a medical facility based upon a location of the vehicle as shown at 212; automatic contact, by the processor via a communication module, to an emergency service and providing the location of the vehicle and a health condition of the passenger of the vehicle as shown at 214; and automatic transmission, by the processor via a communication module, of a medical record of the passenger of the vehicle to the medical facility as shown at 216.

Figure 2D:
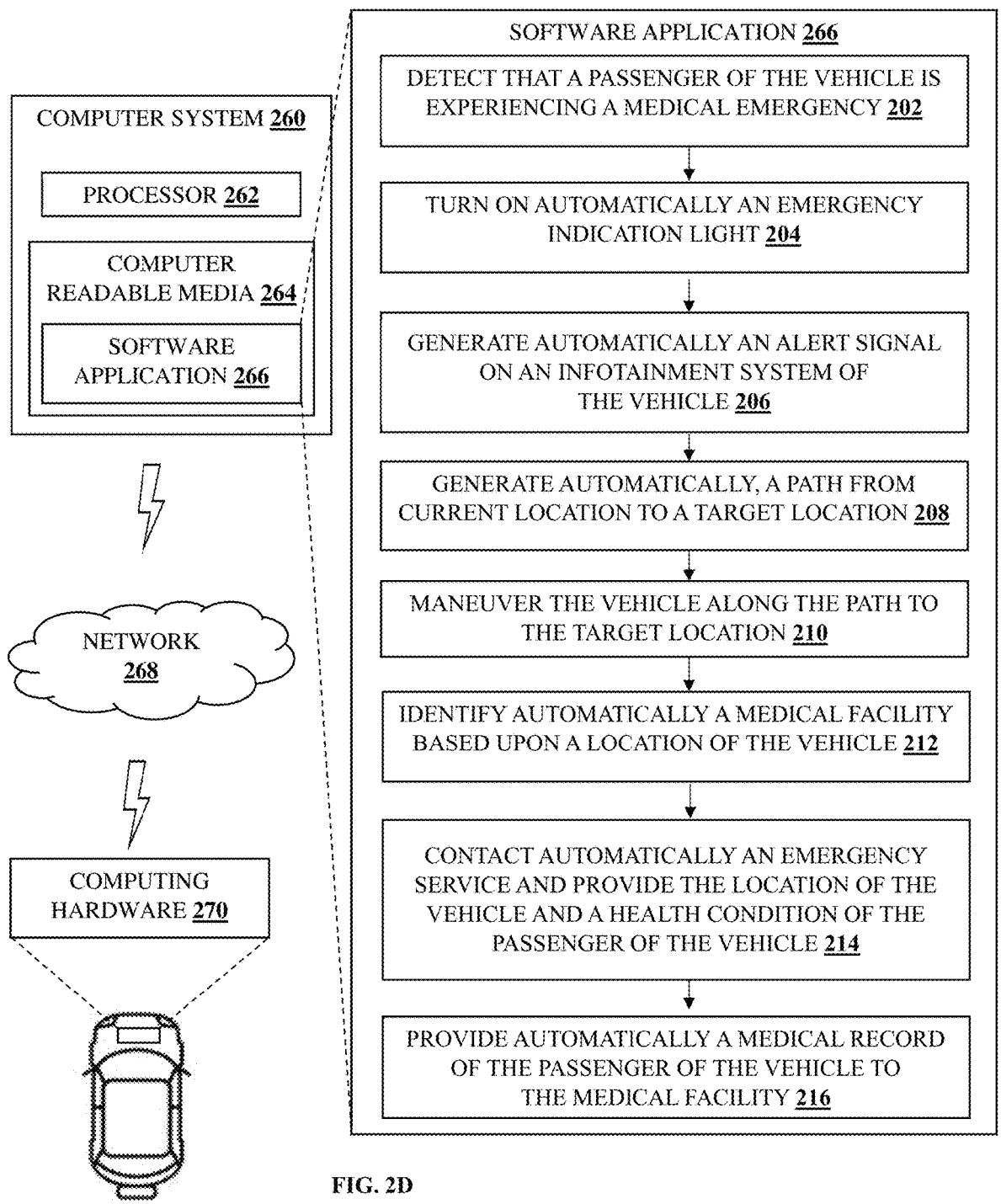
FIG. 2D shows steps executed for installation of instructions in a vehicle computing hardware for monitoring and detecting the health emergency of the passenger of the vehicle and assisting in the emergency situation according to an embodiment.

FIG. 2D shows steps executed for installation of instructions in a vehicle computing hardware for monitoring and detecting the health emergency of the passenger of the vehicle and assisting in the emergency situation according to an embodiment. Another embodiment relates to a system 260, wherein the system is configured to receive a software installation package over a computer network; and install the software application 266 onto a computing hardware 270 associated with a vehicle, wherein the software application 266 comprises: set of instructions executable by the computing hardware 270 and stored in a computer readable media 264 wherein the computer readable media 264 is a non-transitory storage medium that, when executed, cause the computing hardware 270 to implement operations by a vehicle comprising, detecting, by the processor using a signal from the sensor, that a passenger of the vehicle is experiencing a medical emergency as shown at 202; automatically generating of an alert signal on an infotainment system of the vehicle as shown at 204; automatically turning on, by the processor, an emergency indication light, wherein the emergency indication light is visible to a nearby vehicle as shown at 206; automatically generating a path from the current location of the vehicle to a target location as shown at 208; maneuver, the vehicle along the path to the target location as shown at 210; automatically identifying, by the processor, a medical facility based upon a location of the vehicle as shown at 212; automatically contacting, by the processor via a communication module, an emergency service and providing the location of the vehicle and a health condition of the passenger of the vehicle as shown at 214; and automatically transmitting, by the processor via a communication module, a medical record of the passenger of the vehicle to the medical facility as shown at 216. The system comprises a processor 262 to execute the set of instructions stored in a memory.

Figure 2E:
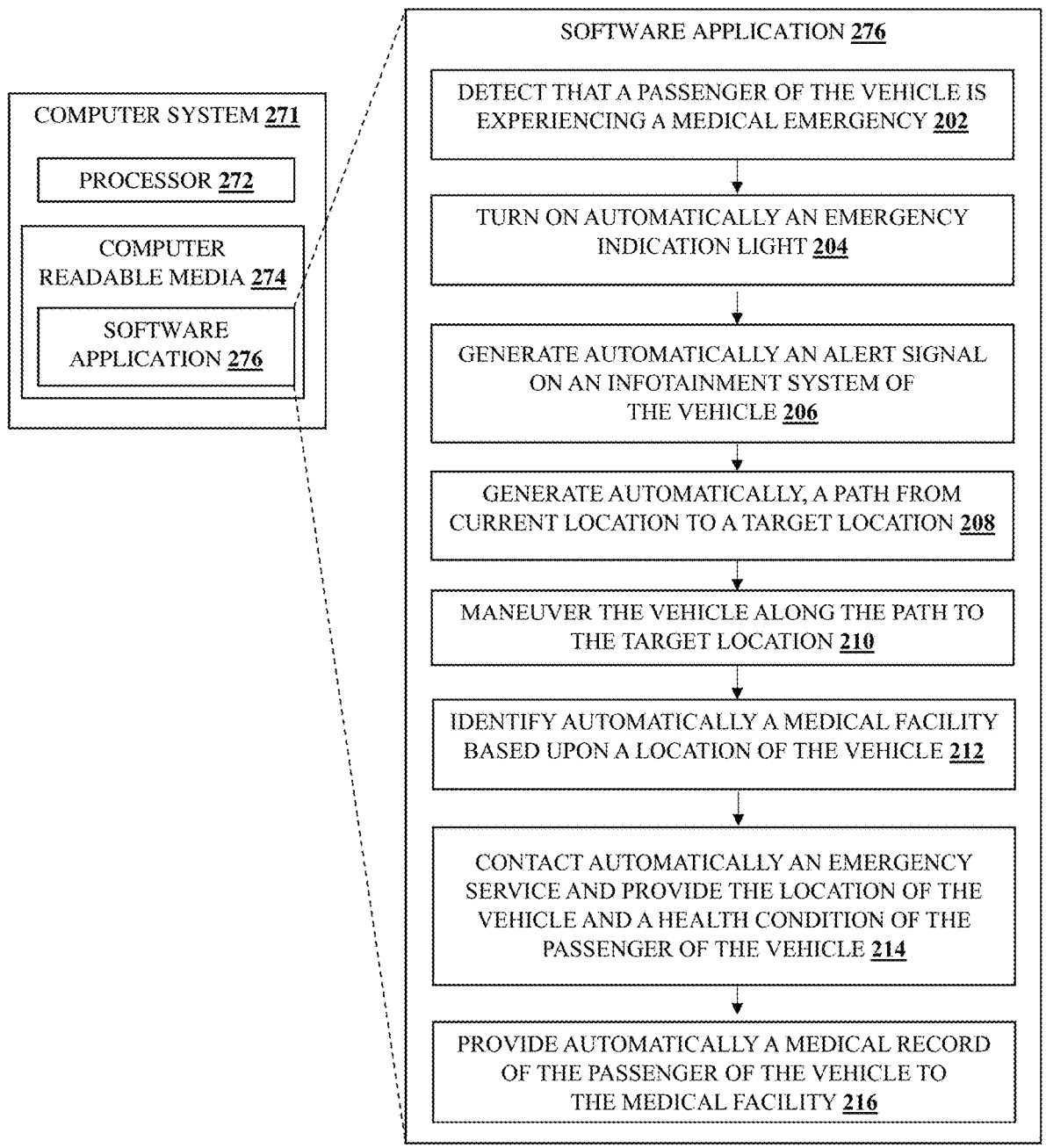
FIG. 2E shows steps executed by a computer readable media for monitoring and detecting the health emergency of the passenger of the vehicle and assisting in the emergency situation according to an embodiment.

FIG. 2E shows steps executed by a computer readable media for monitoring and detecting the health emergency of the passenger of the vehicle and assisting in the emergency situation according to an embodiment. Another embodiment relates to a computer readable media 274 which is a non-transitory computer-readable medium having stored thereon instructions executable by a processor 272 of a computer system 271 to perform operations comprising: automatically detecting, by the processor using a signal from the sensor, that a passenger of a vehicle is experiencing a medical emergency as shown at 202; automatically generating of an alert signal on an infotainment system of the vehicle as shown at 204; automatically turning on, by the processor, an emergency indication light, wherein the emergency indication light is visible to a nearby vehicle as shown at 206; automatically generating a path from the current location of the vehicle to a target location as shown at 208; maneuvering, the vehicle along the path to the target location as shown at 210; automatically identifying, by the processor, a medical facility based upon a location of the vehicle as shown at 212; automatically contacting, by the processor via a communication module, an emergency service and providing the location of the vehicle and a health condition of the passenger of the vehicle as shown at 214; and automatically providing, by the processor via a communication module, a medical record of the passenger of the vehicle to the medical facility as shown at 216. Instructions executable by the processor 272 may be in the form of a software application 276.

Figure 2F:
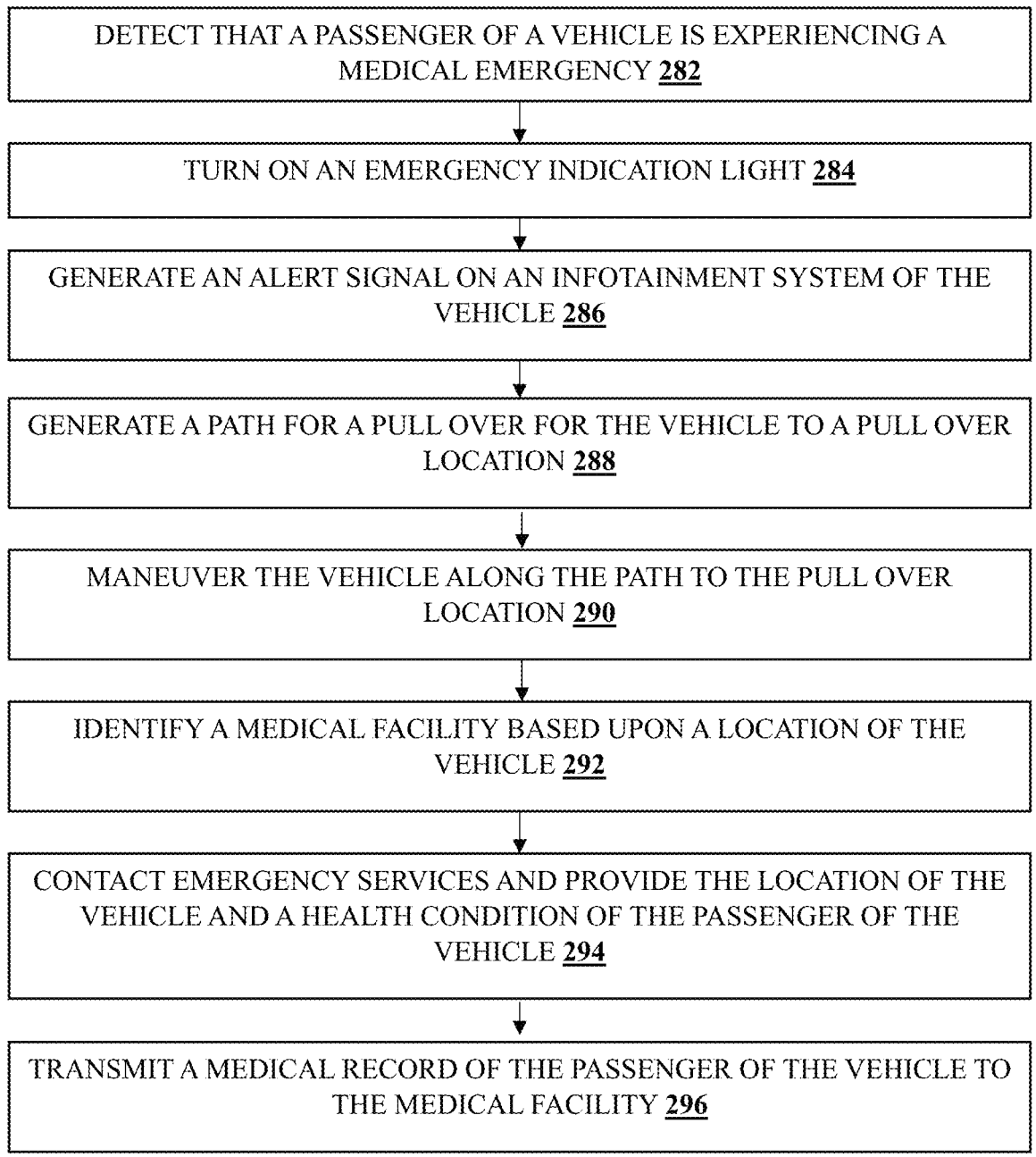
FIG. 2F shows a flowchart for a method for monitoring and detecting the health emergency of the passenger of the vehicle and assisting in pull over according to an embodiment.

FIG. 2F shows a flowchart for a method 280 for monitoring and detecting the health emergency of the passenger of the vehicle and assisting in pull over according to an embodiment. An embodiment relates to a method 280, comprising: automatically detecting, by the processor using a signal from the sensor, that a passenger of a vehicle is experiencing a medical emergency as shown at 282; automatically turning on, by the processor, an emergency indication light as shown at 284; automatically generating, an alert signal on an infotainment system indicating a need for a pull over of the vehicle as shown at 286; automatically generating, a path for the pull over for the vehicle to a pull over location as shown at 288; maneuver, the vehicle along the path to the pull over location as shown at 290; automatically identifying, by the processor, a medical facility based upon a location of the vehicle as shown at 292; automatically contacting, by the processor via a communication module, an emergency service and providing the location of the vehicle and a health condition of the passenger of the vehicle as shown at 294; and automatically transmitting, by the processor via a communication module, a medical record of the passenger of the vehicle to the medical facility as shown at 296.

Figure 3A:
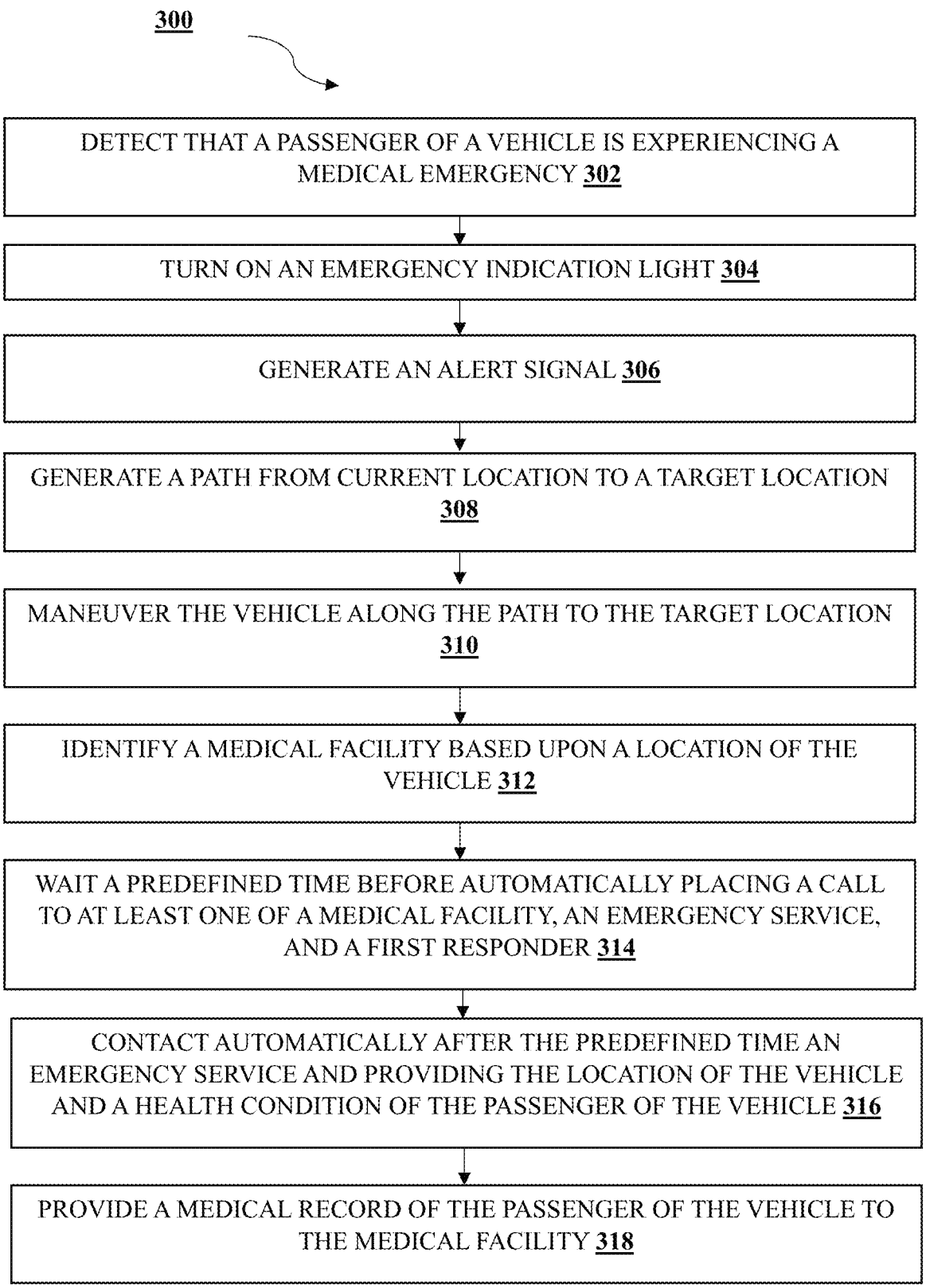
FIG. 3A shows a flowchart for a method for monitoring the health emergency of the passenger of the vehicle and assisting in the emergency situation where the system waits a predefined time before automatically making decisions according to an embodiment.

FIG. 3A shows a flowchart for a method for monitoring the health emergency of the passenger of the vehicle and assisting in the emergency situation where the system waits a predefined time before automatically making decisions according to an embodiment. In an embodiment, method 300, comprises: automatically detecting that a passenger of a vehicle is experiencing a medical emergency at 302. The system then automatically turns on an emergency indication light on an infotainment system of the vehicle at 304. In an embodiment, it could be a hazard signal. Method 300 further automatically generates an alert signal at 306, automatically generates a path from the current location to a target location at 308; the method 300 assists the driver to maneuver the vehicle along the path to the target location 310. While the driver is trying to maneuver the vehicle, the method 300 automatically identifies, by the processor, a medical facility based upon a location of the vehicle at 312. The system would be waiting a predefined time, before automatically placing a call to at least one of a medical facility, an emergency service, and a first responder at 314. The predefined time may be based on a preset time limit or based on past experience of such a medical situation. Then the system would automatically be contacting, after the predefined time, an emergency service and providing the location of the vehicle and a health condition of the passenger of the vehicle at 316 and automatically transmitting a medical record of the passenger of the vehicle to the medical facility at 318. The medical record of the passenger can be accessed from an electronic health record system and may be asked by the system to directly share with at least one of a medical facility, an emergency service, and a first responder.

According to an embodiment it is a method, comprising, automatically detecting, by the processor using a signal from the sensor, that a passenger of a vehicle is experiencing a medical emergency; automatically turning on, by the processor, an emergency indication light; automatically generating, an alert signal on an infotainment system of the vehicle; automatically generating, a path from current location of the vehicle to a target location; maneuvering, the vehicle along the path to the target location; automatically identifying, by the processor, a medical facility based upon a location of the vehicle; waiting a predefined time, by the processor, before automatically placing a call to at least one of a medical facility, an emergency service, and a first responder; automatically contacting, after the predefined time by the processor via a communication module, an emergency service and providing the location of the vehicle and a health condition of the passenger of the vehicle; and automatically transmitting, by the processor via a communication module, a medical record of the passenger of the vehicle to the medical facility.

According to an embodiment it is a system, comprising: a sensor; a communication module; and a processor; wherein the processor performs, under power, following functions, wherein the functions comprise: automatic detection, by the processor using a signal from the sensor, that a passenger of a vehicle is experiencing a medical emergency; automatic turning on, by the processor, an emergency indication light on an infotainment system of the vehicle; automatic generation, an alert signal; automatic generation, a path from the current location to a target location; maneuver, the vehicle along the path to the target location; automatic identification, by the processor, of a medical facility based upon a location of the vehicle; waiting a predefined time, by the processor, before automatically placing a call to at least one of a medical facility, an emergency service, and a first responder; automatic contacting, after the predefined time by the processor via a communication module, an emergency service and providing the location of the vehicle and a health condition of the passenger of the vehicle; and automatic transmission, by the processor via a communication module, of a medical record of the passenger of the vehicle to the medical facility. According to an embodiment, the system is configured to be a component of the vehicle. In an embodiment of the system, the system detects based on a second sensor associated with the vehicle, the nearby vehicle. In an embodiment of the system, the second sensor comprises at least one of an infrared sensor, an ultrasonic sensor, a radar sensor, a passive acoustic detector array, a piezoelectric sensor, a photoelectric sensor and an image sensor. In an embodiment of the system, wherein a required speed of the nearby vehicle is estimated using its dedicated short range communication by obtaining a distance between the vehicle and the nearby vehicle. In an embodiment of the system, the nearby vehicle is in proximity and within a communication range of the vehicle. In an embodiment of the system, the nearby vehicle comprises at least one of a car, a truck, a van, a motorcycle, a bus, a trailer, and a construction vehicle. In an embodiment of the system, the vehicle senses the speed of the nearby vehicle for determining the path to the target location, and transmits a message with an instruction for speed, and an instruction for course to the nearby vehicle.

In an embodiment of the system, the system simultaneously identifies the medical facility and contacts the emergency service while the driver attempts to pull over the vehicle. In an embodiment of the system, the system continuously monitors the passenger.

In an embodiment of the system, the vehicle further comprises a camera and an image processor. In an embodiment of the system, the camera is configured to capture an image of a passenger. In an embodiment of the system, the camera is configured to capture an image of the driver. In an embodiment of the system, the camera comprises a plurality of cameras, wherein a first camera monitors the passenger, and a second camera monitors the driver. In an embodiment of the system, the pull over decision is made based on the passenger health data and the driver health data.

Figure 3B:
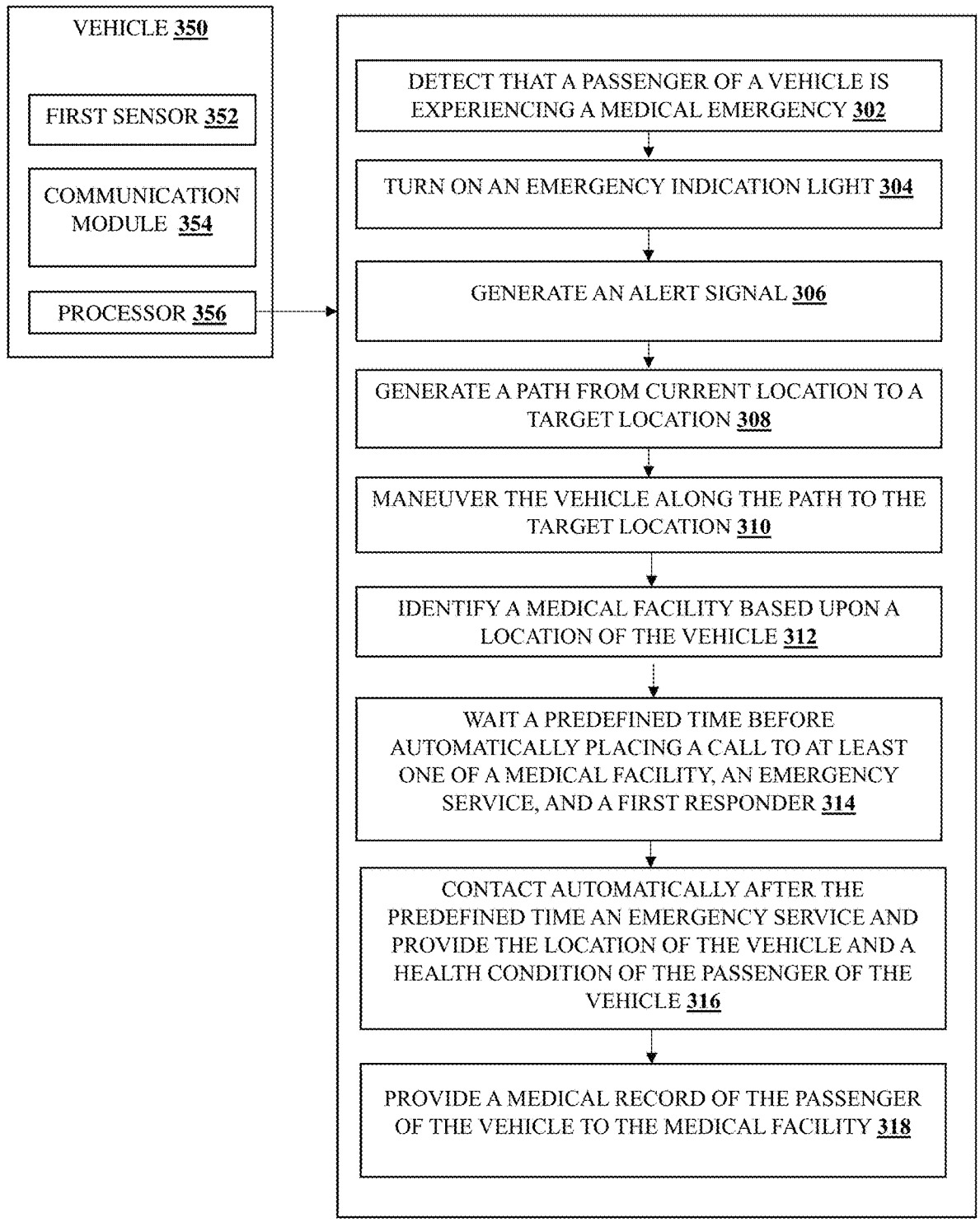
FIG. 3B shows steps executed by a vehicle for monitoring the health emergency of the passenger of the vehicle and assisting in the emergency situation where the system waits a predefined time before automatically making decisions according to an embodiment.

FIG. 3B shows steps executed by a vehicle 350 for monitoring the health emergency of the passenger of the vehicle and assisting in the emergency situation where the system waits a predefined time before automatically making decisions according to an embodiment. A vehicle 350, comprising: a sensor 352; a communication module 354; and a processor 356; wherein the processor 356 performs, under power, the following functions, wherein the functions comprise: automatic detection, by the processor using a signal from the sensor, that a passenger of the vehicle is experiencing a medical emergency as shown at 302; automatic turning on, by the processor, an emergency indication light as shown at 304; automatic generation, an alert signal on an infotainment system of the vehicle as shown at 306; automatic generation, a path from the current location to a target location as shown at 308; maneuver, the vehicle along the path to the target location as shown at 310; automatic identification, by the processor, of a medical facility based upon a location of the vehicle as shown at 312; waiting a predefined time, by the processor, before automatically placing a call to at least one of a medical facility, an emergency service, and a first responder as shown at 314; automatic contacting, after the predefined time by the processor via a communication module, an emergency service and providing the location of the vehicle and a health condition of the passenger of the vehicle as shown at 316; and automatic transmission, by the processor via a communication module, of a medical record of the passenger of the vehicle to the medical facility as shown at 318. In an embodiment of the system, the vehicle is a car. In an embodiment of the system, the communication module is enabled for at least one of a vehicle-to-vehicle communication, vehicle-to-infrastructure communication, and vehicle-to-everything communication. In an embodiment of the system, the vehicle-to-vehicle communication comprises dedicated short range communication.

In an embodiment of the system, the passenger is a child in a rear facing seat.

A system configured to receive a software application installation package over a computer network; and install the software application onto the computing hardware associated with a vehicle; wherein the software application comprises: set of instructions executable by a computing hardware and stored in a non-transitory storage medium that, when executed, cause the computing hardware to implement operations comprising, automatically detecting, by the processor using a signal from the sensor, that a passenger of a vehicle is experiencing a medical emergency; automatically turning on, by the processor, an emergency indication light; automatically generating, an alert signal on an infotainment system of the vehicle; automatically generating, a path from current location of the vehicle to a target location; maneuvering, the vehicle along the path to the target location; automatically identifying, by the processor, a medical facility based upon a location of the vehicle; waiting a predefined time, by the processor, before automatically placing a call to at least one of a medical facility, an emergency service, and a first responder; automatically contacting, after the predefined time by the processor via a communication module, an emergency service and providing the location of the vehicle and a health condition of the passenger of the vehicle; and automatically transmitting, by the processor via a communication module, a medical record of the passenger of the vehicle to the medical facility.

A non-transitory computer-readable medium having stored thereon instructions executable by a computer system to perform operations comprising: automatically detecting, by the processor using a signal from the sensor, that a passenger of a vehicle is experiencing a medical emergency; automatically turning on, by the processor, an emergency indication light on an infotainment system of the vehicle; automatically generating, an alert signal; automatically generating, a path from current location of the vehicle to a target location; maneuvering, the vehicle along the path to the target location; automatically identifying, by the processor, a medical facility based upon a location of the vehicle; waiting a predefined time, by the processor, before automatically placing a call to at least one of a medical facility, an emergency service, and a first responder; automatically contacting, after the predefined time by the processor via a communication module, an emergency service and providing the location of the vehicle and a health condition of the passenger of the vehicle; and automatically transmitting, by the processor via a communication module, a medical record of the passenger of the vehicle to the medical facility.

Figure 3C:
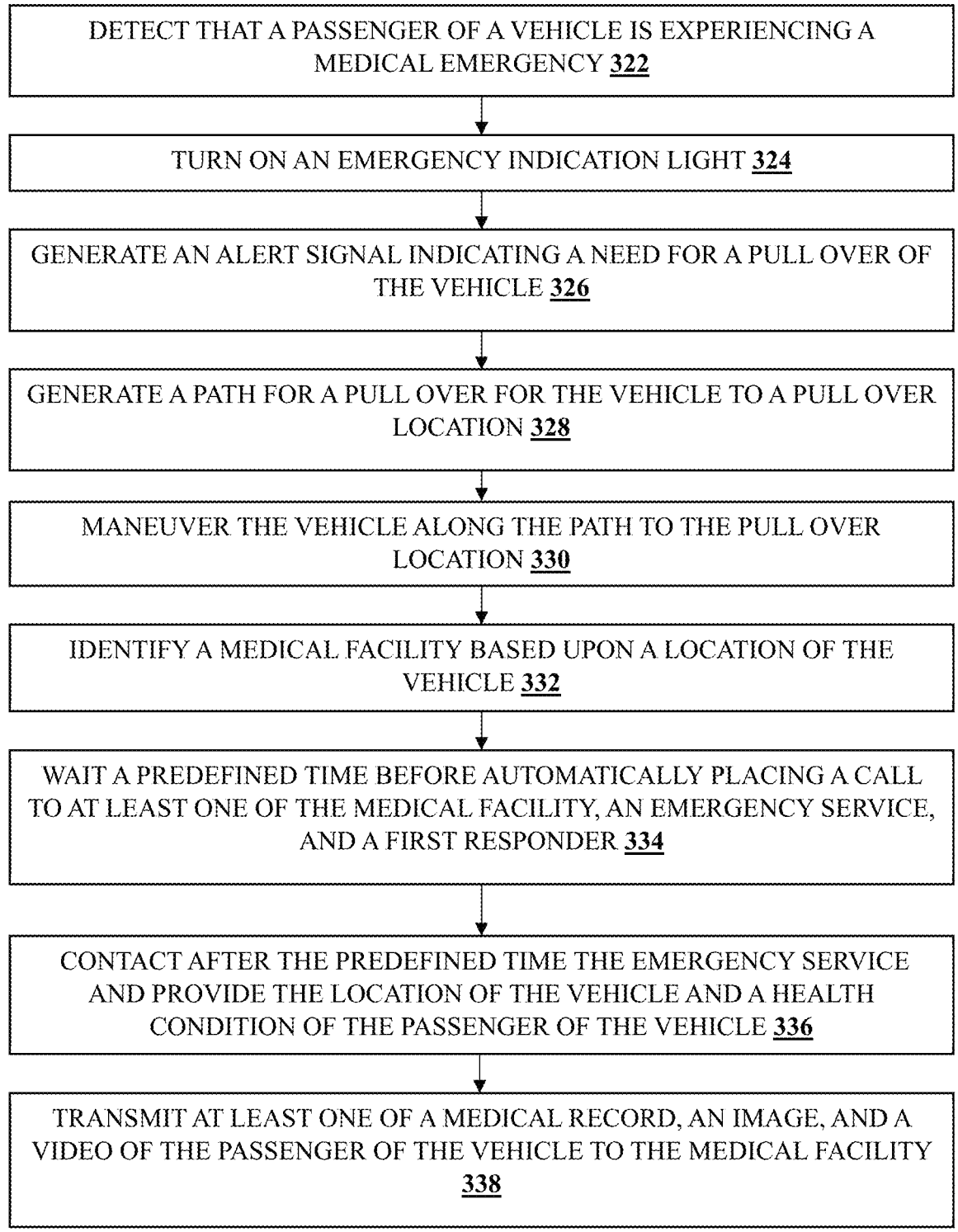
FIG. 3C shows a flowchart for a method for monitoring the health emergency of the passenger of the vehicle and assisting in the emergency situation where the system transmits information to a medical facility according to an embodiment.

FIG. 3C shows a flowchart for a method for monitoring the health emergency of the passenger of the vehicle and assisting in the emergency situation where the system transmits information to a medical facility according to an embodiment. An embodiment related to a method, comprising: automatically detecting, by the processor using a signal from the sensor, that a passenger of a vehicle is experiencing a medical emergency as shown at 322; automatically turning on, by the processor, an emergency indication light as shown at 324; automatically generating, an alert signal indicating a need for a pull over of the vehicle as shown at 326; automatically generating, a path for the pull over for the vehicle to a pull over location as shown at 328; maneuvering, the vehicle along the path to the pull over location as shown at 330; automatically identifying, by the processor, a medical facility based upon a location of the vehicle as shown at 332; waiting a predefined time, by the processor, before automatically placing a call to at least one of a medical facility, an emergency service, and a first responder as shown at 334; automatically contacting, after the predefined time by the processor via a communication module, an emergency service and providing the location of the vehicle and a health condition of the passenger of the vehicle as shown at 336; and automatically transmitting, by the processor via a communication module, a medical record of the passenger of the vehicle to the medical facility; and automatically transmitting, by the processor via a communication module, at least one of an image, and a video of the passenger of the vehicle to the medical facility as shown at 338.

Figure 3D:
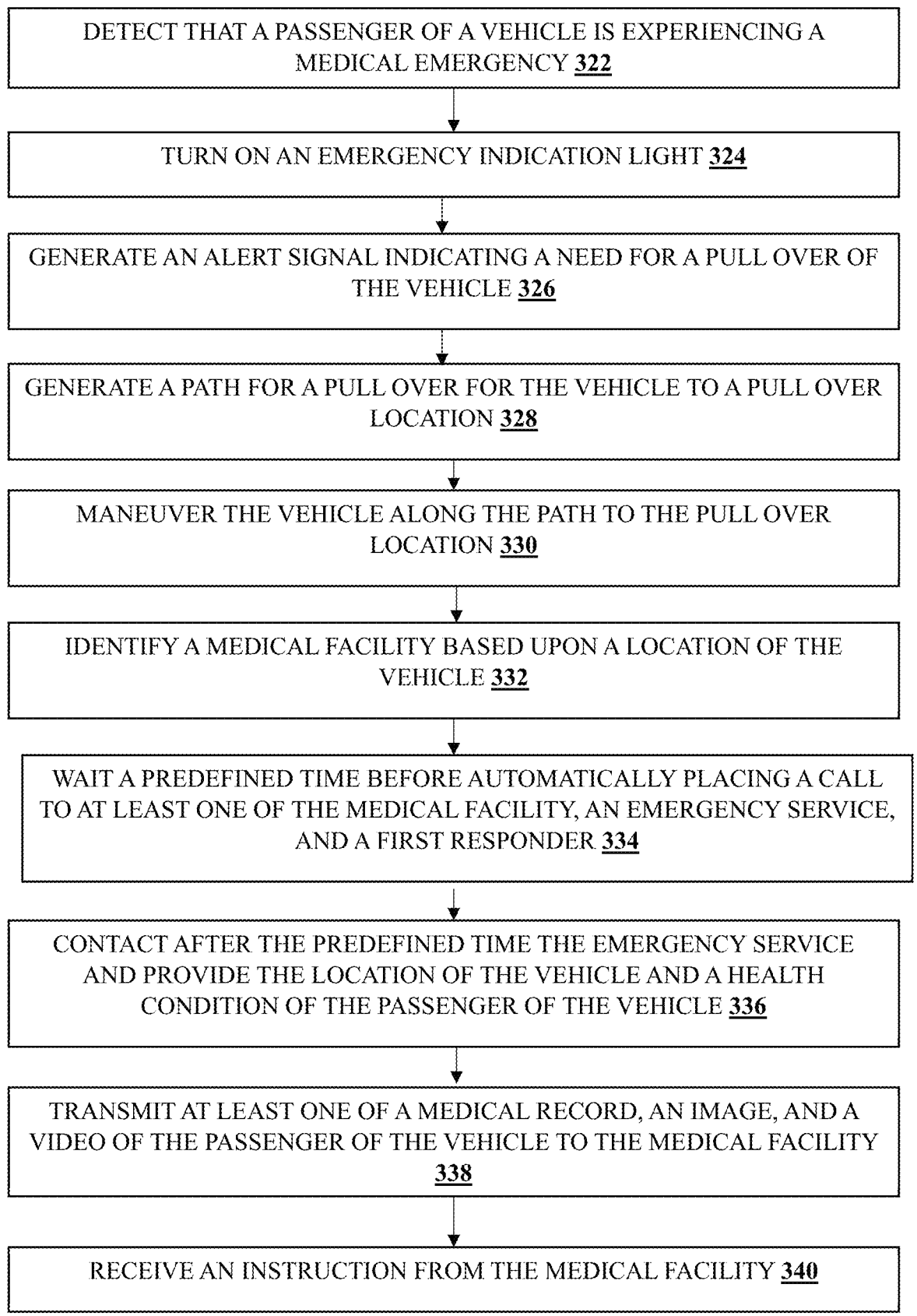
FIG. 3D shows a flowchart for a method for monitoring the health emergency of the passenger of the vehicle and assisting in the emergency situation where the system receives instruction from medical facility according to an embodiment.

FIG. 3D shows a flowchart for a method for monitoring the health emergency of the passenger of the vehicle and assisting in the emergency situation where the system receives instruction from medical facility according to an embodiment. An embodiment related to a method, comprising: automatically detecting, by the processor using a signal from the sensor, that a passenger of a vehicle is experiencing a medical emergency as shown at 322; automatically turning on, by the processor, an emergency indication light as shown at 324; automatically generating, an alert signal indicating a need for a pull over of the vehicle as shown at 326; automatically generating, a path for the pull over for the vehicle to a pull over location as shown at 328; maneuvering, the vehicle along the path to the pull over location as shown at 330; automatically identifying, by the processor, a medical facility based upon a location of the vehicle as shown at 332; waiting a predefined time, by the processor, before automatically placing a call to at least one of a medical facility, an emergency service, and a first responder as shown at 334; automatically contacting, after the predefined time by the processor via a communication module, an emergency service and providing the location of the vehicle and a health condition of the passenger of the vehicle as shown at 336; and automatically transmitting, by the processor via a communication module, at least one of a medical record, an image, and a video of the passenger of the vehicle to the medical facility as shown at 338; and receiving an instruction from the medical facility as shown at 340.

Figure 4A:
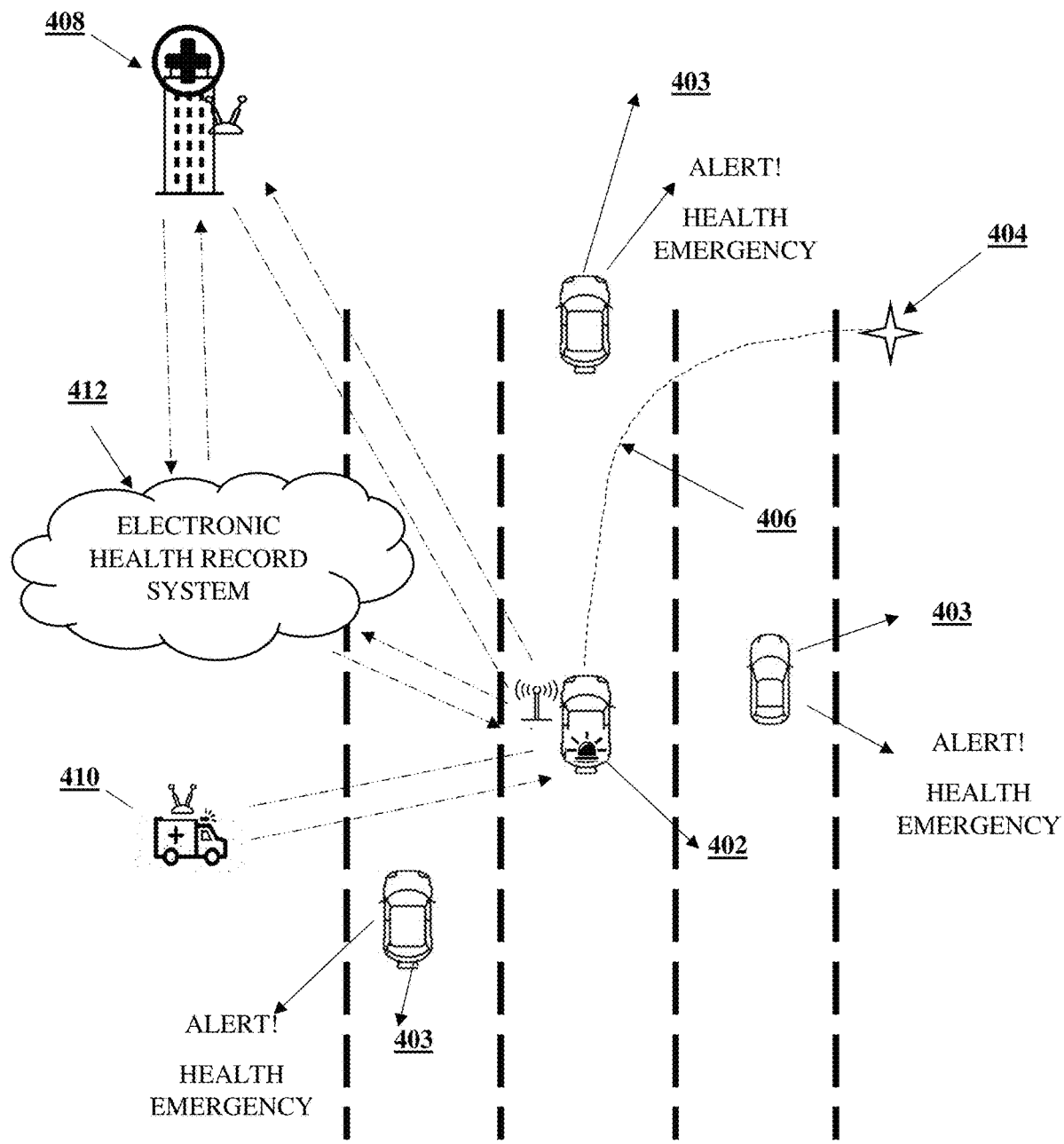
FIG. 4A shows the system assisting in an emergency situation according to an embodiment.

FIG. 4A shows the system assisting in an emergency situation according to an embodiment. In an embodiment, the system 400 will automatically turn on a hazard signal. Based on traffic conditions, reduce speed to allow the driver to pull over to a safe location. Based on a health alert, suggest nearest urgent care or a medical facility that can assist. Based on the health alert, automatically contact emergency services (911), and provide the location and health condition of the child or the passenger. Access all medical records and provide them to medical professionals. In an embodiment, the user would have to previously provide authorization. In an embodiment, the system detects that there is a medical issue with a child in the vehicle seat, for example, the child is choking. Then immediately, the system recognizes that a medical emergency is happening, and determines the next steps. For example, if the user's vehicle 402 is going at 40 miles per hour on a freeway and the child in the vehicle seat is choking. The driver still needs to focus on driving and cannot safely attend to the child. The infotainment system will recognize that a medical emergency is happening, it will alert the driver, display the message, and the system can automatically use a camera that is pointed to the driver itself, and with the help of artificial intelligence (AI) would process the image using image processing algorithms, and detect that the driver itself is in distress because of the health issue of the child. The driver may want to pull over to the side to a pull over location as 404 along a path 406 and check on the child, since the driver may not be able to attend to the child while driving. The pull over path 406 would have been determined by the system and would be guiding the driver along that path. In an embodiment of the system, the path comprises a plurality of phases which comprise a pre-maneuver phase, a maneuver phase, and a post-maneuver phase. In an embodiment of the system, each phase of the plurality of phases comprises a speed profile, a direction profile, and a braking profile. In an embodiment of the system, the path is displayed on the infotainment system of the vehicle. In an embodiment of the system, the speed profile, the direction profile, and the braking profile of the plurality of phases are displayed on the infotainment system of the vehicle. The system will assist the driver by automatically turning on the hazard signal, so the user does not have to do this manually. The system automatically switches on the hazard signal as soon as it detects an emergency. Once the hazard signal is switched on, based on traffic conditions, the vehicle would help manage the traffic speeds by communicating with the nearby vehicles 403 and let the user's vehicle reduce the speed, manage the traffic, and allow the driver to pull over safely. In an embodiment, if a health emergency is happening, the system would automatically slow down the vehicle and may be enter into an autonomous mode. Further, based on the type of health alert and severity, the system can identify the nearest medical facility or emergency facility 408. In an embodiment, the nearest medical facility may be in terms of distance, time, or a facility where the passenger can be attended to. The system would then notify the nearest urgent care or medical facility that can assist. The system may automatically make a connection, and make a call, while the driver is trying to pull over. In an embodiment, the system would, automatically, switch on the signals, slow down the vehicle, make a call to emergency services 410 based on the severity and type of the emergency. If the health alert is low oxygen level, or where one can wait for a while, the system may wait before it decides to make a call to the emergency care immediately. For example, based on the health alert, if a child stopped breathing, or child is not moving, then the driver will get the notification. If the driver has to get out, pull over, look, and shake the child, it will cause unnecessary delay in attending to the child. In some cases, the detection of a health emergency with the child may itself take time adding more trouble. Therefore, the system will automatically detect a health emergency, and based on the health alert would automatically assist the driver in pulling over and simultaneously make a call to emergency care and emergency services while the driver is pulling the vehicle over or attending to the child. In an embodiment, the notification of an emergency to the driver would comprise a video or an image of the child on the infotainment system, so that the driver need not turn back and check on the child.

In an embodiment, the system would access medical records and share them with the medical care personnel via the communication link between the vehicle and the medical facility. In an embodiment, the system would ask the electronic health record system to directly share the medical record with the emergency care facility. The system may further identify and suggest the closest emergency services and guide the driver to go to the emergency care facility instead of pulling over. The system may help the vehicle slow down by instructing the driver or would slow down the vehicle automatically to help driver get to emergency care. Further, if the situation either worsens or does not improve, then the system may automatically place a call to emergency services, say for example 911. In an embodiment, the driver can use a voice instruction and ask the system for placing a call to the emergency services. In an embodiment, the system would call the 911 operator, and then provide all the information, including health records to the operator. In another embodiment, the system may even provide the camera views or videos to the 911 operator or any medical first responders so that they can actually see what is happening before they get to the location of emergency.

In an embodiment, once the system assists the driver in pulling over safely, the system waits for a predefined amount of time. If the situation continues to worsen, or nothing changes in a given time, for example, the baby is choking, and, for example, say after 10 seconds, 30 seconds, or a minute, the system will start to take procedural aspects. Firstly, contact the local emergency and provide information that there is an emergency and notify them that the driver will be arriving with the child.

In an embodiment, a satellite-based assistance system is available for help during an emergency. The system is available onboard to assist upon subscription. In an embodiment, upon subscription to the system, when the driver manually hits the button, or enabled by voice message via artificial intelligence using a natural language processing algorithm, then automatic connections can be made to the emergency services.

In an embodiment, the system would allow the driver to focus on getting the vehicle off the road, or to the urgent care and at the same time, continue monitoring, and then decide whether a 911 call is necessary. For example, if the child's oxygen rate just went down, the system may decide to call emergency services 911, and if the seat belt is loose or it is just the heat that is making the child uncomfortable then the system may decide not to call emergency services (e.g., 911). The system continues to monitor and if the camera detects that the child is turning blue, then it will connect to 911 and provide the emergency situation.

Figure 4B:
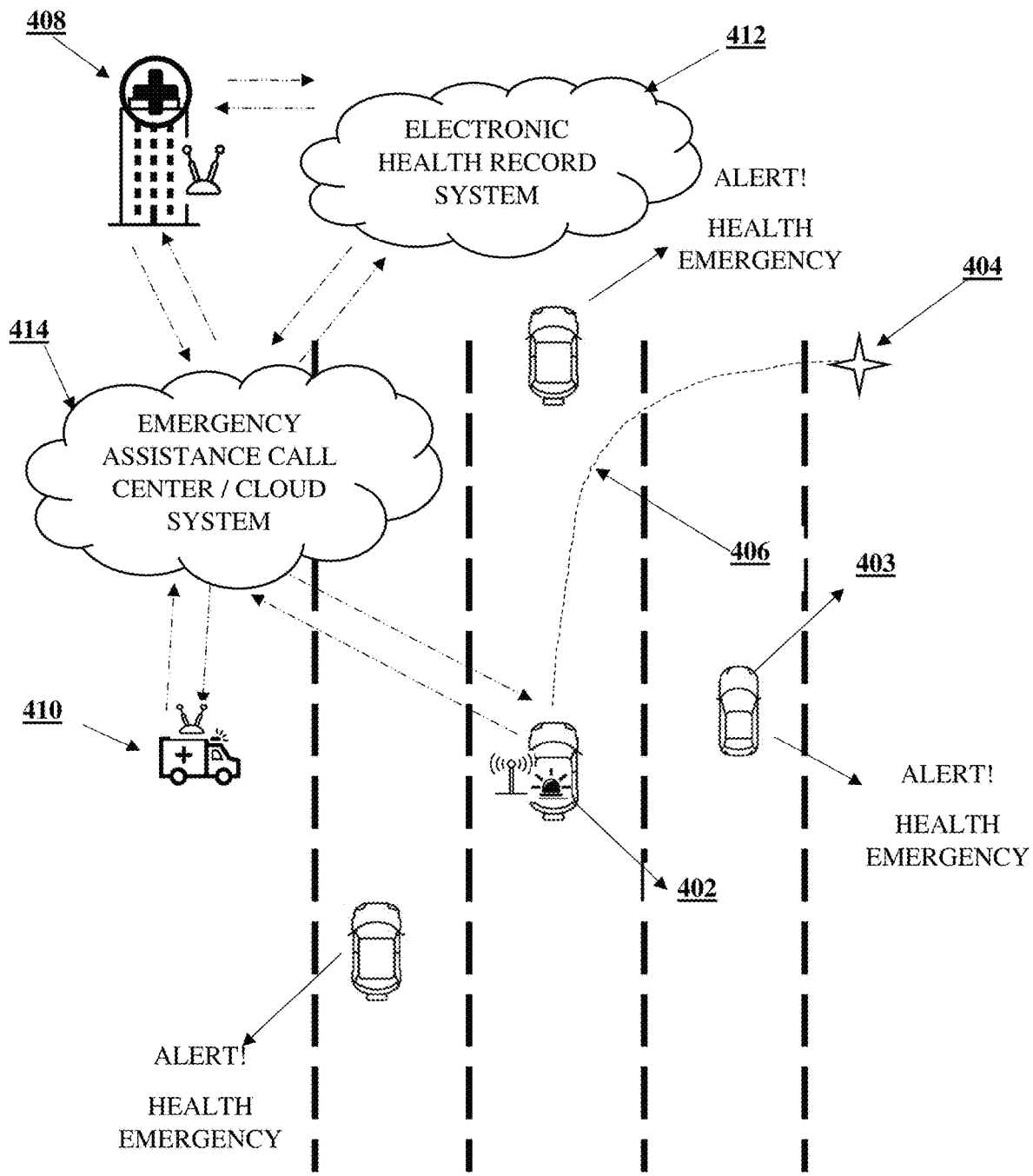
FIG. 4B shows the system assisting in an emergency situation via a call center or via a cloud network according to an embodiment.

FIG. 4B shows the system assisting an emergency situation via a call center or via a cloud network according to an embodiment. In an embodiment, the system detects that a passenger of the vehicle 402 is undergoing an emergency situation. The system then automatically would manage the traffic, i.e., nearby vehicles 403 by communicating a message of an emergency with the nearby vehicles. The message may comprise an instruction for a speed and an instruction for a course. The system would then identify the nearest emergency facility and make a call to the emergency facility 408. In addition, it would call emergency services 410. In an embodiment, electronic health records of the passenger 412 are shared with the emergency facility. In an embodiment, the emergency facility can directly access them from the electronic health record system. In this embodiment, the system may be executed via the network. The system may coordinate all the activities, including the vehicle's course of action. The system may be residing in a cloud or network 414 and a request to the call center by the vehicle may activate the system to perform the emergency assistance activities.

Figure 6A:
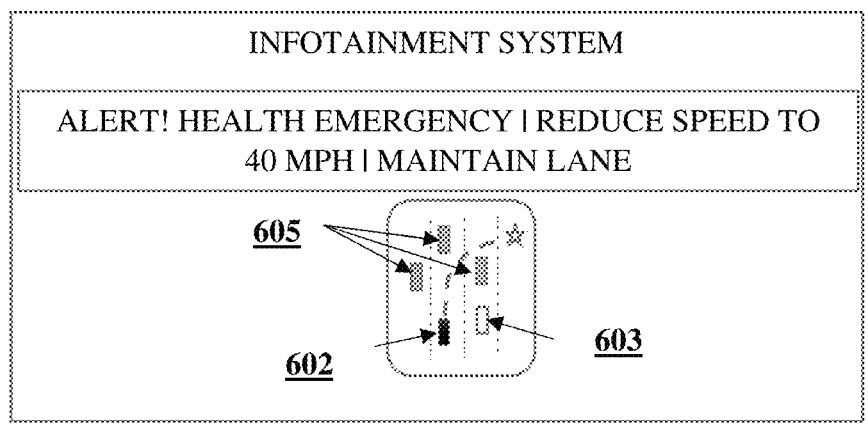
FIG. 6A shows a communication message that is displayed on a nearby vehicle on an infotainment system of the nearby vehicle which includes a graphic that is generated according to an embodiment.

FIG. 5A shows an example emergency message and content of the message that may be used for broadcasting or communicating with nearby vehicles according to an embodiment. In an embodiment, the message is similar to HL7 protocol. In an embodiment, the message to the nearby vehicle comprises the alert signal with a request for at least one of an instruction for speed and an instruction for course for the nearby vehicle. The alert signal includes information on emergencies due to medical issues. In an embodiment, the message is broadcast to all the vehicles. In an embodiment, the message is broadcast to all the vehicles on the side to which the vehicle is being pulled over, for example, if the vehicle is being pulled over to the right, all the right side vehicles are communicated the alert signal via the broadcast message. A sample emergency message to the nearby vehicle is shown in FIG. 5A where the fields comprise an event type or emergency type, user's vehicle location, pull over location, a request speed, and a request lane change message. A decoder of the location message installed in the vehicle may produce a graphic of the locations as shown in FIG. 6A on an infotainment system.

FIG. 5B shows an example emergency message and content of the message that may be used for broadcasting or communicating with a first responder or an emergency care unit according to an embodiment. In an embodiment, the message is similar to HL7 protocol. In an embodiment, the message to a first responder comprises the alert signal and a message. The alert signal includes information on emergencies due to medical issues. In an embodiment, the message is broadcast to more than one medical center. In an embodiment, the message is broadcast to a nearest emergency center. A sample emergency message to the nearby vehicle is shown in FIG. 5B where the fields comprise an event type or emergency type, passenger information, health parameters (from one or more sensors in the vehicle, including wearable devices), vehicle details, passenger seating details, passenger pre-health condition details, passenger allergy details, and emergency contact details. Vehicle details may further comprise type of vehicle, seating capacity, etc. Vehicle details may comprise, vehicle make, vehicle type such as a car, truck etc., vehicle number, vehicle owner, vehicle color, vehicle chassis id etc. Passenger pre-health condition details can be either user provided details recorded in the vehicle system or medical service provider data from a cloud server. In an embodiment, the vehicle can collect the data, upon user's permission, and load the details in the vehicle system. In an embodiment, the system can provide encrypted details for security reasons. In an embodiment, it can send a message to the third party, for example an insurer, to share the passenger's health related details to the medical center. In an embodiment, the system sends an encoded hyperlink that can provide access to the passenger's health records. A decoder of a medical center, upon additional authentication via a password or a pin, can access the medical records. In an embodiment, the password or pin is sent in a separate message followed by the main message. In an embodiment, one or more portions of the message comprising medical records or medical data are encrypted.

An embodiment relates to a vehicle, comprising: a first sensor, a second sensor; a communication module; and a processor; wherein the processor performs, under power, the following functions, wherein the functions comprise, generation, by the first sensor, an alert signal indicating an emergency; transmission, via a communication module, the alert signal to a nearby vehicle; establishment of a connection, with the nearby vehicle; communication, via the communication module, a first message to the nearby vehicle, wherein the first message comprises the alert signal and a first responder identification request; reception, via the communication module, a second message from the first responder, wherein the second message comprises location and credentials of the first responder; and wait, by the processor, a predefined time before taking an action, wherein the action comprises placing a call to one of a police department, and an emergency service.

An embodiment relates to a method, comprising: generating, by a first sensor, an alert signal indicating an emergency in a vehicle; transmitting, via a communication module, the alert signal to a nearby vehicle; establishing a connection, with the nearby vehicle; communicating, via the communication module, a first message to the nearby vehicle, wherein the first message comprises the alert signal and a first responder identification request; receiving, via the communication module, a second message from the first responder, wherein the second message comprises location and credentials of the first responder; and waiting, by a processor, a predefined time before taking an action, wherein the action comprises placing a call to one of a police department, and an emergency service.

An embodiment relates to a system, comprising: a first sensor, a second sensor; a communication module; and a processor; wherein the processor performs, under power, the following functions, wherein the functions comprise: generation, by the first sensor, an alert signal indicating an emergency in a vehicle; transmission, via the communication module, the alert signal to a nearby vehicle; establishment of a connection, with the nearby vehicle; communication, via the communication module, a first message to the nearby vehicle, wherein the first message comprises the alert signal and a first responder identification request; reception, via the communication module, a second message from the first responder, wherein the second message comprises location and credentials of the first responder; and wait, by the processor, a predefined time before taking an action, wherein the action comprises placing a call to one of a police department, and an emergency service. According to an embodiment, the system is configured to be a component of the vehicle.

An embodiment relates to a system configured to receive a software application installation package over a computer network; and install the software application onto the computing hardware associated with a vehicle; wherein the software application comprises: set of instructions executable by a computing hardware and stored in a non-transitory storage medium that, when executed, cause the computing hardware to implement operations comprising: generating, by a first sensor, an alert signal indicating an emergency in a vehicle; transmitting, via a communication module, the alert signal to a nearby vehicle; establishing a connection, with the nearby vehicle; communicating, via the communication module, a first message to the nearby vehicle, wherein the first message comprises the alert signal and a first responder identification request; receiving, via the communication module, a second message from the first responder, wherein the second message comprises location and credentials of the first responder; waiting, by a processor, a predefined time before taking an action, wherein the action comprises placing a call to one of a police department, and an emergency service.

An embodiment relates to a non-transitory computer-readable medium having stored thereon instructions executable by a computer system to perform operations comprising: generating, by a first sensor, an alert signal indicating an emergency in a vehicle; transmitting, via a communication module, the alert signal to a nearby vehicle; establishing a connection, with the nearby vehicle; communicating, via a communication module, a first message to the nearby vehicle, wherein the first message comprises the alert signal and a first responder identification request; receiving, via the communication module, a second message from the first responder, wherein the second message comprises location and credentials of the first responder; and waiting, by a processor, a predefined time before taking an action, wherein the action comprises placing a call to one of a police department, and an emergency service.

FIG. 6A shows a broadcast message or a communication message that is displayed in a nearby vehicle on an infotainment system of the nearby vehicle which includes a graphic that is generated according to an embodiment. When the nearby vehicle or vehicles receive an emergency alert signal, the system, upon identifying such message, may map the location of the surrounding vehicles including the vehicle receiving the message and possible heading profile (or pull over profile) of the user vehicle, i.e., vehicle in which the passenger was experiencing an emergency, in a graphical format for better understanding of course of action. Vehicle experiencing an emergency is shown as 602 and the vehicle which received the message is shown as 603. The graphic also shows the surrounding vehicles 605 to provide a clear depiction of the surroundings of the vehicle or the traffic around the vehicle. In an embodiment, the nearby vehicle decodes the message of location sent by the user's vehicle and maps it. In another embodiment, the information required for mapping may be obtained by the nearby vehicle using its own sensors. In an embodiment of the system, the message is displayed on the infotainment system of the nearby vehicle. In an embodiment of the system, the nearby vehicle displays a first graphic of the vehicle, a second graphic of the nearby vehicle, the path, and the pull over location on an infotainment system of the nearby vehicle.

Figure 6B:
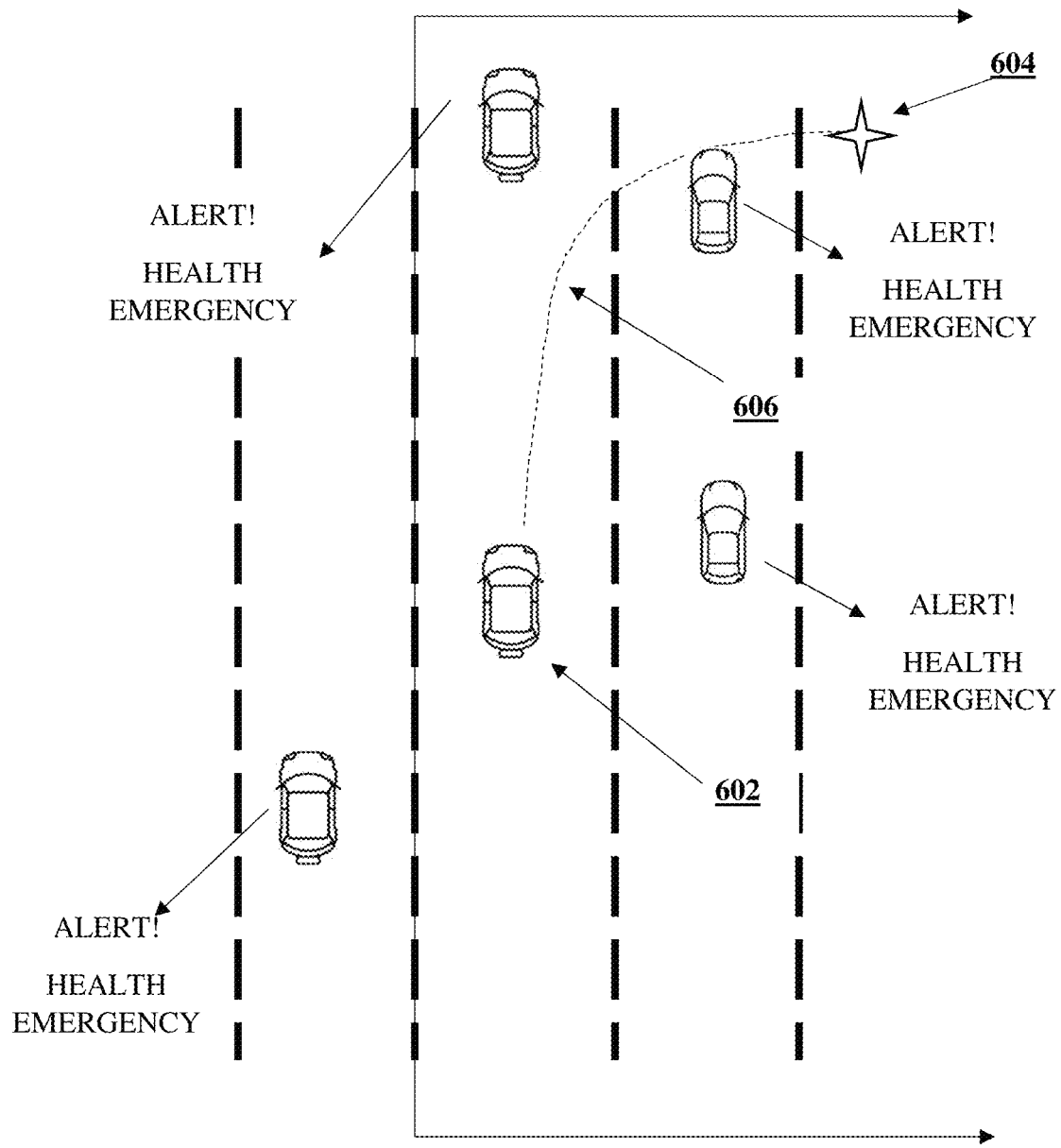
FIG. 6B shows a broadcast of a message to all the nearby vehicles during an emergency according to an embodiment.

FIG. 6B shows a broadcast of a message to all the nearby vehicles during an emergency according to an embodiment. The system, upon identifying that the passenger of the user's vehicle is experiencing an emergency situation due to health as shown in 602, may trigger the alert signal to the driver on an infotainment system. In an embodiment, the message can be sent to any device in the nearby vehicles. It may automatically broadcast a message to all the nearby vehicles, within a certain range, to inform them that the user's vehicle has an emergency situation. The message may alert the nearby vehicle drivers and prompt for an action voluntarily. The nearby vehicles may include autonomous vehicles, semi-autonomous vehicles and driver based vehicles. The user's vehicle may automatically find a pull over location as shown at 604 and provide at least a path to a pull over point.

Figure 6C:
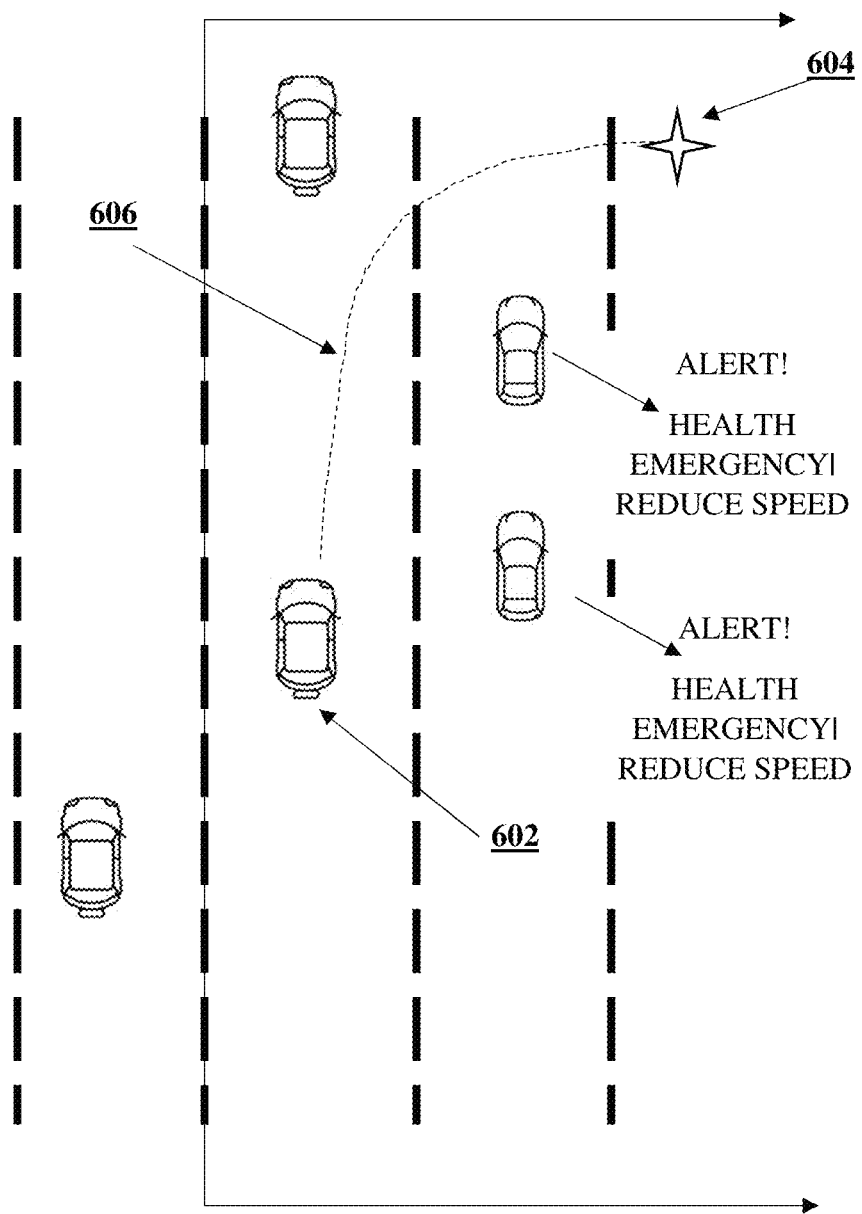
FIG. 6C shows a broadcast of a message to a group of nearby vehicles during an emergency according to an embodiment.

FIG. 6C shows a broadcast of a message to a group of nearby vehicles during an emergency according to an embodiment. The system, upon identifying that the passenger of the user's vehicle is experiencing an emergency situation due to health as shown in 602, may trigger the alert signal to the driver on an infotainment system. In an embodiment, the message can be sent to any device in the nearby vehicles. It may automatically broadcast a message to a section of the nearby vehicles or selected nearby vehicles. In an embodiment of the system, the message is a customized message for each of the plurality of vehicles based on the location of the vehicle. For example, if the user's vehicle wants to pull over to a pull over location as shown in 604 along the pull over path 606 computed automatically by the system, then the system may automatically alert only the vehicles that are on the right-side lanes to the user's vehicle. In an embodiment, the pull over path is based on finding out the speed of the nearby vehicles and the real time location of the nearby vehicles and computing the feasible pull over location 604 along with pull over path 606. The message may alert the nearby vehicle drivers and prompt for an action voluntarily, such as reducing the speed by the drivers of the nearby vehicles. The nearby vehicles may include autonomous vehicles, semi-autonomous vehicles and driver based vehicles. In an embodiment of the system, the nearby vehicle comprises a plurality of vehicles.

In an embodiment of the system, the message is broadcast to the plurality of vehicles. In an embodiment of the system, the instruction for speed comprises at least one of a reduction in speed, maintenance of speed, an increase in speed, and complete stop. In an embodiment of the system, wherein the instruction for speed is determined by the vehicle based on the pull over location and the second location of the nearby vehicle. In an embodiment of the system, the instruction for course comprises at least one of a lane keeping, a lane changing, a pull over to a side of a road. In an embodiment of the system, the message is individualized for the nearby vehicle.

In an embodiment of the system, the current location of the vehicle is obtained or determined in real time via a global positioning system. In an embodiment of the system, wherein a location of the nearby vehicle is obtained by at least one of a global position system, an estimation based on speed of the nearby vehicle and the first location, and an estimation based on a strength of a communication signal.

Figure 6D:
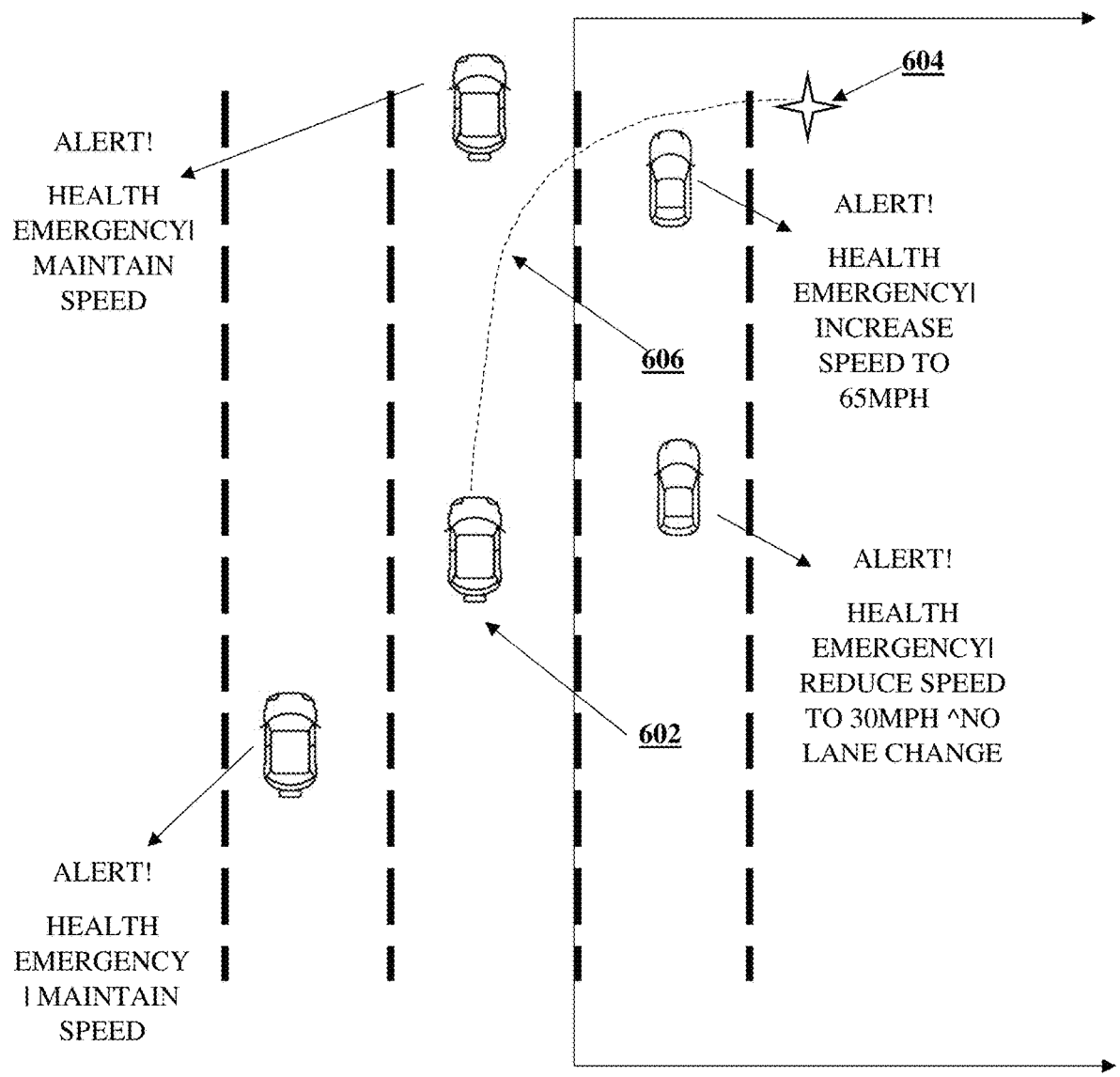
FIG. 6D shows a communication of a message to nearby vehicles during an emergency according to an embodiment.

FIG. 6D shows a communication of a message to nearby vehicles during an emergency according to an embodiment. The system, upon identifying that the passenger of the user's vehicle is experiencing an emergency situation due to health as shown in 602, may trigger the alert signal to the driver on an infotainment system. It may automatically send a message to nearby vehicles. For example, if the user's vehicle wants to pull over to a pull over location as shown in 604 along the pull over path 606 computed automatically by the system, then the system may automatically alert the nearby vehicles with an instruction for speed and/or a course. In an embodiment, the pull over path is based on finding out the speed of the nearby vehicles and the real time location of the nearby vehicles and computing the feasible pull over location 604 along with pull over path 606. The message may alert the nearby vehicle drivers and request an action voluntarily, such as reducing or increasing the speed, changing a lane, etc., by the drivers of the nearby vehicles. The nearby vehicles may include autonomous vehicles, semi-autonomous vehicles and driver based vehicles. In an embodiment, the message can be sent to any device in the nearby vehicles. In an embodiment, the message is individual to each nearby vehicle or group of vehicles based on the location of the nearby vehicles and/or pull over location of the user's vehicle. The individualized or customized message comprises an instruction for speed and an instruction for course that is specific to each vehicle which are computed based on the location of the nearby vehicles and/or pull over location of the user's vehicle.

Figure 6E:
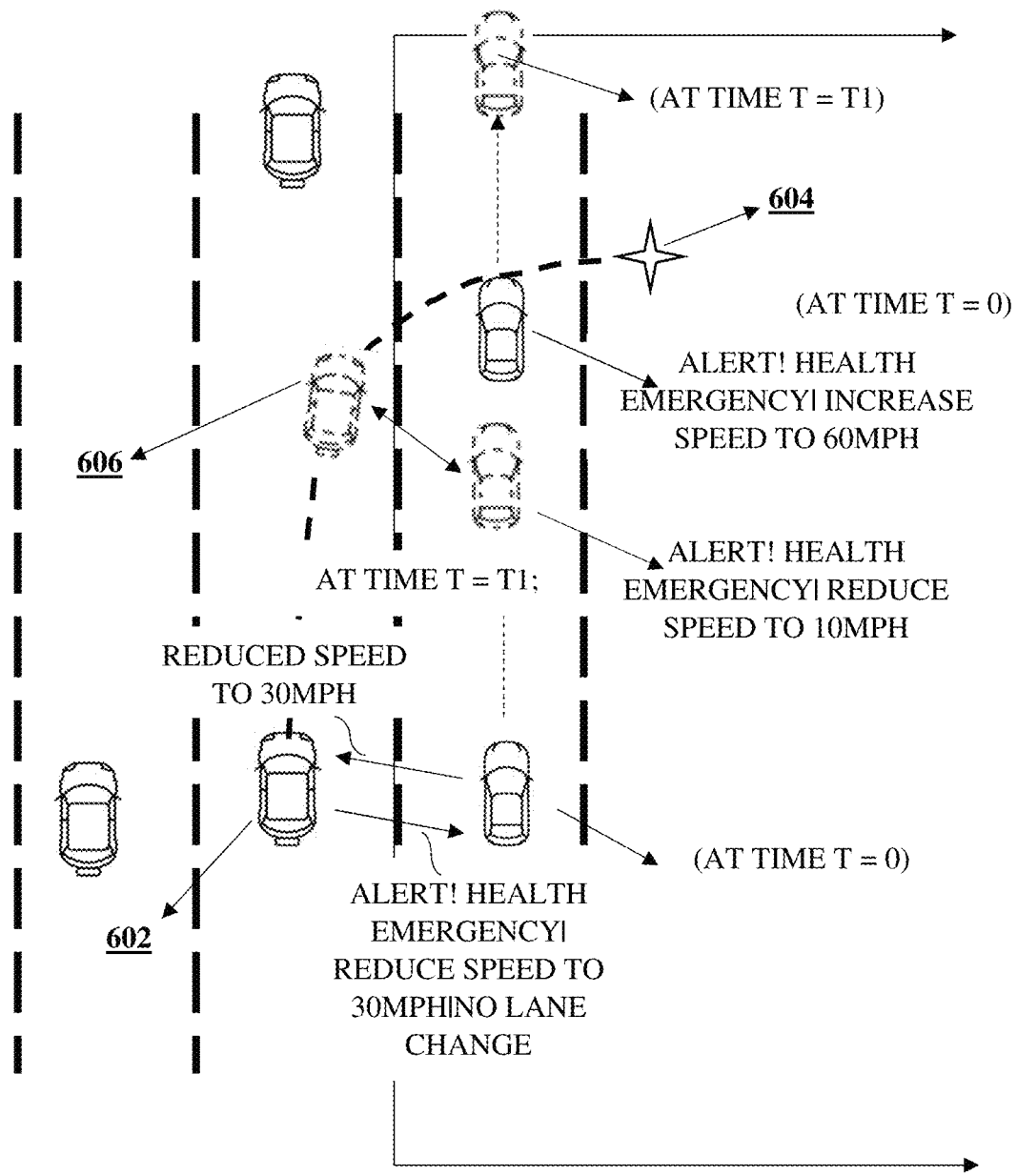
FIG. 6E shows a bidirectional communication with nearby vehicles during an emergency in the user's vehicle according to an embodiment.

FIG. 6E shows a bidirectional communication with nearby vehicles during an emergency in the user's vehicle according to an embodiment. The system, upon identifying that the passenger of the user's vehicle is experiencing an emergency situation due to health as shown in 602, may trigger the alert signal to the driver on an infotainment system. It may automatically send a message to nearby vehicles. For example, if the user's vehicle wants to pull over to a pull over location as shown in 604 along the pull over path 606 computed automatically by the system, then the system may automatically alert the nearby vehicles with an instruction for speed and/or a course. In an embodiment, the pull over path is based on finding out the speed of the nearby vehicles and the real time location of the nearby vehicles and computing the feasible pull over location 604 along with the pull over path 606. The message may alert the nearby vehicle drivers and request an action voluntarily, such as reducing or increasing the speed, changing a lane, etc., by the drivers of the nearby vehicles. The nearby vehicles may include autonomous vehicles, semi-autonomous vehicles and driver based vehicles. In an embodiment, the message can be sent to any device in the nearby vehicles as shown at time T=0. In an embodiment, the nearby vehicles may message or communicate their new speed. Further, when the user's vehicle finds the nearby vehicle too close, as shown at T=T1, it may communicate to the nearby vehicle to further reduce its speed. Thus, the user's vehicle and nearby vehicles may continue to communicate until a successful pull over by the user's vehicle to the planned pull over location is performed.

An embodiment relates to a vehicle, comprising: a first sensor, a second sensor; a communication module; and a processor; wherein the processor performs, under power, following functions, wherein the functions comprise: generation, by the first sensor, an alert signal indicating a need for a pull over of the vehicle; detection, based on the second sensor associated with the vehicle, a nearby vehicle; establishment of a connection, with the nearby vehicle; transmission, via the communication module, a first message to the nearby vehicle, wherein the first message comprises the alert signal and at least one of an instruction for speed and an instruction for course for the nearby vehicle; reception, via the communication module, a second message from the nearby vehicle, wherein the second message comprises a speed of the nearby vehicle; determination, a required speed of the vehicle based on a first location of the vehicle, a second location of the nearby vehicle, and the speed of the nearby vehicle for the pull over; generation, based on the required speed, a path for the pull over to a pull over location for the vehicle; and transmission, via the communication module, a third message to the nearby vehicle, wherein the third message comprises a further request for an instruction for speed and an instruction for course for the nearby vehicle; and maneuver, the vehicle along the path to the pull over location.

An embodiment relates to a method, comprising: generating, by a first sensor, an alert signal indicating a need for a pull over of a vehicle; detecting, based on a second sensor associated with the vehicle, a nearby vehicle; connecting, with the nearby vehicle; transmitting, via a communication module, a first message to the nearby vehicle, wherein the first message comprises the alert signal and at least one of an instruction for speed and an instruction for course for the nearby vehicle; receiving, via the communication module, a second message from the nearby vehicle, wherein the second message comprises a speed of the nearby vehicle; calculating, a required speed of the vehicle based on a first location of the vehicle, a second location of the nearby vehicle, and the speed of the nearby vehicle for the pull over; generating, based on the required speed, a path for the pull over to a pull over location for the vehicle; transmitting, via the communication module, a third message to the nearby vehicle, wherein the third message comprises a further request for an instruction for speed and an instruction for course for the nearby vehicle; and maneuvering, the vehicle along the path to the pull over location.

An embodiment relates to a system, comprising: a first sensor, a second sensor; a communication module; and a processor; wherein the processor performs, under power, following functions, wherein the functions comprise, generation, by the first sensor, an alert signal indicating a need for a pull over of a vehicle; detection, based on the second sensor associated with the vehicle, a nearby vehicle; establishment of a connection, with the nearby vehicle; transmission, via the communication module, a first message to the nearby vehicle, wherein the first message comprises the alert signal and at least one of an instruction for speed and an instruction for course for the nearby vehicle; reception, via the communication module, a second message from the nearby vehicle, wherein the second message comprises a speed of the nearby vehicle; determination, a required speed of the vehicle based on a first location of the vehicle, a second location of the nearby vehicle, and the speed of the nearby vehicle for the pull over; generation, based on the required speed, a path for the pull over to a pull over location for the vehicle; transmission, via the communication module, a third message to the nearby vehicle, wherein the third message comprises a further request for an instruction for speed and an instruction for course for the nearby vehicle; and maneuver, the vehicle along the path to the pull over location. According to an embodiment, the system is configured to be a component of the vehicle.

An embodiment relates to a system configured to receive a software application installation package over a computer network; and install the software application onto the computing hardware associated with a vehicle; wherein the software application comprises: set of instructions executable by a computing hardware and stored in a non-transitory storage medium that, when executed, cause the computing hardware to implement operations comprising, generating, by a first sensor, an alert signal indicating a need for a pull over of a vehicle; detecting, based on a second sensor associated with the vehicle, a nearby vehicle; connecting, with the nearby vehicle; transmitting, via a communication module, a first message to the nearby vehicle, wherein the first message comprises the alert signal and at least one of an instruction for speed and an instruction for course for the nearby vehicle; receiving, via the communication module, a second message from the nearby vehicle, wherein the second message comprises a speed of the nearby vehicle; calculating, a required speed of the vehicle based on a first location of the vehicle, a second location of the nearby vehicle, and the speed of the nearby vehicle for the pull over; generating, based on the required speed, a path for the pull over to a pull over location for the vehicle; transmitting, via the communication module, a third message to the nearby vehicle, wherein the third message comprises a further request for an instruction for speed and an instruction for course for the nearby vehicle; and maneuvering, the vehicle along the path to the pull over location.

An embodiment relates to a non-transitory computer-readable medium having stored thereon instructions executable by a computer system to perform operations comprising, generating, by a first sensor, an alert signal indicating a need for a pull over of a vehicle; detecting, based on a second sensor associated with the vehicle, a nearby vehicle; connecting, with the nearby vehicle; transmitting, via a communication module, a first message to the nearby vehicle, wherein the first message comprises the alert signal and at least one of an instruction for speed and an instruction for course for the nearby vehicle; receiving, via the communication module, a second message from the nearby vehicle, wherein the second message comprises a speed of the nearby vehicle; calculating, a required speed of the vehicle based on a first location of the vehicle, a second location of the nearby vehicle, and the speed of the nearby vehicle for a pull over; generating, based on the required speed, a path for the pull over to a pull over location for the vehicle; transmitting, via the communication module, a third message to the nearby vehicle, wherein the third message comprises a further request for an instruction for speed and an instruction for course for the nearby vehicle; and maneuvering, the vehicle along the path to the pull over location.

Figure 7:
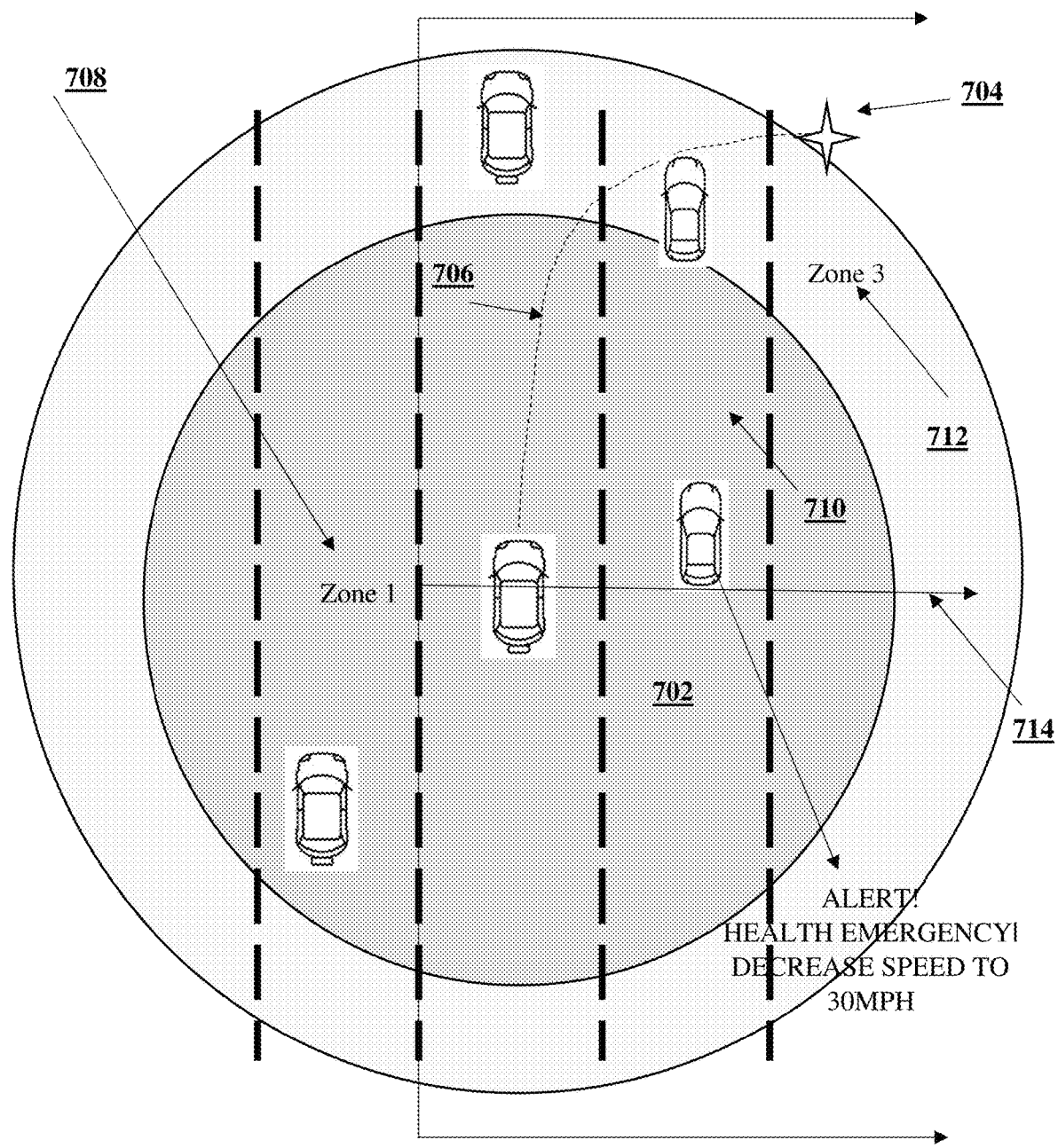
FIG. 7 shows a region around the vehicle undergoing emergency classified into zones of influence according to an embodiment.

FIG. 7 shows the region around the vehicle undergoing an emergency classified into zones of influence according to an embodiment. In an embodiment, the region around the user's vehicle 702 which is experiencing the emergency situation is divided into a plurality of zones or a plurality of regions. The system of the user's vehicle may find a pull over location 704 and a pull over path 706. In an embodiment, the surrounding region of the vehicle undergoing an emergency is classified into three zones of influence, namely high influence zone, zone 1 shown as 708, medium influence zone, zone 2 shown as 710, low influence zone, zone 3 shown as 712. According to an embodiment, zones of influence are circular. In an embodiment they could be linear extending on one side of the vehicle, for example right side of the user's vehicle or region above the line 714 on the right side region. The zones of influence are based on a speed of the user's vehicle 702 and may be a predetermined distance. In an embodiment, the zones of influence are based on vehicle density around the user's car/vehicle. A message communicated from the user's vehicle regarding the emergency and the request may be specific to a zone of influence and common to all the vehicles in the zone of influence. In an embodiment, the message may be specific to a zone of influence and individualized to the vehicles in the zone of influence based on their location. For example, as shown in the FIG. 7, vehicles in zone 2 and zone 3 may not receive any message while a vehicle in zone 1 may receive a message comprising a request for a change in a speed or a change in a course. In an embodiment of the vehicle, at least one of the speeds and the course of the nearby vehicle when in the high influence zone is set to a requested speed by the vehicle. In an embodiment of the vehicle, the nearby vehicle when in the medium influence zone is requested to change at least one of the speeds and the course by the vehicle. In an embodiment of the vehicle, the nearby vehicle when in the low influence zone is requested to change at least one of the speeds and the course by the vehicle.

In an embodiment of the system, wherein the functions further comprise determining zones of influence based on a distance of the nearby vehicle from the vehicle and the speed of the nearby vehicle relative to the vehicle. In an embodiment of the system, the zones of influence comprise a high influence zone, a medium influence zone and a low influence zone. In an embodiment of the system, at least one of the speeds and the course of the nearby vehicle when in the high influence zone is set to a requested speed by the vehicle. In an embodiment of the system, the nearby vehicle when in the medium influence zone is requested to change at least one of the speeds and the course by the vehicle. In an embodiment of the system, the nearby vehicle when in the low influence zone is requested to change at least one of the speeds and the course by the vehicle.

Figure 8:
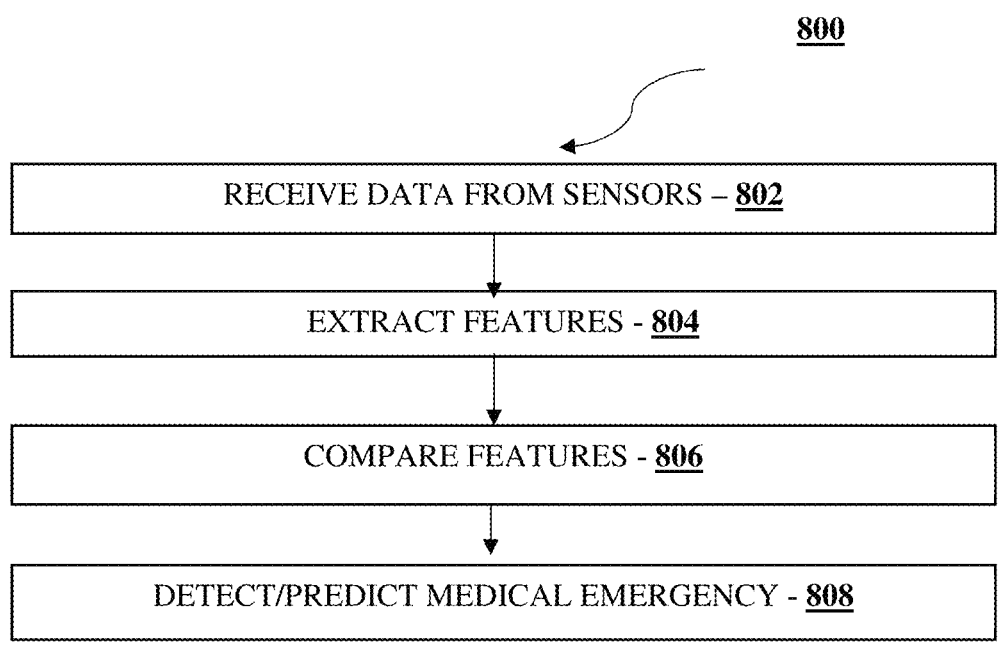
FIG. 8 shows a flowchart for detecting or predicting medical emergency from the sensor data according to an embodiment.

FIG. 8 shows a flowchart for detecting or predicting medical emergency from the sensor data according to an embodiment. According to an embodiment, the emergency detection module 800 comprises the components of an apparatus and the system to detect physiological characteristics of the passenger. The components may each be adapted to measure, track, and/or monitor the passenger by using one or more of the sensors 802 which may comprise camera, microphone, pressure sensors, occupancy sensors, health sensors such as heart rate sensor, blood pressure (BP) sensor, temperature sensor, etc. The data may come from other sources such as a mobile device, a health or fitness tracker, etc. In some embodiments, the system may extract features from the data using machine learning or artificial intelligence algorithm, such features for example may include, but not limited to facial expression, body posture, a voice print, body position and/or motion, vitals—heart rate, respiration rate, body temperature, blood pressure, perspiration, skin color, lip color, comfort level, in vehicle noises, passenger noises, seat occupancy, grip pressure, allergic reaction, etc. as shown at 804. Passenger noises may include a noise made prior to, during or after the emergency event. A seat occupancy may determine where the passenger is seated, whether the passenger is a child and in a child car seat, etc., and a grip pressure may be measured by the force sensors in the car seat or in the belts of the car seat. The processor may be enabled to extract a height of the passenger based on the height his head reaches on the seat, the leg resting position, and a posture from the camera. Facial features include eye, mouth, lips, facial muscle, skin, shape of the face etc. Once the features are extracted using image processing algorithm and artificial intelligence, the system uses a pre-trained artificial intelligence/machine learning (AI/ML) model to compare the features at 806; The system based on the match of features may predict or detect an emergency 808. In an embodiment, the system can predict or detect health emergency related to for example, choking, breathing issue, fever, stroke, heart attack, asthma, seizure, epilepsy, diarrhea, cough, rash, vomiting; loss of consciousness, colic, nosebleed, bleeding, neurological disorder, etc. Example: When a child is experiencing a seizure, some of the symptoms could be body spasms and shaking (a "fit"), loss of awareness or unusual sensations, stiffness or twitching of part of body, such as an arm or hand, smacking lips, rubbing hands, making random noises, moving arms around, picking at clothes or fiddling with objects, chewing, or swallowing, staring blankly into space. By combining the image classification and features recognition algorithm, the health emergency can be predicted as a possible seizure. In an embodiment, the system is designed to achieve artificial intelligence (AI) via a model based on predetermined rules, also referred to as rule-based AI system. For example, if the face is drooping (identify from image sensor), arm is numb/weak (identify from image or arm pressure via pressure sensor), speech is slurred (identify via a microphone recording) then provide an emergency alert and indicate that the emergency alert is for possible stroke, with a severity score or scale of 10.

Figure 9A:
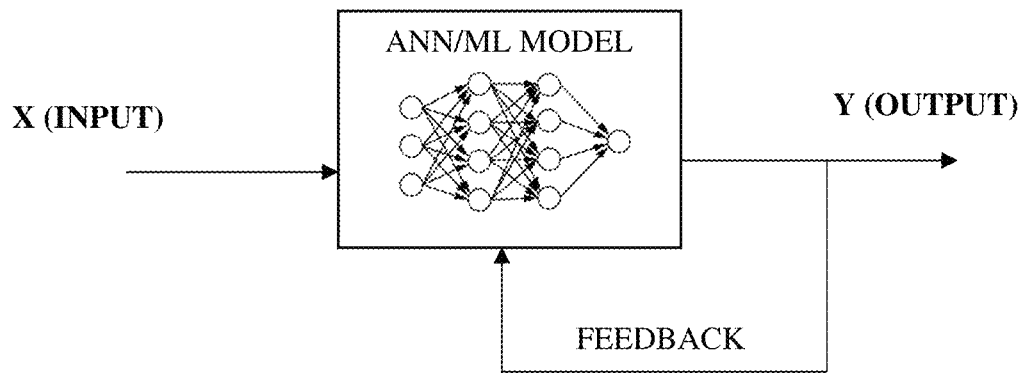
FIG. 9A shows a structure of the neural network/machine learning model with a feedback loop according to an embodiment.

FIG. 9A shows a structure of the neural network/machine learning model with a feedback loop. Artificial neural networks (ANNs) model comprises an input layer, one or more hidden layers, and an output layer. Each node, or artificial neuron, connects to another and has an associated weight and threshold. If the output of any individual node is above the specified threshold value, that node is activated, sending data to the next layer of the network. Otherwise, no data is passed to the next layer of the network. A machine learning model or an ANN model may be trained on a set of data to take a request in the form of input data, make a prediction on that input data, and then provide a response. The model may learn from the data. Learning can be supervised learning and/or unsupervised learning and may be based on different scenarios and with different datasets. Supervised learning comprises logic using at least one of a decision tree, logistic regression, support vector machines. Unsupervised learning comprises logic using at least one of a k-means clustering, a hierarchical clustering, a hidden Markov model, and an apriori algorithm. The output layer may predict or detect a health issue and the severity of the health issue based on the input data.

In an embodiment, ANN's may be a Deep-Neural Network (DNN), which is a multilayer tandem neural network comprising Artificial Neural Networks (ANN), Convolution Neural Networks (CNN) and Recurrent Neural Networks (RNN) that can recognize features from inputs, do an expert review, and perform actions that require predictions, creative thinking, and analytics. In an embodiment, ANNs may be Recurrent Neural Network (RNN), which is a type of Artificial Neural Networks (ANN), which uses sequential data or time series data. Deep learning algorithms are commonly used for ordinal or temporal problems, such as language translation, Natural Language Processing (NLP), speech recognition, and image recognition, etc. Like feed-forward and convolutional neural networks (CNNs), recurrent neural networks utilize training data to learn. They are distinguished by their "memory" as they take information from prior input via a feedback loop to influence the current input and output. An output from the output layer in a neural network model is fed back to the model through the feedback. The variations of weights in the hidden layer(s) will be adjusted to fit the expected outputs better while training the model. This will allow the model to provide results with far fewer mistakes.

The neural network is featured with the feedback loop to adjust the system output dynamically as it learns from the new data. In machine learning, backpropagation and feedback loops are used to train an AI model and continuously improve it upon usage. As the incoming data that the model receives increases, there are more opportunities for the model to learn from the data. The feedback loops, or backpropagation algorithms, identify inconsistencies and feed the corrected information back into the model as an input.

Even though the AI/ML model is trained well, with large sets of labeled data and concepts, after a while, the models' performance may decline while adding new, unlabeled input due to many reasons which include, but not limited to, concept drift, recall precision degradation due to drifting away from true positives, and data drift over time. A feedback loop to the model keeps the AI results accurate and ensures that the model maintains its performance and improvement, even when new unlabeled data is assimilated. A feedback loop refers to the process by which an AI model's predicted output is reused to train new versions of the model.

Initially, when the AI/ML model is trained, a few labeled samples comprising both positive and negative examples of the concepts (for e.g., health issues) are used that are meant for the model to learn. Afterward, the model is tested using unlabeled data. By using, for example, deep learning and neural networks, the model can then make predictions on whether the desired concept/s (for e.g., health issue that needs to be detected) are in unlabeled images. Each image is given a probability score where higher scores represent a higher level of confidence in the models' predictions. Where a model gives an image a high probability score, it is auto-labeled with the predicted concept. However, in the cases where the model returns a low probability score, this input may be sent to a controller (may be a human moderator) which verifies and, as necessary, corrects the result. The human moderator may be used only in exception cases. The feedback loop feeds labeled data, auto-labeled or controller-verified, back to the model dynamically and is used as training data so that the system can improve its predictions in real-time and dynamically.

Figure 9B:
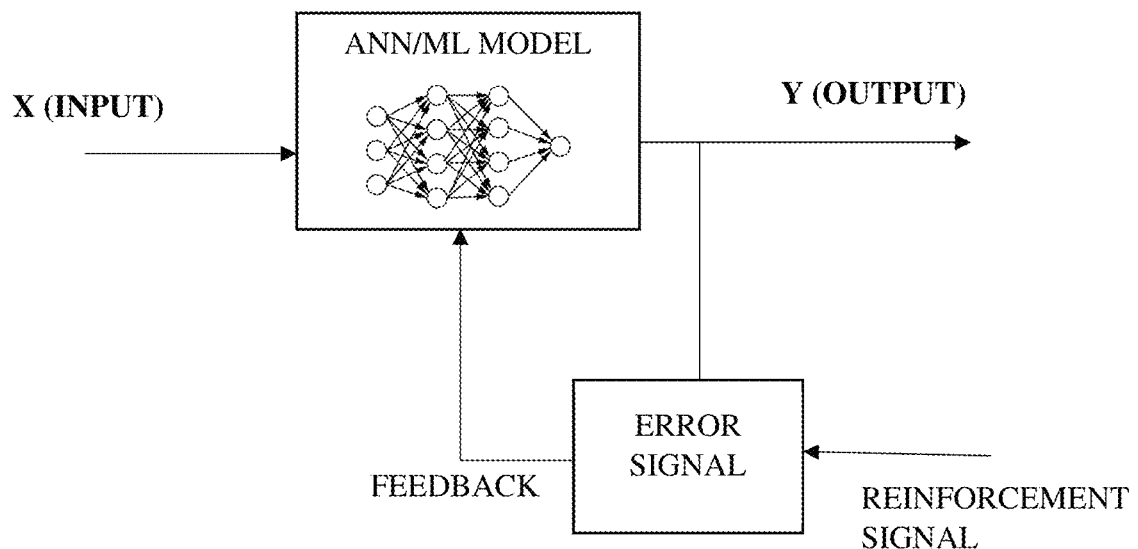
FIG. 9B shows a structure of the neural network/machine learning model with reinforcement learning according to an embodiment.

FIG. 9B shows a structure of the neural network/machine learning model with reinforcement learning. The network receives feedback from authorized networked environments. Though the system is similar to supervised learning, the feedback obtained in this case is evaluative not instructive, which means there is no teacher as in supervised learning. After receiving the feedback, the network performs adjustments of the weights to get better predictions in the future. Machine learning techniques, like deep learning, allow models to take labeled training data and learn to recognize those concepts in subsequent data and images. The model may be fed with new data for testing, hence by feeding the model with data it has already predicted over, the training gets reinforced. If the machine learning model has a feedback loop, the learning is further reinforced with a reward for each true positive of the output of the system. Feedback loops ensure that AI results do not stagnate. By incorporating a feedback loop, the model output keeps improving dynamically and over usage/time.

Figure 9C:
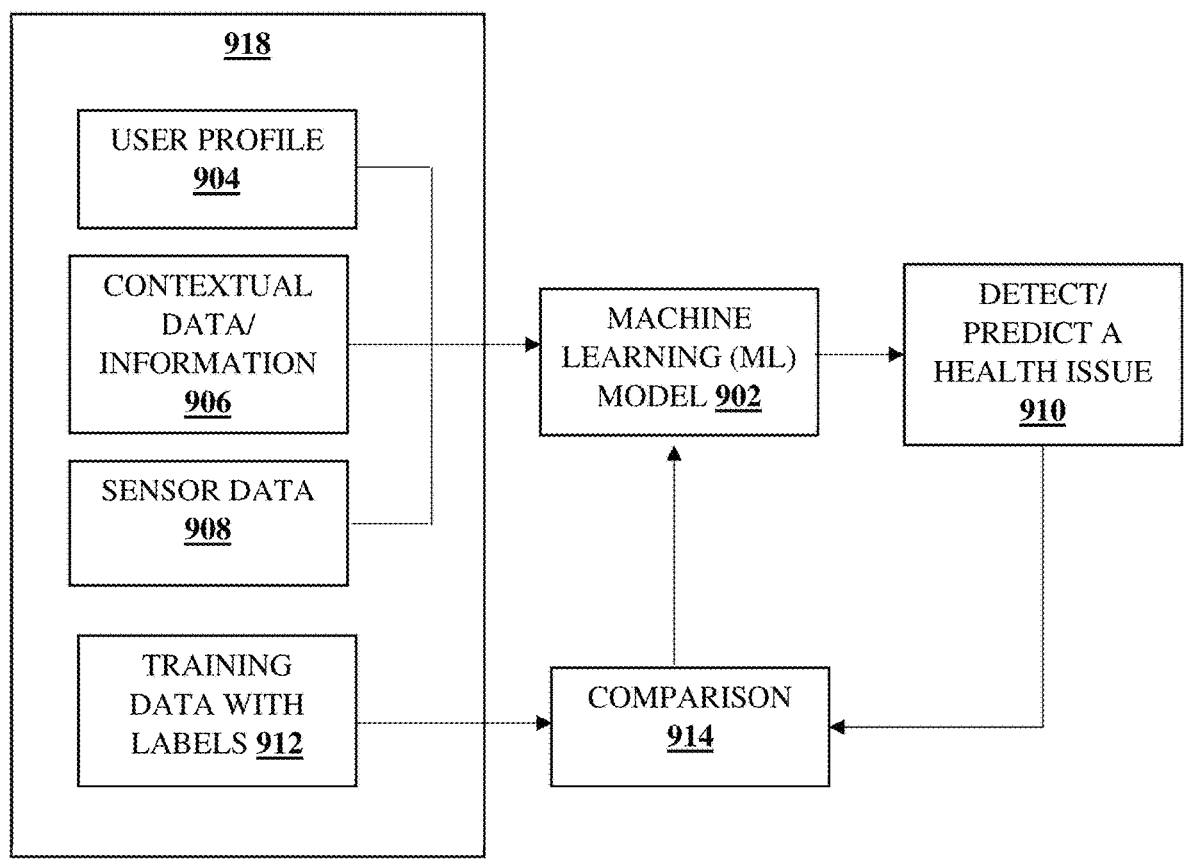
FIG. 9C shows an example block diagram for detecting a health emergency using a machine learning model according to an embodiment.

FIG. 9C shows an example block diagram for detecting a health emergency using a machine learning model. The machine learning model 902 may take as input any data associated with the passenger and learn to identify features within the data that are predictive of personalization preferences. The training data sample may include, for example, the passenger's profile information 904, such as the age, gender, weight, height, ethnicity, demographic location, residence location, work location, past health conditions, data from health records and any other suitable data relating to the passenger. In an embodiment, it relates to systems and methods that trigger a vehicle emergency event or the like, capture the health status of a previously identified or unidentified vehicle passenger in real time using an on-board camera and/or other sensors. This vehicle passenger identification and health status information are transmitted to the cloud, where the vehicle passenger identification is coupled with available public health profile information in the case of a previously identified vehicle passenger. Subsequently, the health status information and public health profile information are transmitted to an emergency responder or the like, thereby aiding in rendering medical assistance to an injured or sick vehicle passenger. The systems and methods of the present disclosure may also provide data analytics information that may be used later to improve vehicle safety. When a vehicle passenger enters a vehicle, he or she is identified by the vehicle system, using an interior camera and a facial recognition algorithm or the like, a near-field mobile device identification methodology, a self-identification user interface, or the like. This identification process may be supplemented by one or more pre-populated potential vehicle passenger databases resident in the cloud subsystem. In any event, the vehicle subsystem provides a real time vehicle passenger list or map (optionally also generated using one or more on-board vehicle passenger position sensors or the like) that is transmitted to and maintained by the cloud subsystem. This real time vehicle passenger list or map is associated with a given vehicle identifier, for example. Thus, at all times, the cloud subsystem monitors who is in a particular vehicle and, preferably, where they are seated in the vehicle. In an embodiment, there can be a vehicle passenger matching algorithm which may be in the vehicle system or is remote from the vehicle system in a cloud environment. The vehicle system transmits a unique vehicle passenger ID to the vehicle passenger matching algorithm for each sensed/imaged vehicle passenger. Vehicle passenger updates are then transmitted to the cloud system for maintaining the vehicle passenger ride lists, associating the appropriate public health profiles, and providing them to emergency responders accordingly.

In an embodiment, the training data sample may also include current contextual information 906 relating to the ride. This may include, for example, location of the vehicle, current weather conditions, temperature, time of day, traffic conditions in the region, seating position or location within the vehicle, posture of the passenger, and other passengers in the vehicle, etc. The system may also garner contextual information 906 from a device in the vehicle or a device of the passenger. For example, through an application installed on the device, such as Google® maps and location services, the system may know the ride details. For example, the passengers' state of mind may be obtained from an image of the camera where eye pattern is monitored, a sensor where heart rate is monitored. The system may correlate the eye movements with the health data. In an embodiment, the application may access other types of application usage data from other applications (including the operating system) installed on the passenger's device and use them as contextual information 906. This may include other applications that are being used before and/or during the ride (e.g., whether it was a gaming application, a video or productivity application). In an embodiment, a microphone installed in the vehicle or on an external device in the vehicle may record the noises and conversation of the passengers. The application may also query the other applications for data relating to, for example, age, gender, circle of friends, family, user destination, emergency contacts, the friends' interests, vehicle data, trip information, etc. Vehicle data, such as speed and trip data such as origin and destination, and interim stops may further indicate whether the passenger is going home from work, going to work from home, picking children up, running an errand, etc., which may also serve as contextual information 906.

Real-time sensor data 908 may include, for example, video, image, audio, infrared, temperature, 3D modeling, and any other suitable types of data that capture the passenger's current state. In an embodiment, the real-time sensor data may be processed using one or more machine learning models 902 trained and based on similar types of data to predict real-time features of the passenger. The real-time features may include, for example, the passenger's current mood (e.g., happy, angry, sad, etc.), stress level, comfort level with respect to vehicle amenities (e.g., temperature, audio, entertainment, etc.), health condition, and/or any other features that may characterize or represent the passenger's current state. Current information about the passenger may be used for the detection of health issues or emergencies. For example, currently detected sensor data and/or previously known information about the passenger may be used to predict the passenger's health condition.

Any of the aforementioned types of data (e.g., user profile data 904, contextual information 906, sensor data 908, or any other data) may correlate with the passenger's general health condition and disposition, and such correlation may be automatically learned by the machine learning model 902. In an embodiment, during training, the machine learning model 902 may process the training data sample (e.g., user profile 904 and/or contextual information 906) and, based on the current parameters of the machine learning model 902, detect or predict a health emergency 910. The detection or prediction of a health emergency 910 may depend on the training data with labels 912 associated with the training data sample 918. Predicting a health issue refers to predicting a future event based on past and present data and most commonly by analysis of trends or data patterns. Prediction or predictive analysis employs probability based on the data analyses and processing. Detection of a health emergency refers to an onset of an emergency and the system detecting the same. Predicted events may or may not turn into an emergency based on how the turn of events happens. For example, the system based on a color of the skin appearing bluish may predict a breathing issue or a choking, but it may not turn into an emergency if the passenger starts recovering. However, if the skin color is not improving, then the system detects that it is a breathing issue/choking issue. For example, if the training label 912 indicates a particular type of health condition, e.g., diabetes, a seizure, a stroke, the machine learning model 902 would learn to detect the issue based on input data associated with a given user profile 904, contextual information 906 and/or sensor data 908. In an embodiment, during training, the detected health emergency at 910 and the training data with labels 912 may be compared at 914. For example, the comparison 914 may be based on a loss function that measures a difference between the detected health emergency 910 and the training data with labels 912. Based on the comparison at 914 or the corresponding output of the loss function, a training algorithm may update the parameters of the machine learning model 902, with the objective of minimizing the differences or loss between subsequent predictions or detections of the health emergency 910 and the corresponding labels 912. By iteratively training in this manner, the machine learning model 902 may "learn" from the different training data samples and become better at detecting various health emergencies at 910 that are similar to the ones represented by the training labels at 912. In an embodiment, the machine learning model 902 is trained using data which is specific to the passenger for which the model is used for detecting a health emergency. In an embodiment, the machine learning model 902 is trained using data which is general to the health condition and is used for a passenger for detecting a health emergency.

In an embodiment, sensor data 908 from the vehicle that is associated with a time segment (e.g., 5, 10, 30, or 60 seconds) may be labeled 912 or associated with one or more predetermined event types to represent what transpired or occurred in the vehicle during that time segment. For example, a particular training data sample 918 capturing a health emergency occurring in a vehicle may be labeled 912 or associated with a "health emergency" event type. For example, a particular training data sample 918 may pertain to a particular incident that occurred in the past. The training data sample 918 may be labeled 912 or associated with the "health emergency" event type, and the data 908 may include audiovisual data of the event as it was occurring, along with profile data 904 of the passenger. In an embodiment, the training data sample 918 may further include contextual information 906, such as the time of day of the ride, the weather, app-usage patterns associated with the ride request, etc.

Using the training data, a machine learning model 902 may be trained so that it recognizes features of input data that signify or correlate to certain event types. For example, a trained machine learning model 902 may recognize data features that signify the likelihood of an emergency situation, as an actionable event. In an embodiment, the features may have meaningful interpretations, such as excessive physical movements, no physical movement, clutching at the throat, inability to speak, breathe or swallow, coughing, wheezing or other unusual breathing sounds, gagging, a change in color (e.g., blue lips or red face), audible or gestured request for help, etc. In an embodiment, the symptoms of the disease or health emergency are used as training data or input data for training. For example, symptoms of rapid heart rate, bluish skin symptoms of hypoxemia will be used for mapping the symptoms to disease hypoxemia. The features may also be unintelligible to humans and may simply represent data patterns that tend to be present when certain event types occur. Through training, the machine learning model 902 may learn to identify predictive and non-predictive features and apply the appropriate weights to the features to optimize the machine learning model's 902 predictive accuracy. In embodiments where supervised learning is used and each training data sample 918 has a health emergency label 912, the training algorithm may iteratively process each training data sample 918 (including user profile data 904, contextual information 906, and/or sensor data 908), and generate a prediction of health emergency 910 based on the model's 902 current parameters. Based on the comparison 914 results, the training algorithm may adjust the model's 902 parameters/configurations (e.g., weights) accordingly to minimize the differences between the generated predictions of health emergency 910 and the corresponding labels 912. Any suitable machine learning model and training algorithm may be used, including, e.g., neural networks, decision trees, clustering algorithms, and any other suitable machine learning techniques. Once trained, the machine learning model 902 may take input data associated with a passenger and output one or more predictions that indicate a likelihood that a health emergency event has occurred. In an embodiment, the passenger and the vehicle associated with the input data may be different from any of the passengers and vehicles associated with the training data samples.

Figure 10:
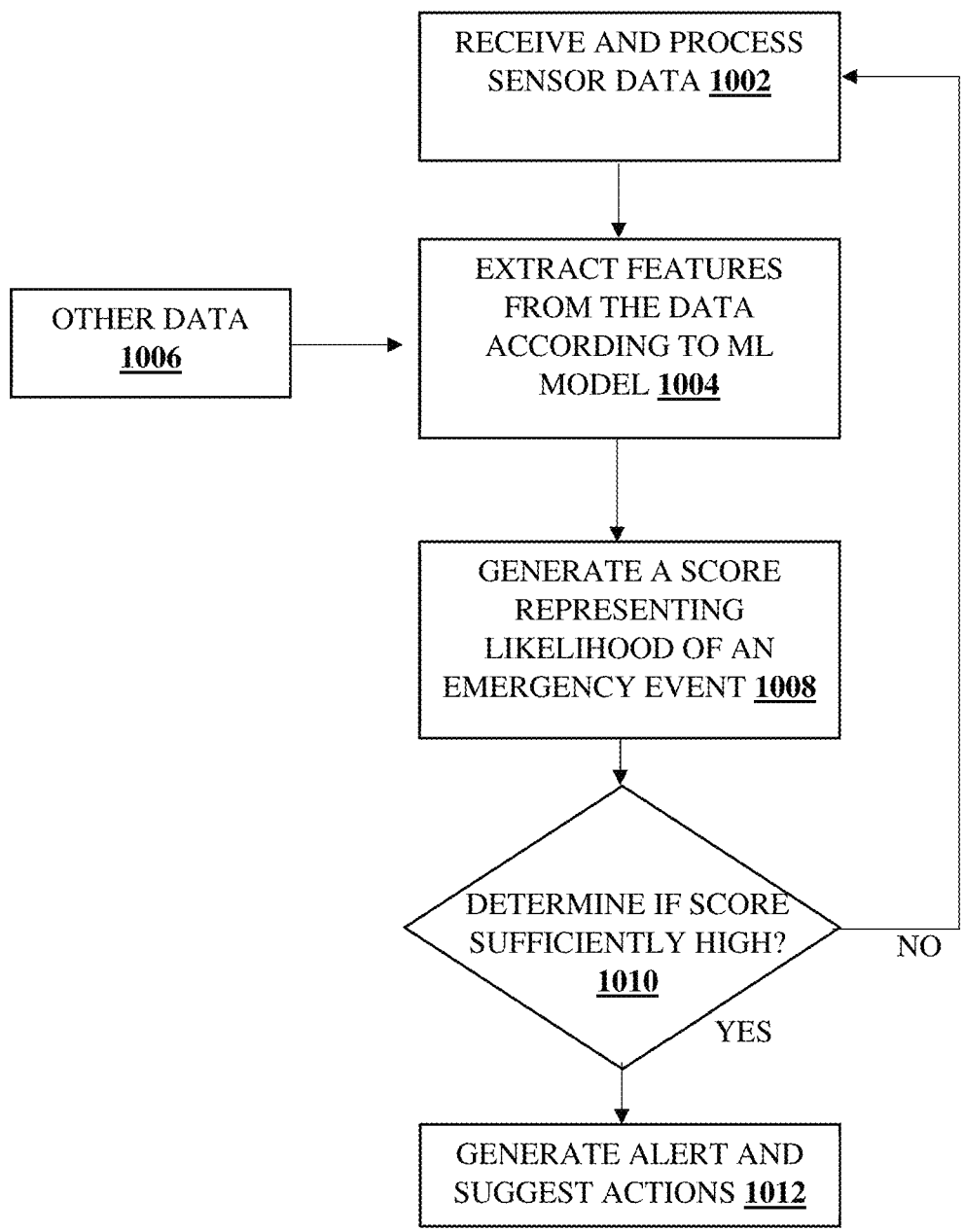
FIG. 10 shows an example flow chart for detecting a health emergency using a machine learning model according to an embodiment.

FIG. 10 shows an example flow chart for detecting a health emergency using a machine learning model. The system may receive data associated with sensor output(s) from one or more sensors in the vehicle as shown at 1002. Any type of sensor may be used to gather data pertaining to the passenger compartment of the vehicle. A sensor output may be, for example, images, videos, audios, LiDAR measures, infrared measures, temperature measures, GPS data, or any other information measured or detected by sensors. In an embodiment, a sensor output may be the result of one or more sensors capturing environmental information associated with the passenger compartment of the vehicle, which may include the passenger, driver, and any other passengers/occupants of the vehicle. For example, sensor output may be associated with a passenger in the vehicle including the driver. In an embodiment, data associated with sensor output may include the raw sensor output (e.g., the images, videos, audios, etc.) and/or data derived from processing the sensor output. For example, the vehicle's computer system, a vehicle device, or a cloud/network system may process the sensor data and generate derivative data. For example, derivative data from audio may include data representing pitch, tone, speech rate, and/or semantic information. As another example, derivative data from image, video or LiDAR data may include data representing identified objects, motion, movement speed, gestures, facial expressions, posture, eye position, etc. The system may receive any data associated with the sensor output from sensors, including raw sensory output and/or any derivative data. In an embodiment, the system may process the received data and identify any actionable event of interest using a machine learning model, trained using a set of training data.

As shown at 1004, the system may extract features from the received data according to a machine learning model. The machine learning model is able to automatically do so based on what it learned during the training process. In an embodiment, appropriate weights that were learned during the training process may be applied to the features. At step 1008, the machine learning model, based on the features of the received data, may generate a score representing a likelihood or confidence that the received data is associated with a particular event type, e.g., health emergency due to choking, health emergency due to hypoxemia, or simply health emergency, etc. As shown at 1010, the system may determine whether the score is sufficiently high relative to a threshold or criteria to warrant certain action. If the score is not sufficiently high, thus indicating that the detected event may not have actually occurred (in other words, a false-positive), the system may return to step 1002 and continue to monitor subsequent incoming data. On the other hand, if the score is sufficiently high, then at step 1012 the system may generate an appropriate alert and/or determine an appropriate action/response. In an embodiment, the system may send alerts to appropriate recipients based on the detected event types.

For instance, an alert is generated, and a message is sent to nearby vehicles. In an embodiment, an alert of a health emergency may be automatically sent to a nearby hospital, ambulatory service, and/or firefighters. An alert may additionally or alternatively be sent to one of the devices within the vehicle in which the event is occurring. For example, the alert may warn the passengers that events in the vehicle are being recorded, inform the passengers that an appropriate third-party has been contacted (e.g., police, ambulance, etc.), or provide guidance on what to do (e.g., remain calm in the vehicle, continue to nearby emergency care with step-by-step instructions, pull over, etc.). In situations where the driver of the vehicle is found to be in a panic or distressed due to the health emergency of a passenger in the vehicle or driver himself/herself having a health emergency, an autonomous vehicle mode is initiated, and the system may also instruct an autonomous vehicle to perform certain actions. For example, the system may determine an alternative destination different from the originally intended destination and instruct the autonomous vehicle to drive to that alternative destination. For instance, the vehicle may be instructed to drive to the nearest hospital in the event of a health emergency. In an embodiment, the system may also instruct nearby vehicles to reduce speed and the user vehicle to perform other actions, increasing/reducing speed in the event of a health emergency and/or pulling over.

In an embodiment, the system may repeat one or more steps of the method of FIG. 10, where appropriate. In an embodiment, the steps 1002 to 1012 may be performed by the system, any combination of those steps may be performed by any other computing system, for example a remote network or a cloud network. In an embodiment, where machine learning models are used for making such determination, the system may transmit a trained machine learning model to the computing system in the vehicle to allow event-detection to occur locally. This may be desirable since sensor data may be overly large to transmit to the remote system in a timely fashion. If the machine learning model takes as input other data (e.g., the passenger's medical data, medical pre-conditions, his social habits such as drinking, partying, sleeping habits, etc.), such information may be made available to the computing device executing the machine learning model (e.g., the computing device may obtain the data from the passenger's device). In an embodiment, the local computing device may send the event-detection determination to the system and let it perform the appropriate actions (e.g., generate alerts, etc., as described with reference to step 1012).

In an embodiment, the system is provided, wherein the facial expression recognition module utilizes a Convolutional Neural Networks (CNN) pre-training process; and/or wherein the machine learning (ML) algorithm contains a bounding box procedure around the subject's face; and/or wherein the bounding box procedure utilizes a Viola-Jones detection algorithm; and/or wherein the facial expression recognition module utilizes Facial Expression Recognition (FER) algorithms; and/or wherein the current behavioral classification is of emotional states of at least one of anger, happiness, and calm; and/or wherein the current behavioral classification is indicative of a health emergency; and/or wherein the current behavioral classification requires an action; and/or wherein the alerting is at least one of a light, a sound, an electronic message; and/or wherein the camera is a video camera. In yet another aspect of the disclosure, the above method is provided, wherein the step of learning utilizes a Convolutional Neural Networks (CNN) pre-training process; and/or wherein the detecting of a face of a passenger in the images is via a bounding box procedure; and/or further comprising using a Viola-Jones detection algorithm; and/or wherein the current behavioral classification is at least one of anger, happiness, and of a health emergency; and/or wherein the passenger experiences a health emergency; and/or wherein the step of alerting is via at least one of a light, a sound, an electronic message displayed via a display in the vehicle. In an embodiment, one or more currently obtained facial expressions from the camera are compared to thresholds for pre-trained emergency classifications and determine when a current classification is an emergency. When the current emergency classification is detected, requiring an action, a driver is alerted, signaling directly to provide real-time assistance. For instance, an event may be identified and classified as an emergency when the user's heart rate surpasses a predetermined threshold. In an embodiment, the thresholds can be varied. In an embodiment, Long-Short Term Memory-based Recurrent Neural Network module is used with current image or video sequences to predict an emergency when a user's facial expression changes (based on a threshold). The use of a recurrent neural network architecture comes from its ability to use past, temporal information for inference on current inputs. Long short term memories (LSTMs) offer a computationally efficient way to train these networks. For example, video sequences of individuals in emergency events can be used to train the LSTMs. By virtue of this training mechanism, the model can predict given real time video input when an emergency is imminent.

In an embodiment, multiple sensors can be utilized to gather information and thereafter develop "intelligence" on the passenger. In an embodiment, the system uses only image or video data to assess the person(s)' state or condition which is tailored to be non-contact monitoring. The system monitors the state of the passengers and, primarily via extracted facial expressions and changes of facial features with Artificial Intelligence (AI) assistance, is able to provide changes to the state of health in real time or in advance. The system is configured for continuous monitoring. The features can be processed with neural network algorithms with temporal modeling to capture primary and micro facial expressions to help detect and predict significant behavior changes of the passengers emotional and health state. In an embodiment, the system may recommend a treatment option through machine learning and prediction methodologies.

Nearby vehicles detection module: V2V would be based around a peer-to-peer mesh network where each element of the network (a vehicle) is able to generate, receive and relay messages. With this approach, an expansive network can be created in populated areas without the need for expensive infrastructure. Typically, each vehicle would be able to transmit information about their speed, direction, location, braking and turning intent. In an embodiment, V2V communication is used for detecting and communicating with the nearby vehicles. V2V would form a mesh network using dedicated short-range communications (DSRC). Dedicated short-range communication (DSRC) is a wireless communication technology designed to allow automobiles in the intelligent transportation system (ITS) to communicate with other automobiles or infrastructure technology.

Path generation module: Path generation module selects a region of a road of travel ahead of the vehicle based on sensor data indicative of the road of travel ahead of the user's vehicle; based on a speed and the location of the user's vehicle and based on the speed and location of the nearby vehicles the module determines a braking profile having a plurality of phases. While traveling within the region of the road, the user's vehicle system will determine a reduced speed for the user's vehicle to pull over and stop in the region. For each phase of the plurality of phases, a respective rate at which to reduce the speed of the user's vehicle while traveling within the region during the phase, and, for each phase of the plurality of phases, a respective lateral displacement of the user's vehicle navigates within the region during the phase and are determined by the system and are instructed to the driver. Based on the braking profile, a trajectory is determined for the vehicle to navigate within the region while reducing the speed of the vehicle in accordance with the braking profile. In an embodiment, the vehicle will be put in autonomous mode, and will be determining instructions to cause the user's vehicle to pull over and stop during travel and storing the instructions in a memory of the computing system accessible by at least one processor; and based on the stored instructions, the computing system can cause the user's vehicle to pull over and stop in the region while navigating along the trajectory and reducing the speed of the autonomous vehicle in accordance with the braking profile. In an embodiment, the instructions are presented to the driver via a display or via voice-based instructions, so as to assist the driver to pull over according to the computed path successfully. In an embodiment, the vehicle may not pull over but continue on a route to an emergency care facility by communicating along its path in the traffic with neighboring or surrounding vehicles.

In an embodiment, the system may comprise a cyber security module.

In one aspect, a secure communication management (SCM) computer device for providing secure data connections is provided. The SCM computer device includes a processor in communication with memory. The processor is programmed to receive, from a first device, a first data message. The first data message is in a standardized data format. The processor is also programmed to analyze the first data message for potential cyber security threats. If the determination is that the first data message does not contain a cyber security threat, the processor is further programmed to convert the first data message into a first data format associated with the vehicle environment and transmit the converted first data message to the vehicle system using a first communication protocol associated with the vehicle system.

According to an embodiment, secure authentication for data transmissions comprises, provisioning a hardware-based security engine (HSE) located in communications system, said HSE having been manufactured in a secure environment and certified in said secure environment as part of an approved network; performing asynchronous authentication, validation and encryption of data using said HSE, storing user permissions data and connection status data in an access control list used to define allowable data communications paths of said approved network, enabling communications of the communications system with other computing system subjects to said access control list, performing asynchronous validation and encryption of data using security engine including identifying a user device (UD) that incorporates credentials embodied in hardware using a hardware-based module provisioned with one or more security aspects for securing the system, wherein security aspects comprising said hardware-based module communicating with a user of said user device and said HSE.

Figure 11A:
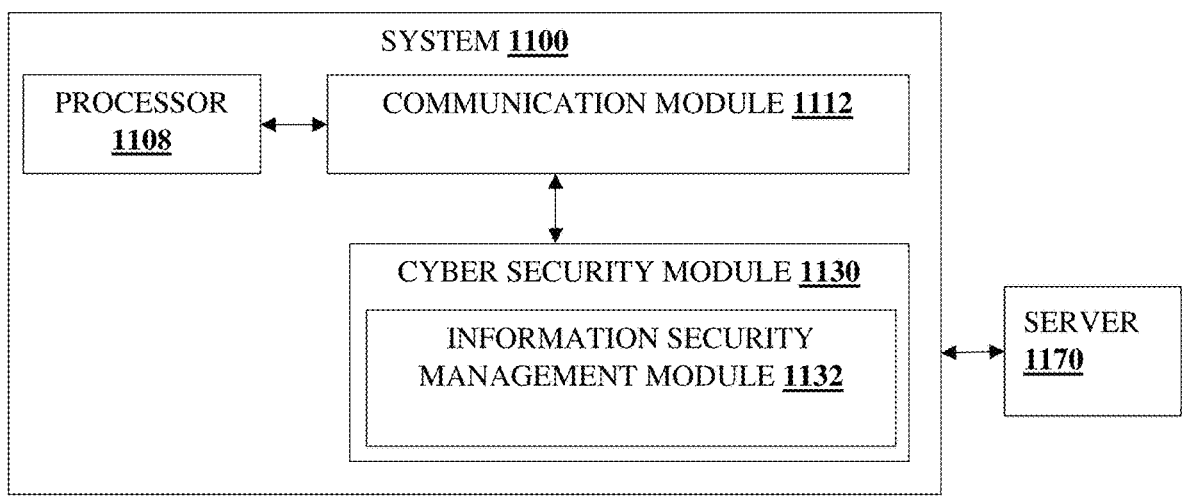
FIG. 11A shows a block diagram of the cyber security module in view of the system and server.

In an embodiment, FIG. 11A shows the block diagram of the cyber security module. The communication of data between the system 1100 and the server 1170 through the communication module 1112 is first verified by the information security management module 1132 before being transmitted from the system to the server or from the server to the system. The information security management module is operable to analyze the data for potential cyber security threats, to encrypt the data when no cyber security threat is detected, and to transmit the data encrypted to the system or the server.

Figure 11B:
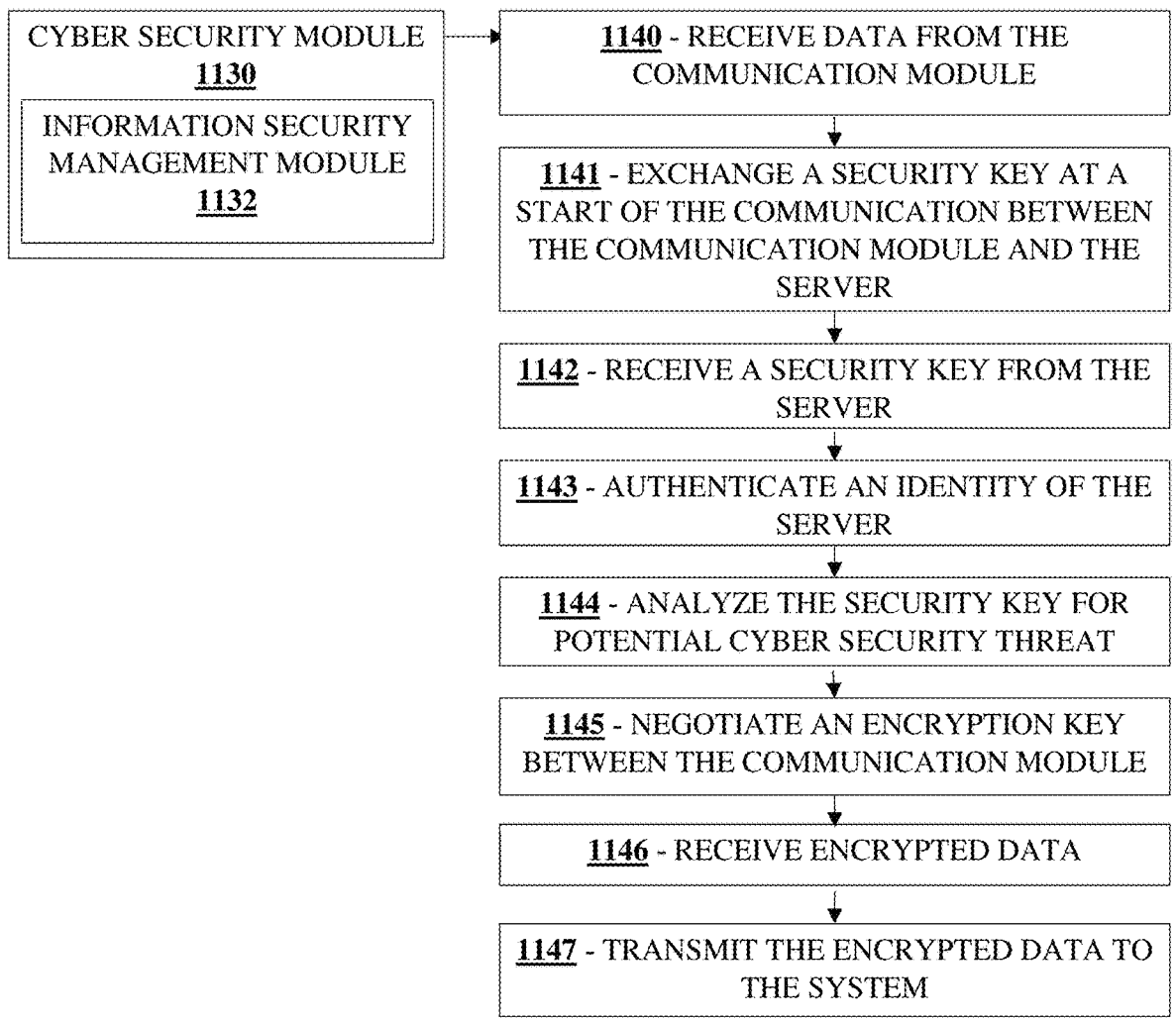
FIG. 11B shows an embodiment of the cyber security module.

In an embodiment, the cyber security module further comprises an information security management module providing isolation between the system and the server. FIG. 11B shows the flowchart of securing the data through the cyber security module 1130. At step 1140, the information security management module is operable to receive data from the communication module. At step 1141, the information security management module exchanges a security key at the start of the communication between the communication module and the server. At step 1142, the information security management module receives a security key from the server. At step 1143, the information security management module authenticates an identity of the server by verifying the security key. At step 1144, the information security management module analyzes the security key for potential cyber security threats. At step 1145, the information security management module negotiates an encryption key between the communication module and the server. At step 1146, the information security management module receives the encrypted data. At step 1147, the information security management module transmits the encrypted data to the server when no cyber security threat is detected.

Figure 11C:
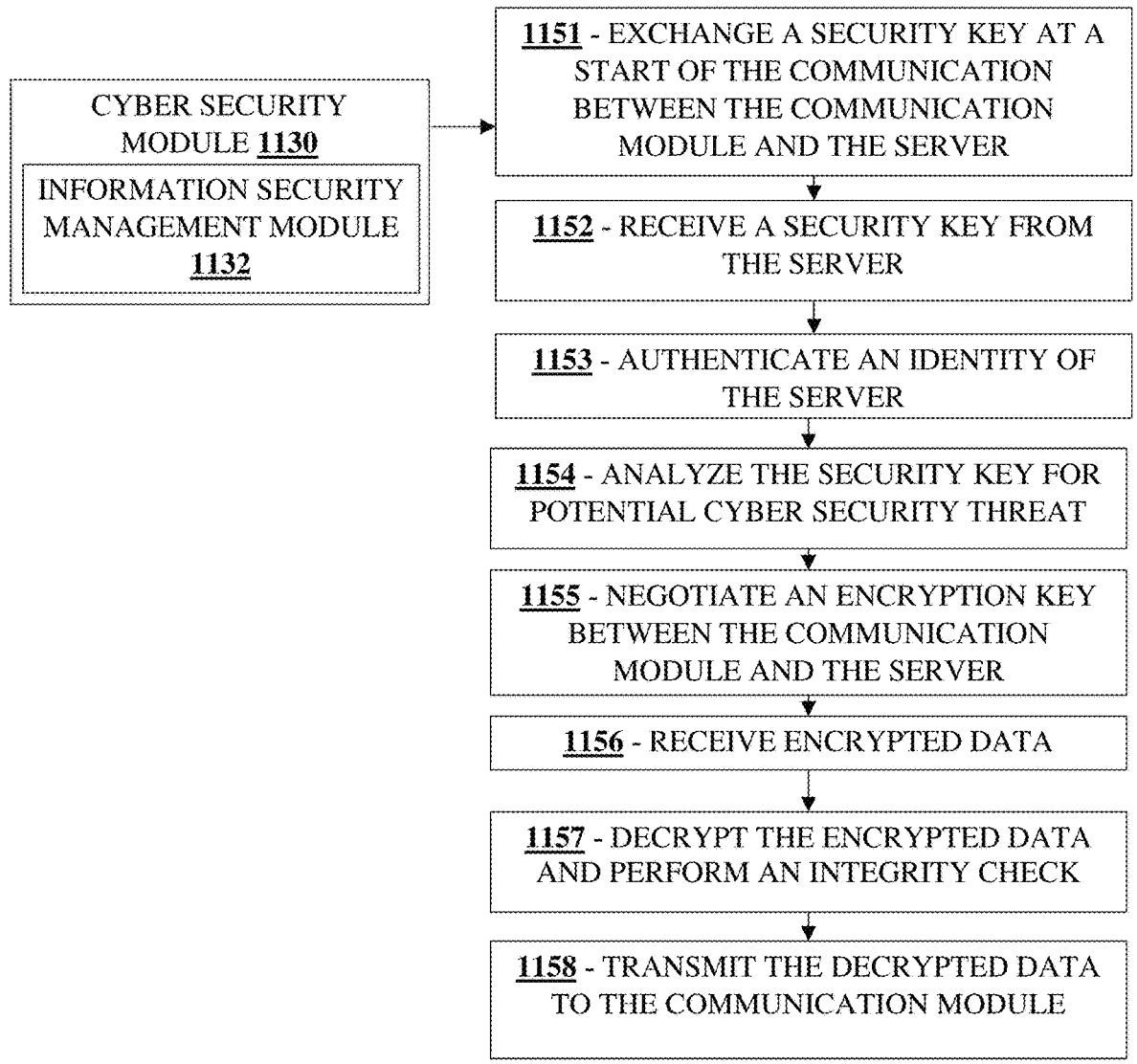
FIG. 11C shows another embodiment of the cyber security module.

In an embodiment, FIG. 11C shows the flowchart of securing the data through the cyber security module 1130. At step 1151, the information security management module is operable to: exchange a security key at the start of the communication between the communication module and the server. At step 1152, the information security management module receives a security key from the server. At step 1153, the information security management module authenticates an identity of the server by verifying the security key. At step 1154, the information security management module analyzes the security key for potential cyber security threats. At step 1155, the information security management module negotiates an encryption key between the communication module and the server. At step 1156, the information security management module receives encrypted data. At step 1157, the information security management module decrypts the encrypted data, and performs an integrity check of the decrypted data. At step 1158, the information security management module transmits the decrypted data to the communication module when no cyber security threat is detected.

In an embodiment, the integrity check is a hash-signature verification using a Secure Hash Algorithm 256 (SHA256) or a similar method.

In an embodiment, the information security management module is configured to perform asynchronous authentication and validation of the communication between the communication module and the server.

In an embodiment, the information security management module is configured to raise an alarm if a cyber security threat is detected. In an embodiment, the information security management module is configured to discard the encrypted data received if the integrity check of the encrypted data fails.

In an embodiment, the information security management module is configured to check the integrity of the decrypted data by checking accuracy, consistency, and any possible data loss during the communication through the communication module.

In an embodiment, the server is physically isolated from the system through the information security management module. When the system communicates with the server as shown in FIG. 11A, identity authentication is first carried out on the system and the server. The system is responsible for communicating/exchanging a public key of the system and a signature of the public key with the server. The public key of the system and the signature of the public key are sent to the information security management module. The information security management module decrypts the signature and verifies whether the decrypted public key is consistent with the received original public key or not. If the decrypted public key is verified, the identity authentication is passed. Similarly, the system and the server carry out identity authentication on the information security management module. After the identity authentication is passed on to the information security management module, the two communication parties, the system, and the server, negotiate an encryption key and an integrity check key for data communication of the two communication parties through the authenticated asymmetric key. A session ID number is transmitted in the identity authentication process, so that the key needs to be bound with the session ID number; when the system sends data to the outside, the information security gateway receives the data through the communication module, performs integrity authentication on the data, then encrypts the data through a negotiated secret key, and finally transmits the data to the server through the communication module. When the information security management module receives data through the communication module, the data is decrypted first, integrity verification is carried out on the data after decryption, and if verification is passed, the data is sent out through the communication module; otherwise, the data is discarded.

In an embodiment, the identity authentication is realized by adopting an asymmetric key with a signature.

In an embodiment, the signature is realized by a pair of asymmetric keys which are trusted by the information security management module and the system, wherein the private key is used for signing the identities of the two communication parties, and the public key is used for verifying that the identities of the two communication parties are signed. Signing identity comprises a public and a private key pair. In other words, signing identity is referred to as the common name of the certificates which are installed in the user's machine.

In an embodiment, both communication parties need to authenticate their own identities through a pair of asymmetric keys, and a task in charge of communication with the information security management module of the system is identified by a unique pair of asymmetric keys.

In an embodiment, the dynamic negotiation key is encrypted by adopting an Rivest-Shamir-Adleman (RSA) encryption algorithm. RSA is a public-key cryptosystem that is widely used for secure data transmission. The negotiated keys include a data encryption key and a data integrity check key.

In an embodiment, the data encryption method is a Triple Data Encryption Algorithm (3DES) encryption algorithm. The integrity check algorithm is a Hash-based Message Authentication Code (HMAC-MD5-128) algorithm. When data is output, the integrity check calculation is carried out on the data, the calculated Message Authentication Code (MAC) value is added with the header of the value data message, then the data (including the MAC of the header) is encrypted by using a 3DES algorithm, the header information of a security layer is added after the data is encrypted, and then the data is sent to the next layer for processing. In an embodiment the next layer refers to a transport layer in the Transmission Control Protocol/Internet Protocol (TCP/IP) model.

The information security management module ensures the safety, reliability, and confidentiality of the communication between the system and the server through the identity authentication when the communication between the two communication parties starts the data encryption and the data integrity authentication. The method is particularly suitable for an embedded platform which has less resources and is not connected with a Public Key Infrastructure (PKI) system and can ensure that the safety of the data on the server cannot be compromised by a hacker attack under the condition of the Internet by ensuring the safety and reliability of the communication between the system and the server.

Figure 12:
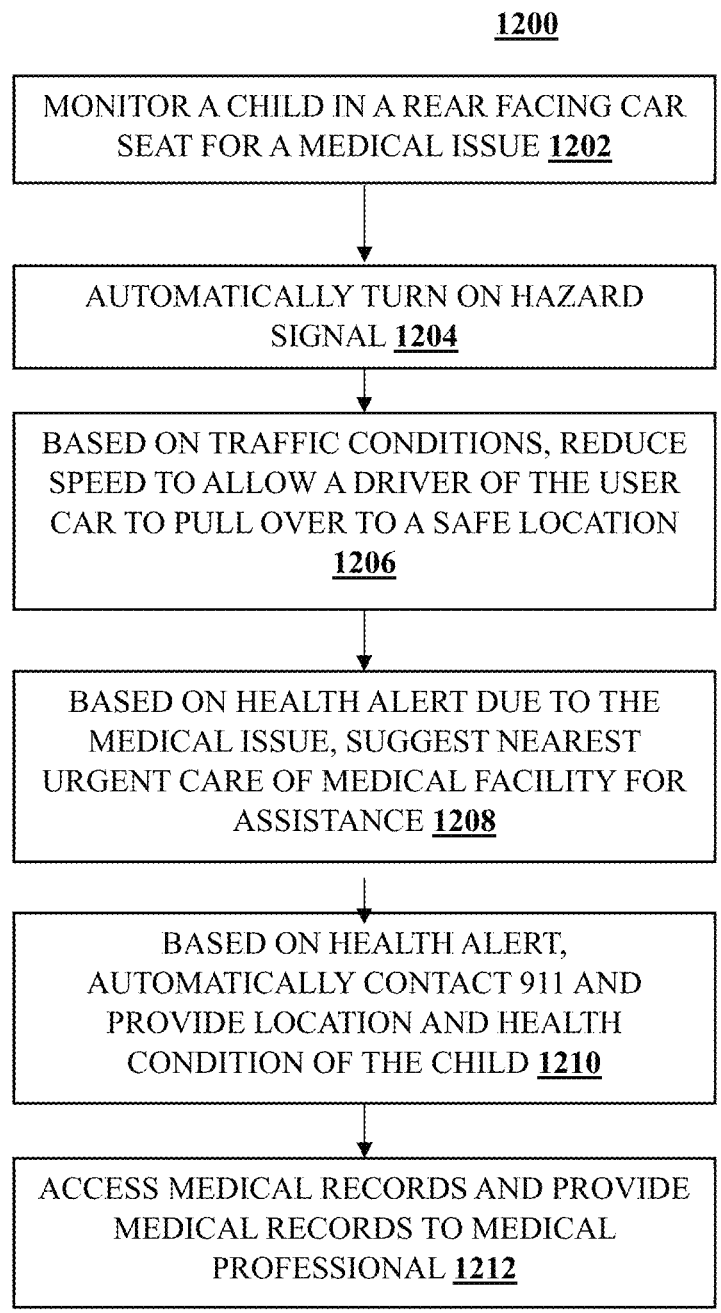
FIG. 12 shows a flowchart for a method for monitoring the health emergency of a child in a rear facing car seat of the vehicle and assisting in the emergency situation according to an embodiment.

FIG. 12 shows a flowchart for a method for monitoring the health emergency of a child in a rear facing car seat of the vehicle and assisting in the emergency situation according to an embodiment. According to an embodiment, it is a computer system of a car, wherein the computer system is configured to, monitor a child in a rear facing car seat for a medical issue as shown at 1202, automatically turn on hazard signal as shown at 1204, based on traffic conditions reduce speed to allow a driver of the car to pull over to a safe location as shown at 1206, based on health alert due to the medical issue suggest nearest urgent care of medical facility for assistance as shown at 1208, based on health alert automatically contact 911 and provide location and health condition of the child as shown at 1210, and access medical records and provide medical records to medical professional as shown at 1212.

In an embodiment authorization for the access of the medical records is received from the user prior to an occurrence of the medical issue.

What is claimed is:
1. A system, comprising:
a sensor; a communication module; and a processor;
wherein the processor performs, under power, following functions, wherein the functions comprise:
automatic detection, by the processor using a signal from the sensor, that a passenger of a vehicle is experiencing a medical emergency;
automatic generation of an alert signal on an infotainment system of the vehicle;
automatic turn on, by the processor, an emergency indication light, wherein the emergency indication light is visible to a nearby vehicle;

automatic generation of a path from a current location of the vehicle to a target location;

maneuver, the vehicle along the path to the target location;

automatic identification, by the processor, of a medical facility based upon a location of the vehicle;

automatic contact, by the processor via the communication module, to an emergency service and providing the location of the vehicle and a health condition of the passenger of the vehicle; and automatic transmission, by the processor via the communication module, of a medical record of the passenger of the vehicle to the medical facility; and wherein authorization to access the medical record is received from the passenger in advance.

2. The system of claim 1, wherein the system is configured to be a component of the vehicle; and wherein the passenger is a child in a rear facing car seat.

3. The system of claim 1, wherein the system simultaneously identifies the medical facility and contact the emergency service while driver of the vehicle is maneuvering the vehicle along the path to the target location.

4. The system of claim 1, wherein the health condition of the passenger is due to at least one of a choking, a fever, a breathing issue, a change in vital signs indicating a problem in physiological function of the passenger.

5. The system of claim 1, wherein the sensor comprises at least one of a temperature sensor, a heart rate sensor, a respiration sensor, a blood pressure sensor, and a perspiration sensor.

6. The system of claim 1, wherein the communication module is enabled for at least one of a vehicle-to-vehicle communication, a vehicle-to-infrastructure communication, and a vehicle-to-everything communication.

7. The system of claim 1, wherein the alert signal comprises at least one of a text message, a display, a sound, a light, and a combination thereof.

8. The system of claim 1, wherein the target location is a pull over location.

9. The system of claim 1, wherein the target location is a location of the medical facility.

10. The system of claim 1, wherein the vehicle further comprises an image sensor configured to capture an image of the passenger.

11. The system of claim 1, wherein the processor further comprises a machine learning algorithm aided by artificial intelligence configured to detect the medical emergency.

12. The system of claim 1, wherein a pull over decision is made based on a first health data of the passenger and a second health data of driver of the vehicle.

13. A method, comprising:
automatically detecting, by a processor using a signal from a sensor, that a passenger of a vehicle is experiencing a medical emergency;

automatically generating an alert signal on an infotainment system of the vehicle;

automatically turning on, by the processor, an emergency indication light, wherein the emergency indication light is visible to a nearby vehicle;

automatically generating a path from a current location of the vehicle to a target location;

maneuvering, the vehicle along the path to the target location;

automatically identifying, by the processor, a medical facility based upon a location of the vehicle;

automatically contacting, by the processor via a communication module, an emergency service and providing the location of the vehicle and a health condition of the passenger of the vehicle; and automatically transmitting, by the processor via the communication module, a medical record of the passenger of the vehicle to the medical facility; and wherein authorization to access the medical record is received from the passenger in advance.

14. The method of claim 13, wherein the vehicle senses a speed of the nearby vehicle for determining the path to the target location and transmits a message with a first instruction for speed, and a second instruction for course to the nearby vehicle.

15. The method of claim 14, wherein the first instruction for speed comprises at least one of a reduction in speed, a maintenance of speed, an increase in speed, and complete stop.

16. The method of claim 14, wherein the second instruction for course comprises at least one of a lane keeping, a lane changing, and a pull over to a side of a road.

17. The method of claim 14, wherein the message is at least one of a broadcast message and an individualized message for the nearby vehicle.

18. The method of claim 14, wherein the message is displayed on the infotainment system of the nearby vehicle, wherein the nearby vehicle displays a first graphic of the vehicle, a second graphic of the nearby vehicle, the path, and the target location on the infotainment system of the nearby vehicle.

19. The method of claim 13, wherein the method further comprises determining zones of influence based on a distance of the nearby vehicle from the vehicle and a first speed of the nearby vehicle relative to a second speed of the vehicle, wherein the zones of influence comprise a high influence zone, a medium influence zone and a low influence zone.

20. A non-transitory computer-readable medium having stored thereon instructions executable by a computer system to perform operations comprising:
automatically detecting, by a processor using a signal from a sensor, that a passenger of a vehicle is experiencing a medical emergency;

automatically generating an alert signal on an infotainment system of the vehicle;

automatically turning on, by the processor, an emergency indication light, wherein the emergency indication light is visible to a nearby vehicle;

automatically generating, a path from a current location of the vehicle to a target location;

maneuvering, the vehicle along the path to the target location;

automatically identifying, by the processor, a medical facility based upon a location of the vehicle;

automatically contacting, by the processor via a communication module, an emergency service and providing the location of the vehicle and a health condition of the passenger of the vehicle; and automatically providing, by the processor via the communication module, a medical record of the passenger of the vehicle to the medical facility; and wherein authorization to access the medical record is received from the passenger in advance.

* * * * *